United States Patent
Schwake et al.

(10) Patent No.: US 10,286,038 B2
(45) Date of Patent: May 14, 2019

(54) LYSOSOME MEMBRANE PROTEIN 2 (LIMP-2) BASED PEPTIDES AND RELATED USES

(71) Applicant: Northwestern University, Evanston, IL (US)

(72) Inventors: Michael Schwake, Chicago, IL (US); Dimitri Krainc, Chicago, IL (US)

(73) Assignee: Northwestern University, Evanston, IL (US)

( * ) Notice: Subject to any disclaimer, the term of this patent is extended or adjusted under 35 U.S.C. 154(b) by 6 days.

(21) Appl. No.: 15/455,809

(22) Filed: Mar. 10, 2017

(65) Prior Publication Data
US 2017/0258870 A1    Sep. 14, 2017

Related U.S. Application Data

(60) Provisional application No. 62/307,179, filed on Mar. 11, 2016.

(51) Int. Cl.
*A61K 38/16* (2006.01)
*C07K 14/00* (2006.01)
*A61K 38/17* (2006.01)
*G01N 33/573* (2006.01)

(52) U.S. Cl.
CPC .......... *A61K 38/177* (2013.01); *A61K 38/162* (2013.01); *C12Y 302/01045* (2013.01); *G01N 33/573* (2013.01); *G01N 2333/924* (2013.01); *G01N 2500/02* (2013.01); *G01N 2500/20* (2013.01)

(58) Field of Classification Search
CPC .... A61K 38/162; A61K 38/177; A61K 38/16; C12N 2740/16022; C12Y 302/01045; G01N 2333/924; G01N 2500/02; G01N 2500/20; G01N 33/573; C07K 14/00
USPC ........ 530/300, 324, 325; 514/1.1, 21.3, 21.4
See application file for complete search history.

(56) References Cited

U.S. PATENT DOCUMENTS

| | | | | |
|---|---|---|---|---|
| 4,966,848 A * | 10/1990 | Smith | ................... | C12N 9/1029 435/193 |
| 5,223,421 A * | 6/1993 | Smith | ................... | C12N 9/1029 435/193 |
| 5,837,218 A * | 11/1998 | Peers | ................... | A61K 51/088 424/1.69 |
| 8,962,273 B2 * | 2/2015 | Reczek | .............. | C12N 15/1138 435/200 |
| 2014/0243268 A1 * | 8/2014 | Mei | ........................ | C07K 14/71 514/9.6 |

OTHER PUBLICATIONS

UniProt A0A1W2PSE4, pp. 1-5. Integrated into UniProtKB/TrEMBL Jun. 7, 2017.*

Adler J & Parmryd I (2010) Quantifying Colocalization by Correlation: The Pearson Correlation Coefficient is Superior to the Mander's Overlap Coefficient. Cytom Part A 77A(8):733-742.

Atrian S, et al. (2008) An evolutionary and structure-based docking model for glucocerebrosidase-saposin C and glucocerebrosidase-substrate interactions—relevance for Gaucher disease. Proteins 70(3):882-891.

Benito JM, Garcia Fernandez JM, & Ortiz Mellet C (2011) Pharmacological chaperone therapy for Gaucher disease: a patent review. Expert opinion on therapeutic patents 21(6):885-903.

Berkovic SF, et al. (2008) Array-based gene discovery with three unrelated subjects shows SCARB2/LIMP-2 deficiency causes myoclonus epilepsy and glomerulosclerosis. American journal of human genetics 82(3):673-684.

Blanz J, et al. (2010) Disease-causing mutations within the lysosomal integral membrane protein type 2 (LIMP-2) reveal the nature of binding to its ligand beta-glucocerebrosidase. Hum.Mol.Genet. 19(4):563-572.

Blanz J, et al. (2015) Mannose 6-phosphate-independent Lysosomal Sorting of LIMP-2. Traffic 16(10):1127-1136.

Bras J, et al. (2014) Genetic analysis implicates APOE, SNCA and suggests lysosomal dysfunction in the etiology of dementia with Lewy bodies. Human molecular genetics 23(23):6139-6146.

Brumshtein B, Wormald MR, Silman I, Futerman AH, & Sussman JL (2006) Structural comparison of differently glycosylated forms of acid-beta-glucosidase, the defective enzyme in Gaucher disease. Acta Crystallogr.D.Biol. Crystallogr. 62(Pt 12):1458-1465.

Cormand B, et al. (1998) Mutation analysis of Gaucher disease patients from Argentina: high prevalence of the RecNcil mutation. American journal of medical genetics 80(4):343-351.

Dusterhoft S, et al. (2015) Extracellular Juxtamembrane Segment of ADAM17 Interacts with Membranes and Is Essential for Its Shedding Activity. Biochemistry 54(38):5791-5801.

Dvir H, et al. (2003) X-ray structure of human acid-beta-glucosidase, the defective enzyme in Gaucher disease. EMBO Rep. 4(7):704-709.

Frankel AD & Pabo CO (1988) Cellular uptake of the tat protein from human immunodeficiency virus. Cell 55 (6)1189-1193.

Gegg ME, et al. (2012) Glucocerebrosidase deficiency in substantia nigra of parkinson disease brains. Annals of neurology 72(3):455-463.

(Continued)

*Primary Examiner* — Julie Ha
(74) *Attorney, Agent, or Firm* — Andrus Intellectual Property Law, LLP

(57) ABSTRACT

A group of LIMP-2 peptides, LIMP-2 polypeptides, variants thereof, and pharmaceutical compositions comprising the LIMP-2 peptides, LIMP-2 polypeptides, or variants thereof are described. The disclosed peptides and polypeptides preferably comprise an amino acid sequence that is sufficient for providing a biological activity associated with LIMP-2, which may include binding and/or activating biological molecules such as β-glucocerebrosidase and binding viral protein 1 (VP1) of enterovirus 71 (E71) or coxsackievirus A16 (CA16). Also disclosed are methods of using the LIMP-2 peptides, LIMP-2 polypeptides, and variants thereof as therapeutics for treating diseases and disorders associated with β-glucocerebrosidase activity in subjects in need thereof.

7 Claims, 42 Drawing Sheets
Specification includes a Sequence Listing.

(56) References Cited

OTHER PUBLICATIONS

Grace ME, Graves PN, Smith FI, & Grabowski GA (1990) Analyses of catalytic activity and inhibitor binding of human acid beta-glucosidase by site-directed mutagenesis. Identification of residues critical to catalysis and evidence for causality of two Ashkenazi Jewish Gaucher disease type 1 mutations. The Journal of biological chemistry 265 (12):6827-6835.

Horst M, Knecht EC, & Schu PV (1999) Import into and degradation of cytosolic proteins by isolated yeast vacuoles. Molecular biology of the cell 10(9):2879-2889.

Hruska KS, LaMarca ME, Scott CR, & Sidransky E (2008) Gaucher disease: mutation and polymorphism spectrum in the glucocerebrosidase gene (GBA). Human mutation 29(5):567-583.

Kawame H & Eto Y (1991) A new glucocerebrosidase-gene missense mutation responsible for neuronopathic Gaucher disease in Japanese patients. American journal of human genetics 49(6):1378-1380.

Lieberman RL (2011) A Guided Tour of the Structural Biology of Gaucher Disease: Acid-beta-Glucosidase and Saposin C. Enzyme research 2011:973231.

Liou B, et al. (2006) Analyses of variant acid beta-glucosidases: effects of Gaucher disease mutations. The Journal of biological chemistry 281(7):4242-4253.

Liou B, Haffey WD, Greis KD, & Grabowski GA (2014) The LIMP-2/SCARB2 binding motif on acid beta-glucosidase: basic and applied implications for Gaucher disease and associated neurodegenerative diseases. The Journal of biological chemistry 289(43):30063-30074.

Mazzulli JR, et al. (2011) Gaucher disease glucocerebrosidase and alpha-synuclein form a bidirectional pathogenic loop in synucleinopathies. Cell 146(1):37-52.

Mazzulli JR, Zunke F, Isacson O, Studer L, & Krainc D (2016) alpha-Synuclein-induced lysosomal dysfunction occurs through disruptions in protein trafficking in human midbrain synucleinopathy models. Proceedings of the National Academy of Sciences of the United States of America. Feb. 16, 2016;113(7):1931-6.

Nalls MA, et al. (2013) A multicenter study of glucocerebrosidase mutations in dementia with Lewy bodies. JAMA neurology 70(6):727-735.

Neculai D, et al. (2013) Structure of LIMP-2 provides functional insights with implications for SR-BI and CD36. Nature 604(7478):172-176.

Pastores GM, et al. (2004) Therapeutic goals in the treatment of Gaucher disease. Seminars in hematology 41(4 Suppl 6):4-14.

Patnaik S, et al. (2012) Discovery, structure-activity relationship, and biological evaluation of noninhibitory small molecule chaperones of glucocerebrosidase. Journal of medicinal chemistry 55(12):5734-5748.

Pearson K (1909) Determination of the Coefficient of Correlation. Science 30(757):23-25.

Reczek D, et al. (2007) LIMP-2 is a receptor for lysosomal mannose-6-phosphate-independent targeting of beta-glucocerebrosidase. Cell 131(4):770-783.

Rothaug M, et al. (2014) LIMP-2 expression is critical for beta-glucocerebrosidase activity and alpha-synuclein clearance. Proceedings of the National Academy of Sciences of the United States of America 111(43):15573-15578.

Sardi SP, et al. (2013) Augmenting CNS glucocerebrosidase activity as a therapeutic strategy for parkinsonism and other Gaucher-related synucleinopathies. Proceedings of the National Academy of Sciences of the United States of America 110(9):3537-3542.

Sardi SP, et al. (2011) CNS expression of glucocerebrosidase corrects alpha-synuclein pathology and memory in a mouse model of Gaucher-related synucleinopathy. Proceedings of the National Academy of Sciences of the United States of America 108(29):12101-12106.

Siebert M, Sidransky E, & Westbroek W (2014) Glucocerebrosidase is shaking up the synucleinopathies. Brain : a journal of neurology 137(Pt 5):1304-1322.

Sly WS, Kaplan A, Achord DT, Brot FE, & Bell CE (1978) Receptor-mediated uptake of lysosomal enzymes. Progress in clinical and biological research 23:547-551.

Stahl PD, Rodman JS, Miller MJ, & Schlesinger PH (1978) Evidence for receptor-mediated binding of glycoproteins, glycoconjugates, and lysosomal glycosidases by alveolar macrophages. Proceedings of the National Academy of Sciences of the United States of America 75(3):1399-1403.

Steet RA, et al. (2006) The iminosugar isofagomine increases the activity of N370S mutant acid beta-glucosidase in Gaucher fibroblasts by several mechanisms. Proceedings of the National Academy of Sciences of the United States of America 103(37):13813-13818.

Westbroek W, Gustafson AM, & Sidransky E (2011) Exploring the link between glucocerebrosidase mutations and parkinsonism. Trends in molecular medicine 17(9):485-493.

Zhao Y, Ren J, Padilla-Parra S, Fry EE, & Stuart DI (2014) Lysosome sorting of beta-glucocerebrosidase by LIMP-2 is targeted by the mannose 6-phosphate receptor. Nature communications 5:4321.

\* cited by examiner

A

SEQUENCE LISTING

```
<160> NUMBER OF SEQ ID NOS: 22

<210> SEQ ID NO 1
<211> LENGTH: 478
<212> TYPE: PRT
<213> ORGANISM: Homo sapien

<400> SEQUENCE: 1

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95

Lys Ala Asn Ile Gln Phe Gly Asp Asn Gly Thr Thr Ile Ser Ala Val
            100                 105                 110

Ser Asn Lys Ala Tyr Val Phe Glu Arg Asp Gln Ser Val Gly Asp Pro
        115                 120                 125

Lys Ile Asp Leu Ile Arg Thr Leu Asn Ile Pro Val Leu Thr Val Ile
    130                 135                 140

Glu Trp Ser Gln Val His Phe Leu Arg Glu Ile Ile Glu Ala Met Leu
145                 150                 155                 160

Lys Ala Tyr Gln Gln Lys Leu Phe Val Thr His Thr Val Asp Glu Leu
                165                 170                 175

Leu Trp Gly Tyr Lys Asp Glu Ile Leu Ser Leu Ile His Val Phe Arg
            180                 185                 190

Pro Asp Ile Ser Pro Tyr Phe Gly Leu Phe Tyr Glu Lys Asn Gly Thr
        195                 200                 205

Asn Asp Gly Asp Tyr Val Phe Leu Thr Gly Glu Asp Ser Tyr Leu Asn
    210                 215                 220
```

```
Phe Thr Lys Ile Val Glu Trp Asn Gly Lys Thr Ser Leu Asp Trp Trp
225                 230                 235                 240

Ile Thr Asp Lys Cys Asn Met Ile Asn Gly Thr Asp Gly Asp Ser Phe
            245                 250                 255

His Pro Leu Ile Thr Lys Asp Glu Val Leu Tyr Val Phe Pro Ser Asp
        260                 265                 270

Phe Cys Arg Ser Val Tyr Ile Thr Phe Ser Asp Tyr Glu Ser Val Gln
    275                 280                 285

Gly Leu Pro Ala Phe Arg Tyr Lys Val Pro Ala Glu Ile Leu Ala Asn
290                 295                 300

Thr Ser Asp Asn Ala Gly Phe Cys Ile Pro Glu Gly Asn Cys Leu Gly
305                 310                 315                 320

Ser Gly Val Leu Asn Val Ser Ile Cys Lys Asn Gly Ala Pro Ile Ile
                325                 330                 335

Met Ser Phe Pro His Phe Tyr Gln Ala Asp Glu Arg Phe Val Ser Ala
            340                 345                 350

Ile Glu Gly Met His Pro Asn Gln Glu Asp His Glu Thr Phe Val Asp
        355                 360                 365

Ile Asn Pro Leu Thr Gly Ile Ile Leu Lys Ala Ala Lys Arg Phe Gln
    370                 375                 380

Ile Asn Ile Tyr Val Lys Lys Leu Asp Asp Phe Val Glu Thr Gly Asp
385                 390                 395                 400

Ile Arg Thr Met Val Phe Pro Val Met Tyr Leu Asn Glu Ser Val His
                405                 410                 415

Ile Asp Lys Glu Thr Ala Ser Arg Leu Lys Ser Met Ile Asn Thr Thr
            420                 425                 430

Leu Ile Ile Thr Asn Ile Pro Tyr Ile Ile Met Ala Leu Gly Val Phe
        435                 440                 445

Phe Gly Leu Val Phe Thr Trp Leu Ala Cys Lys Gly Gln Gly Ser Met
    450                 455                 460

Asp Glu Gly Thr Ala Asp Glu Arg Ala Pro Leu Ile Arg Thr
465                 470                 475

<210> SEQ ID NO 2
<211> LENGTH: 335
<212> TYPE: PRT
<213> ORGANISM: Homo sapien

<400> SEQUENCE: 2

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Ser Leu Asp Trp
                85                  90                  95

Trp Ile Thr Asp Lys Cys Asn Met Ile Asn Gly Thr Asp Gly Asp Ser
            100                 105                 110

Phe His Pro Leu Ile Thr Lys Asp Glu Val Leu Tyr Val Phe Pro Ser
        115                 120                 125
```

-continued

```
Asp Phe Cys Arg Ser Val Tyr Ile Thr Phe Ser Asp Tyr Glu Ser Val
            130                 135                 140

Gln Gly Leu Pro Ala Phe Arg Tyr Lys Val Pro Ala Glu Ile Leu Ala
145                 150                 155                 160

Asn Thr Ser Asp Asn Ala Gly Phe Cys Ile Pro Glu Gly Asn Cys Leu
                165                 170                 175

Gly Ser Gly Val Leu Asn Val Ser Ile Cys Lys Asn Gly Ala Pro Ile
            180                 185                 190

Ile Met Ser Phe Pro His Phe Tyr Gln Ala Asp Glu Arg Phe Val Ser
        195                 200                 205

Ala Ile Glu Gly Met His Pro Asn Gln Glu Asp His Glu Thr Phe Val
210                 215                 220

Asp Ile Asn Pro Leu Thr Gly Ile Ile Leu Lys Ala Ala Lys Arg Phe
225                 230                 235                 240

Gln Ile Asn Ile Tyr Val Lys Lys Leu Asp Asp Phe Val Glu Thr Gly
                245                 250                 255

Asp Ile Arg Thr Met Val Phe Pro Val Met Tyr Leu Asn Glu Ser Val
            260                 265                 270

His Ile Asp Lys Glu Thr Ala Ser Arg Leu Lys Ser Met Ile Asn Thr
        275                 280                 285

Thr Leu Ile Ile Thr Asn Ile Pro Tyr Ile Ile Met Ala Leu Gly Val
290                 295                 300

Phe Phe Gly Leu Val Phe Thr Trp Leu Ala Cys Lys Gly Gln Gly Ser
305                 310                 315                 320

Met Asp Glu Gly Thr Ala Asp Glu Arg Ala Pro Leu Ile Arg Thr
                325                 330                 335

<210> SEQ ID NO 3
<211> LENGTH: 24
<212> TYPE: PRT
<213> ORGANISM: Homo sapien

<400> SEQUENCE: 3

Leu Arg Glu Ile Ile Glu Ala Met Leu Lys Ala Tyr Gln Gln Lys Leu
1               5                   10                  15

Phe Val Thr His Thr Val Asp Glu
            20

<210> SEQ ID NO 4
<211> LENGTH: 151
<212> TYPE: PRT
<213> ORGANISM: Homo sapien

<400> SEQUENCE: 4

Met Gly Arg Cys Cys Phe Tyr Thr Ala Gly Thr Leu Ser Leu Leu Leu
1               5                   10                  15

Leu Val Thr Ser Val Thr Leu Leu Val Ala Arg Val Phe Gln Lys Ala
            20                  25                  30

Val Asp Gln Ser Ile Glu Lys Lys Ile Val Leu Arg Asn Gly Thr Glu
        35                  40                  45

Ala Phe Asp Ser Trp Glu Lys Pro Pro Leu Pro Val Tyr Thr Gln Phe
    50                  55                  60

Tyr Phe Phe Asn Val Thr Asn Pro Glu Glu Ile Leu Arg Gly Glu Thr
65                  70                  75                  80

Pro Arg Val Glu Glu Val Gly Pro Tyr Thr Tyr Arg Glu Leu Arg Asn
                85                  90                  95
```

-continued

```
Lys Ala Asn Ile Gln Phe Gly Asp Asn Gly Thr Thr Ile Ser Ala Val
                100                 105                 110

Ser Asn Lys Ala Tyr Val Phe Glu Arg Asp Gln Ser Val Gly Asp Pro
            115                 120                 125

Lys Ile Asp Leu Ile Arg Thr Leu Asn Ile Pro Val Leu Thr Val Ile
        130                 135                 140

Glu Trp Ser Gln Val His Phe
145                 150

<210> SEQ ID NO 5
<211> LENGTH: 8
<212> TYPE: PRT
<213> ORGANISM: Homo sapien

<400> SEQUENCE: 5

Phe Val Thr His Thr Val Asp Glu
1               5

<210> SEQ ID NO 6
<211> LENGTH: 536
<212> TYPE: PRT
<213> ORGANISM: Homo sapien

<400> SEQUENCE: 6

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly Ala Arg Pro Cys Ile Pro Lys Ser Phe
        35                  40                  45

Gly Tyr Ser Ser Val Val Cys Val Cys Asn Ala Thr Tyr Cys Asp Ser
    50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
                100                 105                 110

Lys Phe Gln Lys Val Lys Gly Phe Gly Gly Ala Met Thr Asp Ala Ala
            115                 120                 125

Ala Leu Asn Ile Leu Ala Leu Ser Pro Pro Ala Gln Asn Leu Leu Leu
        130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190

Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255
```

```
Asp Ala Tyr Ala Glu His Lys Leu Gln Phe Trp Ala Val Thr Ala Glu
            260                 265                 270

Asn Glu Pro Ser Ala Gly Leu Leu Ser Gly Tyr Pro Phe Gln Cys Leu
        275                 280                 285

Gly Phe Thr Pro Glu His Gln Arg Asp Phe Ile Ala Arg Asp Leu Gly
    290                 295                 300

Pro Thr Leu Ala Asn Ser Thr His His Asn Val Arg Leu Leu Met Leu
305                 310                 315                 320

Asp Asp Gln Arg Leu Leu Pro His Trp Ala Lys Val Val Leu Thr
                325                 330                 335

Asp Pro Glu Ala Ala Lys Tyr Val His Gly Ile Ala Val His Trp Tyr
            340                 345                 350

Leu Asp Phe Leu Ala Pro Ala Lys Ala Thr Leu Gly Glu Thr His Arg
        355                 360                 365

Leu Phe Pro Asn Thr Met Leu Phe Ala Ser Glu Ala Cys Val Gly Ser
    370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
            420                 425                 430

Val Arg Asn Phe Val Asp Ser Pro Ile Ile Val Asp Ile Thr Lys Asp
        435                 440                 445

Thr Phe Tyr Lys Gln Pro Met Phe Tyr His Leu Gly His Phe Ser Lys
    450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535

<210> SEQ ID NO 7
<211> LENGTH: 449
<212> TYPE: PRT
<213> ORGANISM: Homo sapien

<400> SEQUENCE: 7

Met Glu Leu Ser Met Gly Pro Ile Gln Ala Asn His Thr Gly Thr Gly
1               5                   10                  15

Leu Leu Leu Thr Leu Gln Pro Glu Gln Lys Phe Gln Lys Val Lys Gly
            20                  25                  30

Phe Gly Gly Ala Met Thr Asp Ala Ala Ala Leu Asn Ile Leu Ala Leu
        35                  40                  45

Ser Pro Pro Ala Gln Asn Leu Leu Leu Lys Ser Tyr Phe Ser Glu Glu
    50                  55                  60

Gly Ile Gly Tyr Asn Ile Ile Arg Val Pro Met Ala Ser Cys Asp Phe
65                  70                  75                  80
```

```
Ser Ile Arg Thr Tyr Thr Tyr Ala Asp Thr Pro Asp Asp Phe Gln Leu
                85                  90                  95

His Asn Phe Ser Leu Pro Glu Glu Asp Thr Lys Leu Lys Ile Pro Leu
            100                 105                 110

Ile His Arg Ala Leu Gln Leu Ala Gln Arg Pro Val Ser Leu Leu Ala
        115                 120                 125

Ser Pro Trp Thr Ser Pro Thr Trp Leu Lys Thr Asn Gly Ala Val Asn
130                 135                 140

Gly Lys Gly Ser Leu Lys Gly Gln Pro Gly Asp Ile Tyr His Gln Thr
145                 150                 155                 160

Trp Ala Arg Tyr Phe Val Lys Phe Leu Asp Ala Tyr Ala Glu His Lys
                165                 170                 175

Leu Gln Phe Trp Ala Val Thr Ala Glu Asn Glu Pro Ser Ala Gly Leu
            180                 185                 190

Leu Ser Gly Tyr Pro Phe Gln Cys Leu Gly Phe Thr Pro Glu His Gln
        195                 200                 205

Arg Asp Phe Ile Ala Arg Asp Leu Gly Pro Thr Leu Ala Asn Ser Thr
210                 215                 220

His His Asn Val Arg Leu Leu Met Leu Asp Asp Gln Arg Leu Leu Leu
225                 230                 235                 240

Pro His Trp Ala Lys Val Val Leu Thr Asp Pro Glu Ala Ala Lys Tyr
                245                 250                 255

Val His Gly Ile Ala Val His Trp Tyr Leu Asp Phe Leu Ala Pro Ala
            260                 265                 270

Lys Ala Thr Leu Gly Glu Thr His Arg Leu Phe Pro Asn Thr Met Leu
        275                 280                 285

Phe Ala Ser Glu Ala Cys Val Gly Ser Lys Phe Trp Glu Gln Ser Val
290                 295                 300

Arg Leu Gly Ser Trp Asp Arg Gly Met Gln Tyr Ser His Ser Ile Ile
305                 310                 315                 320

Thr Asn Leu Leu Tyr His Val Val Gly Trp Thr Asp Trp Asn Leu Ala
                325                 330                 335

Leu Asn Pro Glu Gly Gly Pro Asn Trp Val Arg Asn Phe Val Asp Ser
            340                 345                 350

Pro Ile Ile Val Asp Ile Thr Lys Asp Thr Phe Tyr Lys Gln Pro Met
        355                 360                 365

Phe Tyr His Leu Gly His Phe Ser Lys Phe Ile Pro Glu Gly Ser Gln
370                 375                 380

Arg Val Gly Leu Val Ala Ser Gln Lys Asn Asp Leu Asp Ala Val Ala
385                 390                 395                 400

Leu Met His Pro Asp Gly Ser Ala Val Val Val Leu Asn Arg Ser
                405                 410                 415

Ser Lys Asp Val Pro Leu Thr Ile Lys Asp Pro Ala Val Gly Phe Leu
            420                 425                 430

Glu Thr Ile Ser Pro Gly Tyr Ser Ile His Thr Tyr Leu Trp Arg Arg
        435                 440                 445

Gln
```

<210> SEQ ID NO 8
<211> LENGTH: 487
<212> TYPE: PRT
<213> ORGANISM: Homo sapien

```
<400> SEQUENCE: 8

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Ile Gly Tyr Asn Ile Ile Arg Val Pro
            100                 105                 110

Met Ala Ser Cys Asp Phe Ser Ile Arg Thr Tyr Thr Tyr Ala Asp Thr
        115                 120                 125

Pro Asp Asp Phe Gln Leu His Asn Phe Ser Leu Pro Glu Glu Asp Thr
130                 135                 140

Lys Leu Lys Ile Pro Leu Ile His Arg Ala Leu Gln Leu Ala Gln Arg
145                 150                 155                 160

Pro Val Ser Leu Leu Ala Ser Pro Trp Thr Ser Pro Thr Trp Leu Lys
                165                 170                 175

Thr Asn Gly Ala Val Asn Gly Lys Gly Ser Leu Lys Gly Gln Pro Gly
            180                 185                 190

Asp Ile Tyr His Gln Thr Trp Ala Arg Tyr Phe Val Lys Phe Leu Asp
        195                 200                 205

Ala Tyr Ala Glu His Lys Leu Gln Phe Trp Ala Val Thr Ala Glu Asn
210                 215                 220

Glu Pro Ser Ala Gly Leu Leu Ser Gly Tyr Pro Phe Gln Cys Leu Gly
225                 230                 235                 240

Phe Thr Pro Glu His Gln Arg Asp Phe Ile Ala Arg Asp Leu Gly Pro
                245                 250                 255

Thr Leu Ala Asn Ser Thr His His Asn Val Arg Leu Leu Met Leu Asp
            260                 265                 270

Asp Gln Arg Leu Leu Leu Pro His Trp Ala Lys Val Val Leu Thr Asp
        275                 280                 285

Pro Glu Ala Ala Lys Tyr Val His Gly Ile Ala Val His Trp Tyr Leu
290                 295                 300

Asp Phe Leu Ala Pro Ala Lys Ala Thr Leu Gly Glu Thr His Arg Leu
305                 310                 315                 320

Phe Pro Asn Thr Met Leu Phe Ala Ser Glu Ala Cys Val Gly Ser Lys
                325                 330                 335

Phe Trp Glu Gln Ser Val Arg Leu Gly Ser Trp Asp Arg Gly Met Gln
            340                 345                 350

Tyr Ser His Ser Ile Ile Thr Asn Leu Leu Tyr His Val Val Gly Trp
        355                 360                 365

Thr Asp Trp Asn Leu Ala Leu Asn Pro Glu Gly Gly Pro Asn Trp Val
370                 375                 380

Arg Asn Phe Val Asp Ser Pro Ile Ile Val Asp Ile Thr Lys Asp Thr
385                 390                 395                 400

Phe Tyr Lys Gln Pro Met Phe Tyr His Leu Gly His Phe Ser Lys Phe
                405                 410                 415
```

Ile Pro Glu Gly Ser Gln Arg Val Gly Leu Val Ala Ser Gln Lys Asn
            420                 425                 430

Asp Leu Asp Ala Val Ala Leu Met His Pro Asp Gly Ser Ala Val Val
        435                 440                 445

Val Val Leu Asn Arg Ser Ser Lys Asp Val Pro Leu Thr Ile Lys Asp
    450                 455                 460

Pro Ala Val Gly Phe Leu Glu Thr Ile Ser Pro Gly Tyr Ser Ile His
465                 470                 475                 480

Thr Tyr Leu Trp Arg Arg Gln
                485

<210> SEQ ID NO 9
<211> LENGTH: 24
<212> TYPE: PRT
<213> ORGANISM: Artificial
<220> FEATURE:
<223> OTHER INFORMATION: Variant sequence of Homo sapiens Helix 5 of
      LIMP-2 protein

<400> SEQUENCE: 9

Leu Arg Glu Asp Asp Glu Ala Met Asp Lys Ala Tyr Gln Gln Lys Leu
1               5                   10                  15

Phe Val Thr His Thr Val Asp Glu
            20

<210> SEQ ID NO 10
<211> LENGTH: 40
<212> TYPE: PRT
<213> ORGANISM: Artificial
<220> FEATURE:
<223> OTHER INFORMATION: Variant sequence of Homo sapiens Helix 5 of
      LIMP-2 protein including TAT peptide of HIV-1

<400> SEQUENCE: 10

Lys Phe Glu Arg Gln Leu Arg Glu Ile Ile Glu Ala Met Leu Lys Ala
1               5                   10                  15

Tyr Gln Gln Lys Leu Phe Val Thr His Thr Val Asp Glu Tyr Gly Arg
            20                  25                  30

Lys Lys Arg Arg Gln Arg Arg Arg
            35                  40

<210> SEQ ID NO 11
<211> LENGTH: 40
<212> TYPE: PRT
<213> ORGANISM: Artificial
<220> FEATURE:
<223> OTHER INFORMATION: Variant sequence of Homo sapiens Helix 5 of
      LIMP-2 protein including TAT peptide of HIV-1

<400> SEQUENCE: 11

Lys Phe Glu Arg Gln Leu Arg Glu Asp Asp Glu Ala Met Asp Lys Ala
1               5                   10                  15

Tyr Gln Gln Lys Leu Phe Val Thr His Thr Val Asp Glu Tyr Gly Arg
            20                  25                  30

Lys Lys Arg Arg Gln Arg Arg Arg
            35                  40

<210> SEQ ID NO 12
<211> LENGTH: 24
<212> TYPE: PRT
<213> ORGANISM: Artificial

<220> FEATURE:
<223> OTHER INFORMATION: Variant of Homo sapiens ADAM17 Conserved
      ADAM-seventeeN Dynamic Interaction Sequence (CANDIS) domain

<400> SEQUENCE: 12

Lys Arg Val Gln Asp Val Ile Glu Arg Phe Trp Asp Phe Ile Asp Gln
1               5                   10                  15

Leu Ser Ile Asn Thr Phe Gly Lys
            20

<210> SEQ ID NO 13
<211> LENGTH: 61
<212> TYPE: PRT
<213> ORGANISM: Homo sapiens

<400> SEQUENCE: 13

Phe Gly Gly Ala Met Thr Asp Ala Ala Ala Leu Asn Ile Leu Ala Leu
1               5                   10                  15

Ser Pro Pro Ala Gln Asn Leu Leu Leu Lys Ser Tyr Phe Ser Glu Glu
            20                  25                  30

Gly Ile Gly Asn Phe Ser Leu Pro Glu Glu Asp Thr Lys Leu Lys Ile
        35                  40                  45

Pro Leu Ile His Arg Ala Leu Gln Leu Ala Gln Arg Pro
    50                  55                  60

<210> SEQ ID NO 14
<211> LENGTH: 61
<212> TYPE: PRT
<213> ORGANISM: Pan troglodytes

<400> SEQUENCE: 14

Phe Gly Gly Ala Met Thr Asp Ala Ala Ala Leu Asn Ile Leu Ala Leu
1               5                   10                  15

Ser Pro Pro Ala Gln Asn Leu Leu Leu Lys Ser Tyr Phe Ser Glu Glu
            20                  25                  30

Gly Ile Gly Asn Phe Ser Leu Pro Glu Glu Asp Thr Lys Leu Lys Ile
        35                  40                  45

Pro Leu Ile His Arg Ala Leu Gln Leu Ala Gln Arg Pro
    50                  55                  60

<210> SEQ ID NO 15
<211> LENGTH: 61
<212> TYPE: PRT
<213> ORGANISM: Rattus norvegicus

<400> SEQUENCE: 15

Phe Gly Gly Ala Met Thr Asp Ala Thr Ala Leu Asn Ile Leu Ala Leu
1               5                   10                  15

Ser Pro Pro Ala Gln Lys Leu Leu Leu Lys Ser Tyr Phe Ser Ser Glu
            20                  25                  30

Gly Ile Glu Asn Phe Ser Leu Pro Glu Glu Asp Thr Lys Leu Lys Ile
        35                  40                  45

Pro Leu Ile His Arg Ala Leu Lys Met Ser Pro Arg Pro
    50                  55                  60

<210> SEQ ID NO 16
<211> LENGTH: 61
<212> TYPE: PRT
<213> ORGANISM: Mus musculus

```
<400> SEQUENCE: 16

Phe Gly Gly Ala Met Thr Asp Ala Thr Ala Leu Asn Ile Leu Ala Leu
1               5                   10                  15

Ser Pro Pro Thr Gln Lys Leu Leu Arg Ser Tyr Phe Ser Thr Asn
            20                  25                  30

Gly Ile Glu Asn Phe Ser Leu Pro Glu Glu Asp Thr Lys Leu Lys Ile
            35                  40                  45

Pro Leu Ile His Gln Ala Leu Lys Met Ser Ser Arg Pro
        50                  55                  60

<210> SEQ ID NO 17
<211> LENGTH: 61
<212> TYPE: PRT
<213> ORGANISM: Sus domesticus

<400> SEQUENCE: 17

Phe Gly Gly Ala Met Thr Asp Ala Ala Ala Leu Asn Ile Leu Ala Leu
1               5                   10                  15

Ser Pro Gln Ala Arg Asn Leu Leu Lys Ser Tyr Phe Ser Glu Glu
            20                  25                  30

Gly Ile Glu Asn Phe Ser Leu Pro Glu Glu Asp Val Lys Leu Lys Ile
            35                  40                  45

Pro Leu Ile His Gln Ala Leu Lys Met Ala Gln Arg Pro
        50                  55                  60

<210> SEQ ID NO 18
<211> LENGTH: 44
<212> TYPE: PRT
<213> ORGANISM: Homo sapiens

<400> SEQUENCE: 18

Gln Val His Phe Leu Arg Glu Ile Ile Glu Ala Met Leu Lys Ala Tyr
1               5                   10                  15

Gln Gln Lys Leu Phe Val Thr His Thr Val Asp Glu Leu Leu Trp Gly
            20                  25                  30

Tyr Lys Asp Glu Ile Leu Ser Leu Ile His Val Phe
            35                  40

<210> SEQ ID NO 19
<211> LENGTH: 44
<212> TYPE: PRT
<213> ORGANISM: Mus musculus

<400> SEQUENCE: 19

Gln Leu Thr Leu Leu Arg Glu Leu Ile Glu Ala Met Leu Lys Ala Tyr
1               5                   10                  15

Gln Gln Lys Leu Phe Val Ile His Thr Val His Glu Leu Leu Trp Gly
            20                  25                  30

Tyr Lys Asp Glu Ile Leu Ser Leu Val His Ile Phe
            35                  40

<210> SEQ ID NO 20
<211> LENGTH: 10
<212> TYPE: PRT
<213> ORGANISM: Homo sapien

<400> SEQUENCE: 20

Glu Gln Lys Leu Ile Ser Glu Glu Asp Leu
1               5                   10
```

```
<210> SEQ ID NO 21
<211> LENGTH: 11
<212> TYPE: PRT
<213> ORGANISM: Human immunodeficiency virus type 1

<400> SEQUENCE: 21

Tyr Gly Arg Lys Lys Arg Arg Gln Arg Arg Arg
1               5                   10

<210> SEQ ID NO 22
<211> LENGTH: 6
<212> TYPE: PRT
<213> ORGANISM: Homo sapiens

<400> SEQUENCE: 22

Lys Phe Glu Arg Gln Leu
1               5
```

LYSOSOME MEMBRANE PROTEIN 2 (LIMP-2) BASED PEPTIDES AND RELATED USES

CROSS-REFERENCED TO RELATED PATENT APPLICATIONS

The present application claims the benefit of priority under 35 U.S.C. § 119(e) to U.S. Provisional Application No. 62/307,179, filed on Mar. 11, 2016, the contents of which are incorporated herein by reference in their entireties.

BACKGROUND

The field of the invention relates to LIMP-2 based peptides and related uses. The disclosed peptides may be utilized to prepare pharmaceutical compositions for treating and/or preventing diseases and infections, and the disclosed peptides may be used in biotechnological methods.

The activity of the lysosomal enzyme glucocerebrosidase (GCase) is important in the pathogenesis of various diseases and disorders such as Parkinson's disease and Gaucher's disease. Reduced GCase activity has been found in genetic and sporadic forms of Parkinson's disease and increasing the activity of GCase has potential for treatment of Parkinson's disease, Gaucher's disease, and other related disorders associated with decreased GCase activity. We have identified a critical protein, LIMP-2 that facilitates transport of GCase to lysosomes. We have also identified a part of LIMP-2 including a small peptide sufficient to bind and activate GCase. The identified peptide or peptidomimetic variants thereof may be utilized to activate recombinant and cellular GCase. Using the identified peptide or peptidomimetic variants thereof, we will also be able to purify larger amounts of GCase to treat Parkinson's disease, Gaucher's disease, and other related disorders associated with decreased GCase activity. Finally, using the identified peptide or peptidomimetic variants thereof, we propose screening assays that may be utilized to identify small molecules that interact with GCase and/or activate GCase.

SUMMARY

Disclosed are LIMP-2 peptides, LIMP-2 polypeptides, variants thereof, and pharmaceutical compositions comprising the LIMP-2 peptides, LIMP-2 polypeptides, or variants thereof. The disclosed peptides and polypeptides preferably comprise an amino acid sequence that is sufficient for providing a biological activity associated with LIMP-2, which may include binding and/or activating biological molecules such as β-glucocerebrosidase and binding viral proteins such as viral proteins of enterovirus 71 (E71) and coxsackievirus A16 (CA16) (e.g., VP1 of E71 or CA16). Also disclosed are methods of using the LIMP-2 peptides, LIMP-2 polypeptides, and variants thereof Disclosed are isolated LIMP-2 peptides comprising, consisting essentially of, or consisting of the amino acid sequence of any of SEQ ID NOs:1-3 or an amino acid sequence having a least about 80% sequence identity to any of SEQ ID NOs:1-3 (i.e., a variant thereof). In particular, SEQ ID NO: 1 provides the amino acid sequence of lysosome membrane protein 2 (LIMP-2) isoform 1 precursor (as listed by NCBI Reference Sequence: NP_005497.1, accessed on Mar. 10, 2016, the content of which is incorporate herein by reference in its entirety). SEQ ID NO:3 provides the amino sequence from amino acids 152-175 of lysosome membrane protein 2 (LIMP-2) isoform 1 precursor. For completeness, SEQ ID NO:2 provides the amino acid sequence of lysosome membrane protein 2 (LIMP-2) isoform 1 precursor (as listed by NCBI Reference Sequence: NP_001191184.1, accessed on Mar. 10, 2016, the content of which is incorporate herein by reference in its entirety). LIMP-2 isoform 2 precursor does not comprise the amino acid sequence from amino acids 93-236 of LIMP-2 isoform 1 precursor.

The disclosed LIMP-2 peptides may comprise or consist of a contiguous amino acid sequence of LIMP-2. Optionally, the peptides may have an amino acid length of less than about 100, 95, 90, 85, 80, 75, 70, 65, 60, 55, 50, 45, 40, 35, 30, 25, 20, 15, or 10 amino acids or the peptides may have an amino acid length within a range bounded by any two values selected from 100, 95, 90, 85, 80, 75, 70, 65, 60, 55, 50, 45, 40, 35, 30, 25, 20, 15, or 10 amino acids (e.g., an amino acid length of 10-50 amino acids).

Optionally, the disclosed LIMP-2 peptides do not comprise, consist essentially of, or consist of the amino acid sequence of SEQ ID NO:4, which provides the sequence of amino acids 1-151 of LIMP-2 isoform 1 precursor. Optionally, the isolated peptides do not comprise amino acids 150 and 151 of LIMP-2 isoform 1 precursor. Optionally, the isolated peptides comprise amino acid 168 of LIMP-2 isoform 1 precursor. Optionally, the isolated peptide comprises an amino acid sequence comprising two or more contiguous amino acids of SEQ ID NO:5, which provides the sequence of amino acids 168-175 of LIMP-2 isoform 1 precursor.

The disclosed LIMP-2 peptides may include non-naturally occurring modifications. Optionally, the isolated peptides comprise a non-naturally occurring N-terminal methionine residue. Optionally, the disclosed peptides comprise one or more amino acid modifications selected from the group consisting of acylation (e.g., N-terminal acylation), acetylation (e.g., N-terminal acetylation), formylation, lipolylation, myristoylation, palmitoylation, alkylation, isoprenylation, prenylation, pegylation, and amidation (e.g., C-terminal amidation).

Also disclosed are isolated polypeptides comprising the disclosed LIMP-2 peptides. The isolated polypeptides may comprise: (i) the disclosed LIMP-2 peptides (or variants thereof) optionally fused at the N-terminus or C-terminus to one or more of (ii) a cell-penetrating protein motif and (iii) a chaperone-mediated autophagy (CMA) targeting motif.

The disclosed LIMP-2 peptides and polypeptides differ from naturally occurring LIMP-2. The LIMP-2 peptides and polypeptides may comprise, consist essentially of, or consist of a fragment of LIMP-2 or a variant thereof.

The disclosed LIMP-2 peptides and polypeptides may lack amino acid modifications present on naturally occurring LIMP-2. Optionally, the isolated peptides or isolated polypeptides do not comprise N-linked glycosylation and/or O-linked glycosylation.

The disclosed LIMP-2 peptides and polypeptides preferably exhibit one or more biological activities associated with LIMP-2. The disclosed peptides and polypeptides may comprise an amino acid sequence that is sufficient for the one or more biological activities of LIMP-2. The biological activity of the peptides and polypeptides may include binding to β-glucocerebrosidase (preferably with a $K_d$ of less than about $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M or lower). Preferably, the biological activity of the peptides and polypeptides includes increasing biological activity of β-glucocerebrosidase, which includes hydrolysis of glycosylceramide (i.e., glycosylceramidase activity). Preferably, the peptides and polypeptides bind to β-glucocerebrosidase and increase the glycosylceramidase activity of β-glucocerebrosidase by at least about 10%, 20%, 30%, 40%, 50%, 60%, 70%, 80%, 90%, 100%, or higher.

The biological activity of the LIMP-2 peptides and polypeptides may include binding to a virus, including, but not limited to, enteroviruses such as E71. The LIMP-2 peptides and polypeptides may bind to the VP1 protein of E71 or CA16 (preferably with a $K_d$ of less than about $10^{-5}$ M, $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M, $10^{-15}$ M or lower).

Also disclosed are pharmaceutical compositions comprising the disclosed LIMP-2 peptides and disclosed polypeptides together with a pharmaceutically acceptable carrier, excipient, or diluent. The disclosed pharmaceutical compositions may comprise an effective amount of the disclosed peptides and/or disclosed peptides for binding to β-glucocerebrosidase, and preferably, increasing biological activity of β-glucocerebrosidase including hydrolysis of glycosylceramide by at least about 10%, 20%, 30%, 40%, 50%, 60%, 70%, 80%, 90%, 100%, or higher. The disclosed pharmaceutical compositions may comprise an effective amount of the disclosed peptides and/or disclosed polypeptides for binding to a virus, including, but not limited to, enteroviruses such as E71 (e.g., at VP1).

Also disclosed are methods for treating a disease or disorder, including, but not limited to, diseases and disorders associated with the biological activity of β-glucocerebrosidase (e.g., diseases and disorders associated with decreased biological activity of β-glucocerebrosidase). The methods may include administering the pharmaceutical compositions disclosed herein to a subject in need thereof. Diseases and disorders may include, but are not limited to Gaucher disease. Disease and disorders may include synucleinopathies, including but not limited to Parkinson's disease and dementia with Lewy bodies. The diseases and disorders may be associated with genetic mutations, for example, genetic mutations in SCARB2 and/or GBA1.

Also disclosed are methods for treating or preventing infection by a virus in a subject in need thereof. The methods may include administering the disclosed pharmaceutical compositions to a subject infected by, or at risk for infection by a virus, where optionally the virus is an enterovirus such as E71.

Also disclosed are methods for activating β-glucocerebrosidase. The methods may include contacting the β-glucocerebrosidase with the disclosed LIMP-2 peptides and/or the disclosed polypeptides. The activated β-glucocerebrosidase may be used in methods for preparing a pharmaceutical composition, the methods comprising combining the activated β-glucocerebrosidase with a pharmaceutically acceptable carrier, excipient, or diluent.

The disclosed LIMP-2 peptides and/or polypeptides may be used in methods for purifying β-glucocerebrosidase from a composition or solution comprising β-glucocerebrosidase (e.g., a cell lysate or a solution comprising recombinant β-glucocerebrosidase). The methods may include: (i) contacting a solution comprising β-glucocerebrosidase with a solid or semi-solid substrate comprising the disclosed peptides and/or disclosed polypeptides immobilized on a solid or semi-solid substrate (e.g., via the isolated peptide or isolated polypeptide being covalently bonded to the solid or semi-solid substrate either directly or indirectly via a chemical linker, or via the isolated peptide or isolated polypeptide being non-covalently bonded to the solid or semi-solid substrate), where the solid or semi-solid substrate binds the β-glucocerebrosidase to form a complex; and (ii) washing the complex with a washing solution to remove components other than β-glucocerebrosidase from the complex. Optionally, the methods further may include: (iii) washing the complex with an elution buffer to remove the bound β-glucocerebrosidase.

The disclosed LIMP-2 peptides and/or polypeptides may be utilized to identify a compound that binds to β-glucocerebrosidase and preferably activates β-glucocerebrosidase, such as a small molecule compound. The methods for identifying a compound that binds to β-glucocerebrosidase and preferably activates β-glucocerebrosidase may include: (i) combining: (a) β-glucocerebrosidase, (b) any of the disclosed peptides and/or polypeptides, and (c) the compound in a solution; and (ii) determining whether the compound prevents binding (i.e., complex formation) and/or activation between (a) the β-glucocerebrosidase and (b) the isolated peptide or isolated polypeptide. The methods may be devised as high-throughput methods. In the disclosed methods, the β-glucocerebrosidase may include a detectable label and/or the peptide or polypeptide may include a detectable label, for example, in order to facilitate detecting binding between β-glucocerebrosidase and the peptide or polypeptide.

Also disclosed are isolated polynucleotides encoding the presently disclosed LIMP-2 peptides and polypeptides. The isolated polynucleotides may be present in an expression vector comprising the isolated polynucleotides operably linked to a promoter. The expression vector may be present in an isolated cell (i.e., a recombinant cell transfected or transformed with the expression vector.

DETAILED DESCRIPTION

Figure 1:
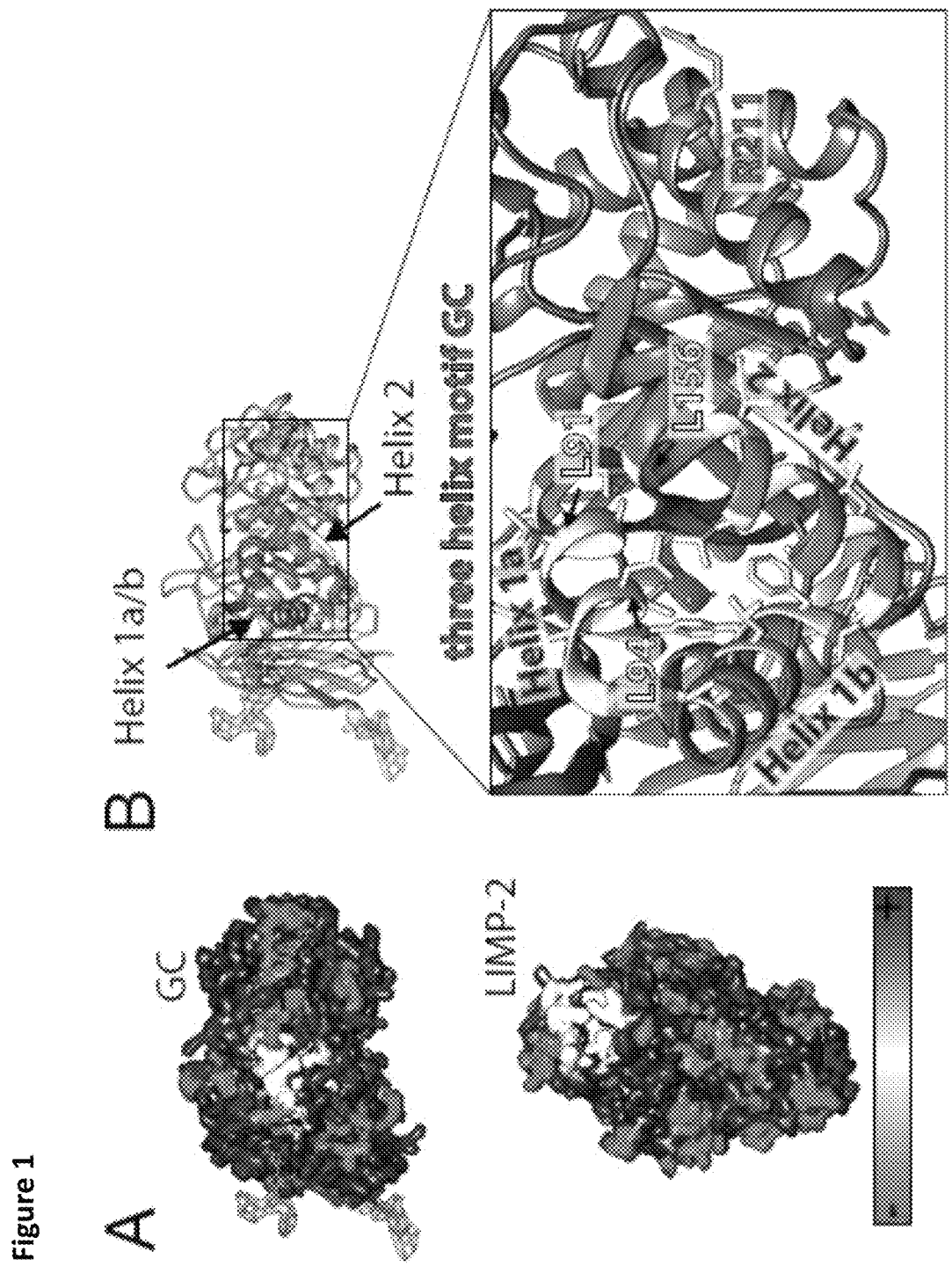
FIG. 1: Identification of the LIMP-2 interaction site in GC by structural and molecular analyses. A) Illustration of surface charges in LIMP-2 (PDB: 4F7B) and GC (PDB: 2J25); in white: hydrophobic areas. B) Protein structure of GC (PDB: 2J25) with hydrophobic patch shown in red revealing three helices: helix 1a, helix 1b and helix 2. Magnification of the helical region with hydrophobic amino acids indicated in yellow. C) Sequence alignment of multiple GC species (red boxes: helix1a/b and 2; in yellow: hydrophobic residues). D) Co-immunoprecipitation (co-IP) of overexpressed GC helix mutants L91E, L94E and L156E, wild-type (WT) and control R211E mutant in N2a cells using a LIMP-2—(IP) and a human GC-specific antibody (α-hGC) (# identifies antibody bands; AB ctrl=antibody control). Dotted line indicates different exposure times of the same immunoblot. E) Densitometric quantification of bound GC protein normalized to precipitated LIMP-2 (n=4-12). F) Immunofluorescence of GC-deficient cells transfected with the GC helical motif mutants (L91E, L94E and L156E) and control R211E mutant (α-hGC; red), co-stained for endogenous LIMP-2 (green). Area of magnification is outlined by a white box. G) Co-localization of GC and LIMP-2 was determined using the Pearson's index (n=4-10). H) Immunoblot and I) densitometric quantification (postER/ER ratio normalized to WT GC (n=2-3)) of EndoH or PNGaseF treated cell extracts of GC-deficient cells expressing GC mutants L91E, L94E and L156E and WT GC (α-hGC) with or without myc-tagged LIMP-2 (α-myc). Actin was used as loading control. EndoH resistance of proteins indicates their post ER localization. Dotted lines separate individual blots. See also FIG. 4.
Figure 1:
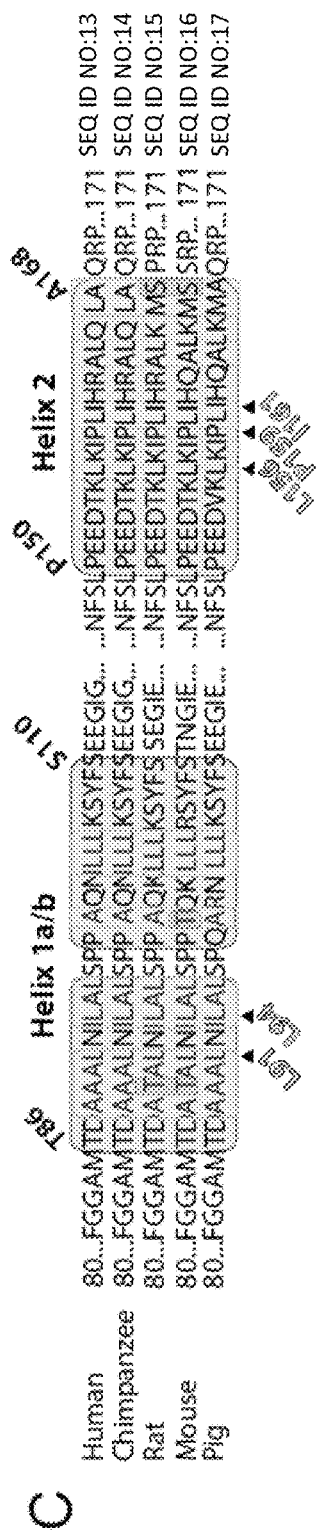
Figure 1:
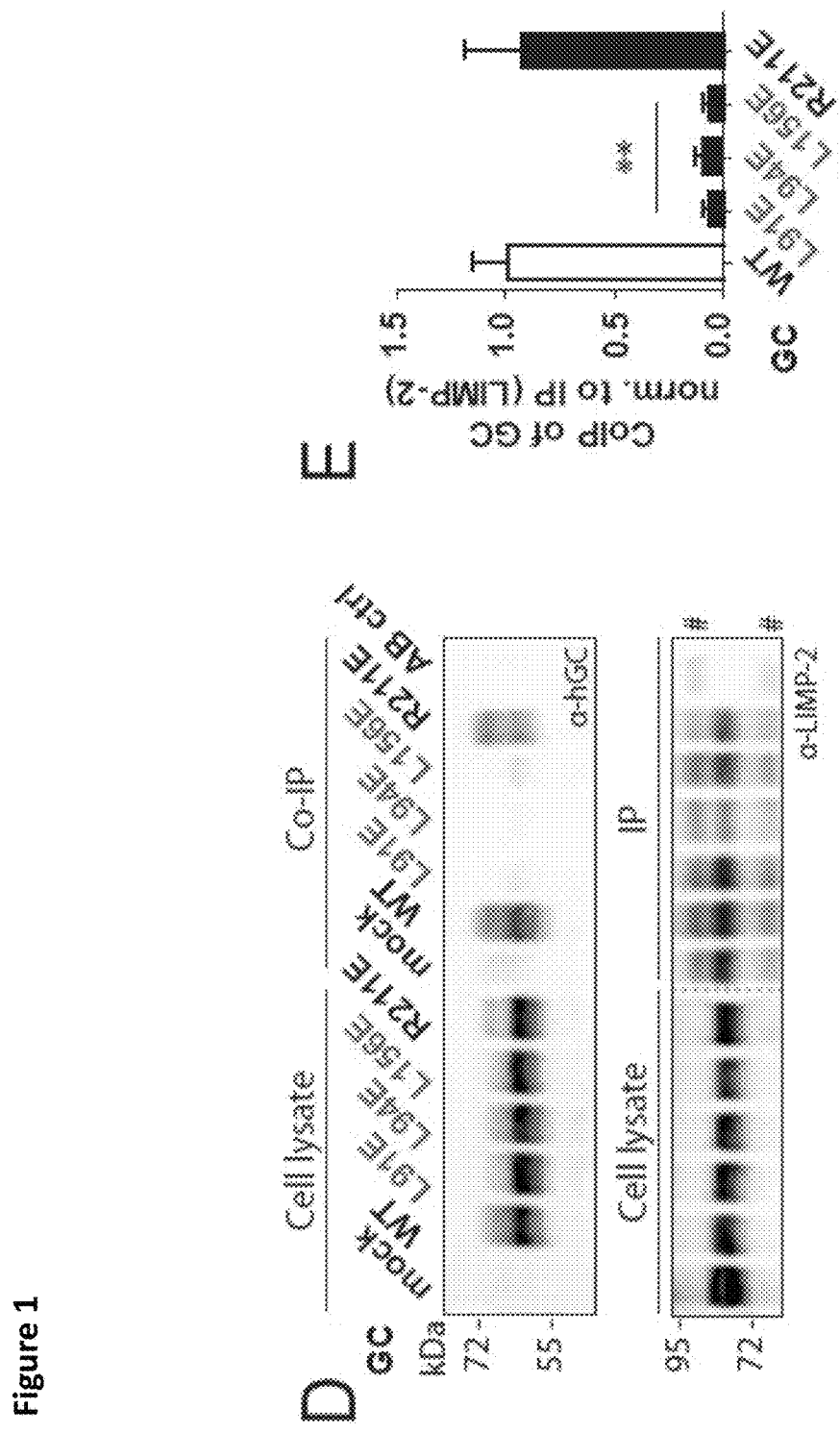
Figure 1:
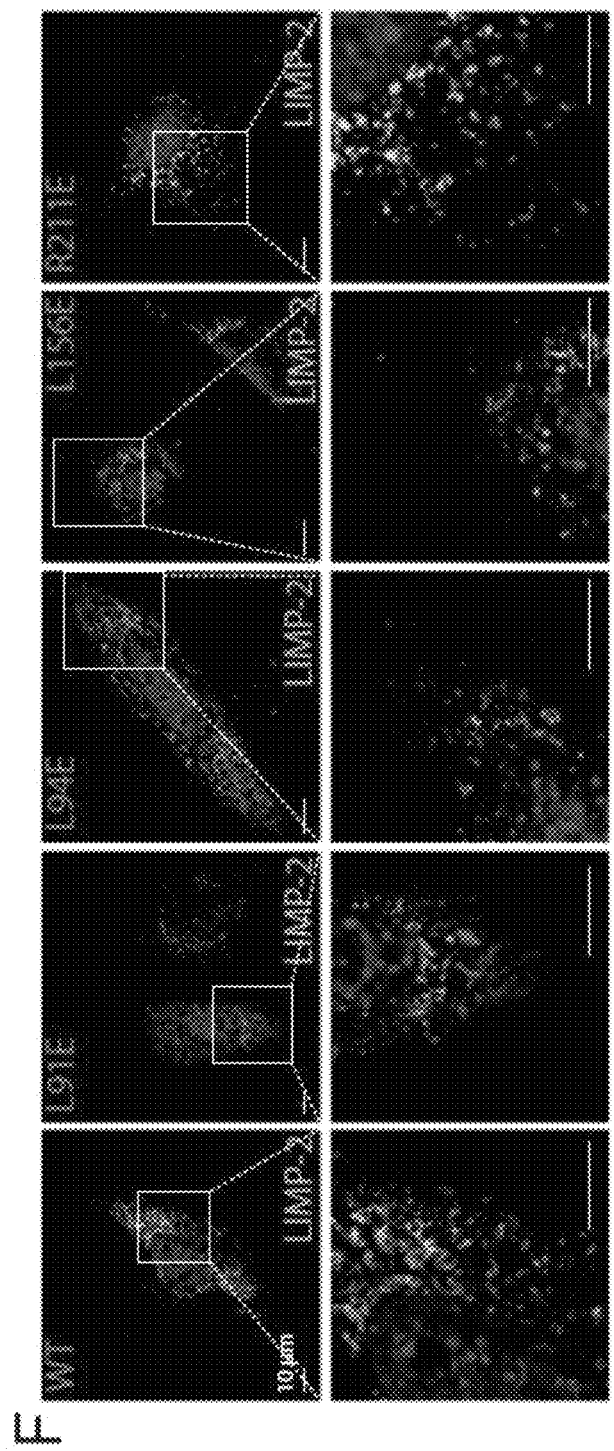
Figure 1:
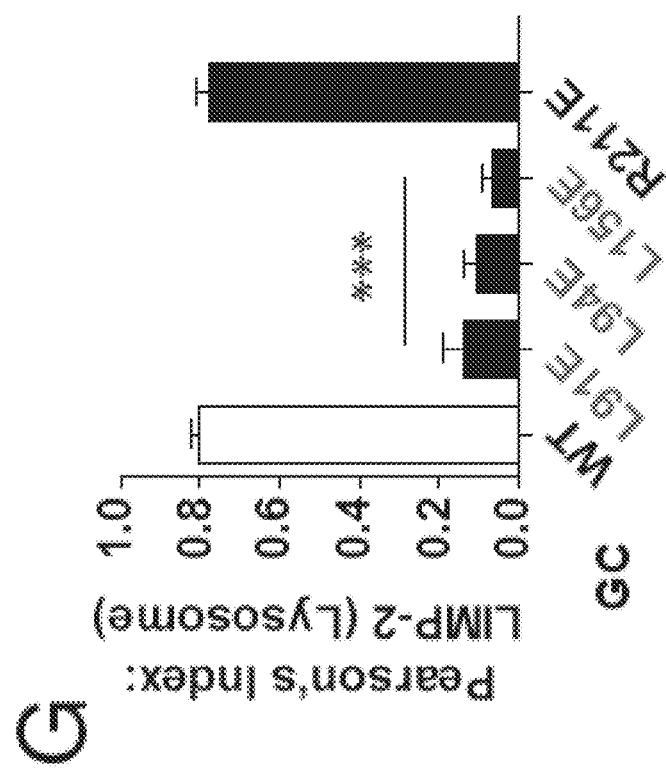
Figure 1:
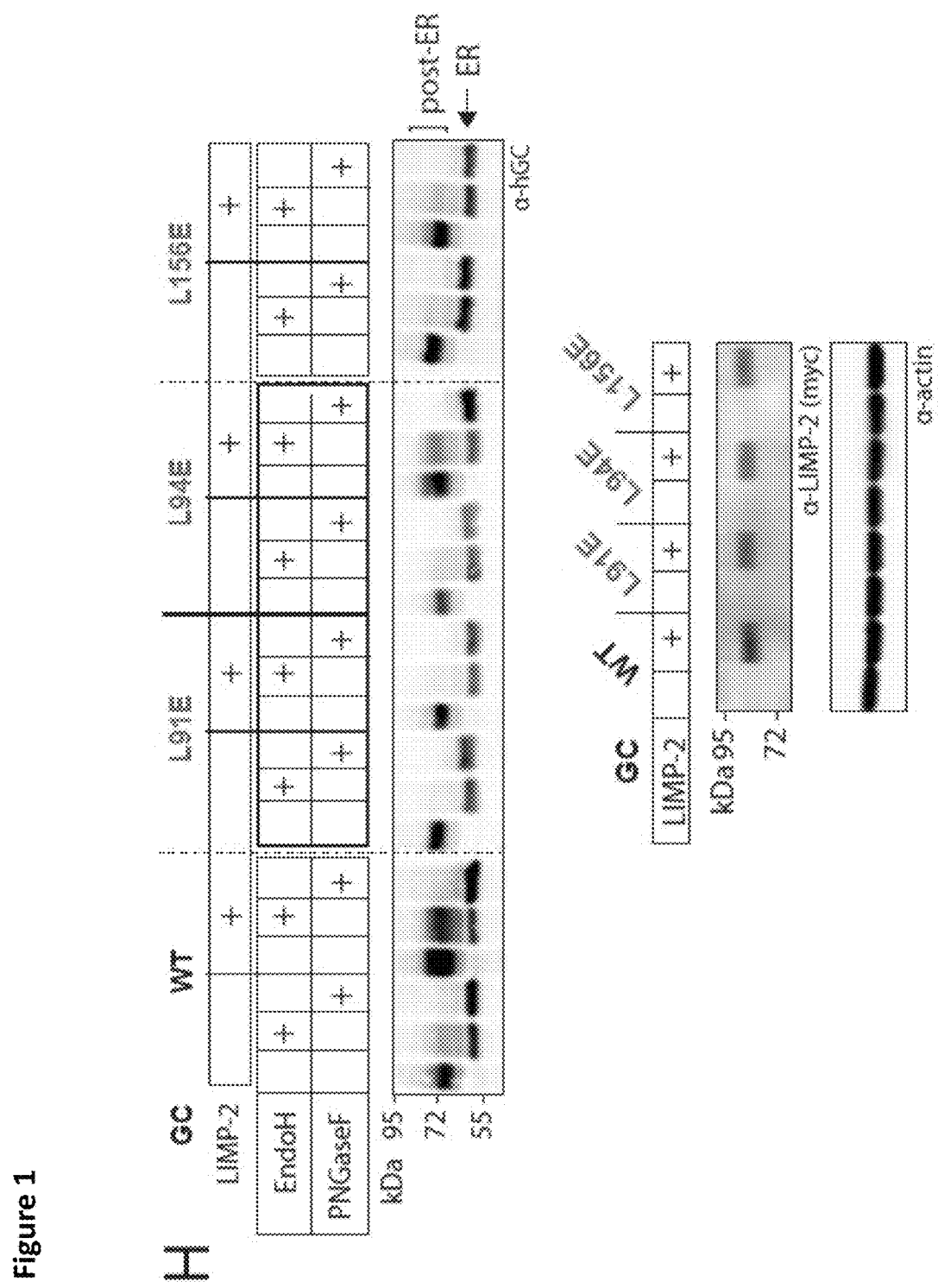
Figure 1:
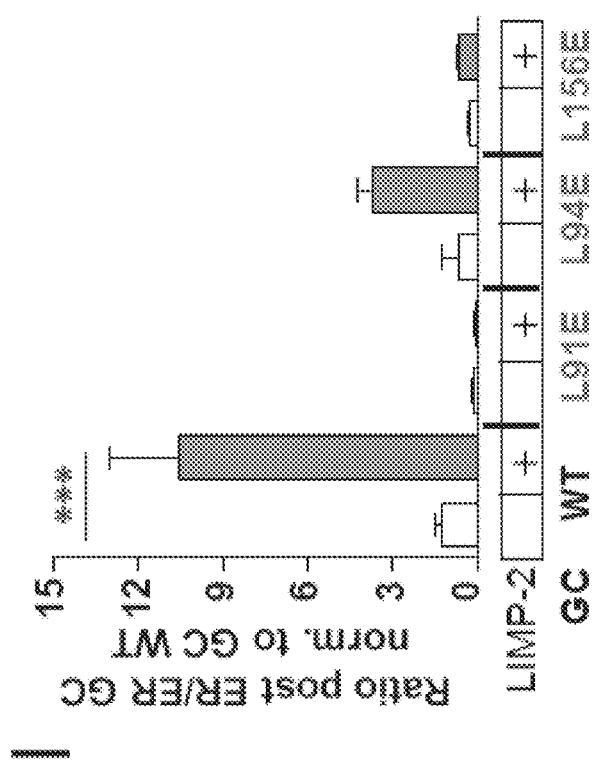

The present invention is described herein using several definitions, as set forth below and throughout the application.

Definitions

Unless otherwise specified or indicated by context, the terms "a", "an", and "the" mean "one or more." For example, "a peptide" or "a polypeptide" should be interpreted to mean "one or more peptides" or "one or more polypeptides," respectively.

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, a "subject" may be interchangeable with "patient" or "individual" and means an animal, which may be a human or non-human animal, in need of treatment. Non-human animals may include dogs, cats, horses, cows, pigs, sheep, and the like.

A "subject in need thereof" may include a patient having a disease, disorder, or condition that is characterized by the lack of, or by deficient β-glucocerebrosidase activity. Diseases and disorders may include Gaucher's disease. Diseases and disorders may include synucleinopathies, including but not limited to Parkinson's disease and dementia with Lewy bodies. Diseases and disorders may include diseases and disorders associated with genetic mutations, for example, diseases and disorders associated with genetic mutations in SCARB2 and/or GBA1

A "subject in need thereof" may include a subject infected by, or at risk for infection by a virus that utilizes LIMP-2 as a receptor, for example, enterovirus 71 (E71). (See Yamayoshi et al., "Receptors for enterovirus 71," Emerging Microbes and Infections (2014)3,e53; and Chen et al., "Molecular Determinants of Enterovirus 71 Viral Entry," J. Biol. Chem., Vol. 287, No. 9, pp. 6406-6420; the contents of which are incorporated herein by reference in their entireties).

Reference is made herein to LIMP-2. LIMP-2 or "lysosome membrane protein 2" is a protein in humans encoded by the SCARB2 gene. LIMP-2 is known to exist in isoforms, including isoform 1 (see SEQ ID NO:1) and isoform 2 (see SEQ ID NO:3).

Reference is made herein to β-glucocerebrosidase. β-glucocerebrosidase (also called glucosylceramidase, acid β-glucosidase, D-glucosyl-N-acylsphingosine glucohydrolase, or GCase) is an enzyme with glucosylceramidase activity (EC 3.2.1.45) that is needed to cleave, by hydrolysis, the beta-glucosidic linkage of the chemical glucocerebroside, an intermediate in glycolipid metabolism. β-Glucocerebrosidase is localized in the lysosome and has a molecular weight of 59700 Daltons. β-glucocerebrosidase is known to exist in isoforms, including isoform 1 (see SEQ ID NO:6), isoform 2 (see SEQ ID NO:7), and isoform 3 (see SEQ ID NO:8).

Reference is made herein to LIMP-2 peptides, polypeptides and pharmaceutical compositions comprising LIMP-2 peptides and polypeptides. Exemplary LIMP-2 peptides and polypeptides may comprise, consist essentially of, or consist of the amino acid sequence of any of SEQ ID NOs:1-3, or variants of the LIMP-2 peptides and polypeptides may comprise, consist essentially of, or consist of an amino acid sequence having at least about 80%, 90%, 95%, 96%, 97%, 98%, or 99% sequence identity to any of SEQ ID NOs:1-3. Variant LIMP-2 peptides polypeptides may include peptides or polypeptides having one or more amino acid substitutions, deletions, additions and/or amino acid insertions relative to a reference peptide or polypeptide. Also disclosed are nucleic acid molecules that encode the disclosed LIMP-2 peptides and polypeptides (e.g., polynucleotides that encode the peptides or polypeptide of any of SEQ ID NOs: 1-3 and variants thereof).

The disclosed LIMP-2 peptides, polypeptides, and variants thereof, preferably exhibit one or more biological activities associated with LIMP-2. Biological activities may include, but are not limited to β-glucocerebrosidase activity. Biological activities may include, but are not limited to binding to VP1 of E71.

The disclosed polynucleotides encoding the disclosed LIMP-2 peptides and polypeptides may be present in a replication vector and/or expression vector. Suitable vectors may include bacterial, plant, fungal, insect, or animal host cell replication and/or expression vectors that express the disclosed peptides, polypeptides, and variants thereof. Vectors may be used to transform appropriate host cells (e.g., *E. coli*). The transformed host cell may be cultivated or fermented such that the peptide or polypeptide is expressed constitutively or after adding a reagent that induces expression (e.g., via an inducible promoter). Expression vectors as contemplated herein may include control sequences that modulate expression of the encoded polypeptide. Expression control sequences may include constitutive or inducible promoters (e.g., T3, T7, Lac, trp, or phoA), ribosome binding sites, or transcription terminators.

The vectors disclosed herein may be utilized to transform host cells. Suitable host cells include bacterial, plant, fungal, insect, or animal host cell. Suitable bacteria include, but are not limited to: Gram-negative bacteria such as *Escherichia* species (e.g., *E. coli*), other Gram-negative bacteria, (e.g., *Pseudomonas* sp., such as *Pseudomonas aeruginosa*, or *Caulobacter* sp., such as *Caulobacter crescentus*), or Gram-positive bacteria (e.g., *Bacillus* sp., in particular *Bacillus subtlis*). Suitable fungal cells may include yeast (e.g., *Saccharomyces cerevisiae*).

Also disclosed are methods for expressing, preparing, isolating, separating, or purifying the disclosed LIMP-2 peptides, polypeptides, and variants thereof. In some embodiments, the methods may be utilized to produce the peptides, polypeptides, and variants thereof as disclosed herein. The steps of the methods may include: (i) cultivating or fermenting a transformed host cell (e.g., a bacterial host cell as contemplated herein) which comprises an expression vector (as contemplated herein) which in turn comprises a nucleic acid molecule encoding the disclosed peptides, polypeptides, or variants thereof (as contemplated herein), wherein cultivation occurs under conditions which cause expression of the peptides, polypeptides, or variants; and (ii) isolating, separating, or purifying the peptides, polypeptides, or variants. The transformed bacteria may be cultivated or fermented using methods known in the art in order to express the peptides, polypeptides, or variants. An exemplary isolation, separation, or purification method may include one or more of the following steps: a cell disruption step, a clarification step (e.g., via centrifugation or filtration), a chromatographic separation step, a dialysis step, and a precipitation step.

The terms "nucleic acid" and "nucleic acid sequence" refer to a nucleotide, oligonucleotide, polynucleotide (which terms may be used interchangeably), or any fragment thereof. These phrases also refer to DNA or RNA of genomic or synthetic origin (which may be single-stranded or double-stranded and may represent the sense or the antisense strand).

The terms "amino acid" and "amino acid sequence" refer to an oligopeptide, peptide, polypeptide, or protein sequence (which terms may be used interchangeably), or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

The amino acid sequences contemplated herein may include conservative amino acid substitutions relative to a reference amino acid sequence. For example, a variant LIMP-2 peptide or polypeptide may include conservative amino acid substitutions relative to a reference peptide or polypeptide. "Conservative amino acid substitutions" are those substitutions that are predicted to interfere least with the properties of the reference polypeptide. In other words, conservative amino acid substitutions substantially conserve the structure and the function of the reference protein. Conservative amino acid substitutions generally maintain (a) the structure of the peptide or polypeptide backbone in the area of the substitution, for example, as a beta sheet or alpha helical conformation, (b) the charge or hydrophobicity of the molecule at the site of the substitution, and/or (c) the bulk of the side chain. The following table provides a list of exemplary conservative amino acid substitutions:

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Glu, Gln |
| Met | Leu, Ile |
| Phe | His, Met, Leu, Trp,Tyr |
| Ser | Cys, Thr |
| Thr | Ser, Val |
| Trp | Phe, Tyr |
| Tyr | His, Phe, Trp |
| Val | Ile, Leu, Thr |

Also contemplated herein are peptidomimetics of the disclosed peptides. As disclosed herein, a peptidomimetic is a peptide equivalent characterized as retaining the polarity, three dimensional size and functionality (bioactivity) of its peptide equivalent but where the peptide bonds have been replaced (e.g., by more stable linkages which are more resistant to enzymatic degradation by hydrolytic enzymes). Generally, the bond which replaces the amide bond conserves many of the properties of the amide bond (e.g., conformation, steric bulk, electrostatic character, and possibility for hydrogen bonding). A general discussion of prior art techniques for the design and synthesis of peptidomimetics is provided in "Drug Design and Development", Chapter 14, Krogsgaard, Larsen, Liljefors and Madsen (Eds) 1996, Horwood Acad. Pub, the contents of which are incorporated herein by reference in their entirety. Suitable amide bond substitutes include the following groups: N-alkylation (Schmidt, R. et. al., Int. J. Peptide Protein Res., 1995, 46,47), retro-inverse amide (Chorev, M and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391), which all are incorporated herein by reference in their entireties. The peptides and polypeptide disclosed herein may include peptidomimetic equivalents.

A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

A "fragment" is a portion of an amino acid sequence or a polynucleotide which is identical in sequence to but shorter in length than a reference sequence. A fragment may comprise up to the entire length of the reference sequence, minus at least one nucleotide/amino acid residue. For example, a fragment may comprise from 5 to 1000 contiguous nucleotides or contiguous amino acid residues of a reference polynucleotide or reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous nucleotides or contiguous amino acid residues of a reference polynucleotide or reference polypeptide, respectively. A fragment may comprise a range of contiguous nucleotides or contiguous amino acid residues of a reference polynucleotide or reference polypeptide, respectively (e.g., LIMP-2), bounded by endpoints selected from any of 5, 10, 15, 20, 25, 30, 40, 50, 60, 70, 80, 90, 100, 150, 250, or 500 contiguous nucleotides or contiguous amino acid residues, respectively (e.g., a peptide fragment having 100-150 contiguous amino acid residues of a reference polypeptide). Fragments may be preferentially selected from certain regions of a molecule. The term "at least a fragment" encompasses the full length polynucleotide or full length polypeptide. Exemplary fragments of LIMP-2 may comprise or consist of the amino acids forming Helix 5 and/or the amino acids forming Helix 7. Exemplary fragments of LIMP-2 may comprise or consist of the amino acids from L152 to E175.

The LIMP-2 peptides disclosed herein may be characterized as comprising or consisting of fragments of full-length LIMP-2. The LIMP-2 peptides may have an amino acid sequence comprising or consisting of a contiguous amino acid sequence of full-length LIMP-2 which is less than about 100, 95, 90, 85, 80, 75, 70, 65, 60, 55, 50, 45, 40, 35, 30, 25, 20, 15, or 10 amino acids, or comprising or consisting of a contiguous amino acid sequence of LIMP-2 having a length within a range bounded by any two values selected from 100, 95, 90, 85, 80, 75, 70, 65, 60, 55, 50, 45, 40, 35, 30, 25, 20, 15, or 10 amino acids. For example, the disclosed LIMP-peptides may comprise a contiguous 10-50 amino acid sequence of LIMP-2.

The disclosed peptides preferably are relatively short. In some embodiments, the disclosed peptides have a length that is less than about 100, 95, 90, 85, 80, 75, 70, 65, 60, 55, 50, 45, 40, 35, 30, 25, 20, 15, or 10 amino acids, or the disclosed peptides have a length within a range bounded by any two values selected from 100, 95, 90, 85, 80, 75, 70, 65, 60, 55, 50, 45, 40, 35, 30, 25, 20, 15, or 10 amino acids. For example, in some embodiments, the disclosed peptides may have a length of 10-50, 10-40, 10-30, or 10-20 amino acids.

Fusion proteins also are contemplated herein. The disclosed polypeptides may comprise fusion proteins. A "fusion protein" refers to a protein formed by the fusion (e.g., via genetic fusion) of at least one LIMP-2 peptide or variant thereof as disclosed herein to at least one molecule of a heterologous protein (or fragment or variant thereof), which may include a cell-penetrating peptide (CPP) (see Bechara et al. "Cell-penetrating peptides: 20 years later, where do we stand?" FEBS Letters 587 (2013) 1693-1702, the content of which is incorporated herein by reference in its entirety) and/or a chaperone-mediated autophagy (CMA) targeting motif (see Cuervo et al., "Chaperone-mediated autophagy: roles in disease and aging," Cell Research (2014) 24:92-104, the content of which is incorporated herein by reference in its entirety). (See also, Milleti, "Cell-penetrating peptides: classes, origin, and current landscape," Drug Discovery Today, Volume 17, Numbers 15/16 Aug. 2012;). The heterologous protein(s) may be fused at the N-terminus, the C-terminus, or both termini of the LIMP-2 peptides or variants thereof. A fusion protein comprises at least a fragment or variant of the heterologous protein and at least a fragment or variant of the presently disclosed LIMP-2 peptides, which are associated with one another, preferably by genetic fusion (i.e., the fusion protein is generated by translation of a nucleic acid in which a polynucleotide encoding all or a portion of the heterologous protein is joined in-frame with a polynucleotide encoding all or a portion of the disclosed peptides or variants thereof). The heterologous protein and peptide, once part of the fusion protein, may each be referred to herein as a "portion," "region" or "moiety" of the fusion protein (e.g., a "a heterologous protein portion" or a "LIMP-2 peptide portion").

Conjugate proteins also are contemplated herein. A "conjugate protein" refers to a protein formed by the conjugation (i.e., via chemical linking or covalently bonding) of at least one LIMP-2 peptide molecule (or a variant thereof) to at least one molecule of a heterologous protein (or a fragment or variant thereof), which may include a cell-penetrating peptide (CPP) and/or a chaperone-mediated autophagy (CMA) targeting motif. A conjugate protein comprises at least a fragment or variant of the heterologous protein and one or more molecules of the presently disclosed peptides, which are associated with one another by covalent bonding. The heterologous protein and peptide, once part of the conjugate protein, may each be referred to herein as a "portion," "region" or "moiety" of the conjugate protein (e.g., "a heterologous protein portion" or a "LIMP-2 peptide portion"). Heterologous proteins may include protein having β-glucocerebrosidase activity, for example a protein comprising the amino acid sequence of any of SEQ ID NOs:6-8 or variants thereof such as fragments thereof. The LIMP-2 peptides, polypeptides, and variants thereof may be conjugated to a protein having B-glucocerebrosidase activity directly or indirectly via a linking moiety.

A "full length" polynucleotide sequence is one containing at least a translation initiation codon (e.g., methionine) followed by an open reading frame and a translation termination codon. A "full length" polynucleotide sequence encodes a "full length" polypeptide sequence.

"Homology" refers to sequence similarity or, interchangeably, sequence identity, between two or more polynucleotide sequences or two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence is defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide. For example, a variant may exhibit or more biological activities associated with LIMP-2.

The disclosed LIMP-2 peptides and polypeptides may be modified so as to comprise an amino acid sequence, or modified amino acids, or non-naturally occurring amino acids, such that the disclosed LIMP-2 peptides polypeptides cannot be said to be naturally occurring. In some embodiments, the disclosed LIMP-2 peptides or polypeptides are modified and the modification is selected from the group consisting of acylation, acetylation, formylation, lipoylation, myristoylation, palmitoylation, alkylation, isoprenylation, prenylation, and amidation. An amino acid in the disclosed polypeptides may be thusly modified, but in particular, the modifications may be present at the N-terminus and/or C-terminus of the polypeptides (e.g., N-terminal acylation or acetylation, and/or C-terminal amidation). The modifications may enhance the stability of the polypeptides and/or make the polypeptides resistant to proteolysis.

The disclosed peptides may be modified to replace a natural amino acid residue by an unnatural amino acid. Unnatural amino acids may include, but are not limited to an amino acid having a D-configuration, an N-methyl-α-amino acid, a non-proteogenic constrained amino acid, or a β-amino acid.

The disclosed peptides may be modified in order to increase the stability of the peptides in plasma. For example, the disclosed peptides may modified in order to make the peptides resistant to peptidases. The disclosed peptides may be modified to replace an amide bond between two amino acids with a non-amide bond. For example, the carbonyl moiety of the amide bond can be replaced by CH2 (i.e., to provide a reduced amino bond: —CH2-NH—). Other suitable non-amide replacement bonds for the amide bond may include, but are not limited to: an endothiopeptide, —C(S)—NH, a phosphonamide, —P(O)OH—NH—), the NH-amide bond can be exchanged by O (depsipeptide, —CO—O—), S (thioester, —CO—S—) or $CH_2$ (ketomethylene, —CO—$CH_2$—). The peptide bond can also be modified as follows: retro-inverso bond (—NH—CO—), methylene-oxy bond (—$CH_2$—), thiomethylene bond (—$CH_2$—S—), carbabond (—$CH_2$—$CH_2$—), hydroxyethylene bond (—CHOH—$CH_2$—) and so on, for example, to increase plasma stability of the peptide sequence (notably towards endopeptidases).

The disclosed peptides may include a non-naturally occurring N-terminal and/or C-terminal modification. For example, the N-terminal of the disclosed peptides may be modified to include an N-acylation or a N-pyroglutamate modification (e.g., as a blocking modification). The C-terminal end of the disclosed peptides may be modified to include a C-amidation. The disclosed peptides may be conjugated to carbohydrate chains (e.g., via glycosylation to glucose, xylose, hexose), for example, to increase plasma stability (notably, resistance towards exopeptidases).

The disclosed peptides may include an N-terminal esterification (e.g., a phosphoester modification) or a pegylation modification, for example, to enhance plasma stability (e.g. resistance to exopeptidases) and/or to reduce immunogenicity.

The disclosed peptides may be pegylated in order to increase the molecular weigh to of the peptides (e.g., to greater than about 20, 30, 40, 50, 60, or 70 kDa) to retard excretion of the peptide through the kidneys (renal clearance).

The disclosed LIMP-2 peptides may be conjugated to a resin or a solid support. For example, the disclosed LIMP-2 peptides may be conjugated via there N-terminus and/or C-terminus to a solid support, either directly or via a linking moiety that conjugates the peptides to the resin or the solid support.

The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. Percent identity for a nucleic acid sequence may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at the NCBI website. The "BLAST 2 Sequences" tool can be used for both blastn and blastp.

Percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

A "variant," "mutant," or "derivative" of a particular nucleic acid sequence may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The words "insertion" and "addition" refer to changes in an amino acid or nucleotide sequence resulting in the addition of one or more amino acid residues or nucleotides, respectively. An insertion or addition may refer to 1, 2, 3, 4, 5, 10, 20, 30, 40, 50, 60, 70, 80, 90, 100, 150, or 200 amino acid residues or nucleotides.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, J. et al. (1989) Molecular Cloning: A Laboratory Manual, $2^{nd}$ ed., vol. 1 3, Cold Spring Harbor Press, Plainview N.Y. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

"Substantially isolated or purified" nucleic acid or amino acid sequences are contemplated herein. The term "substantially isolated or purified" refers to nucleic acid or amino acid sequences that are removed from their natural environment, and are at least 60% free, preferably at least 75% free, and more preferably at least 90% free, even more preferably at least 95% free from other components with which they are naturally associated.

"Transformation" and "transfections" describe a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "composition comprising a given polypeptide" and a "composition comprising a given polynucleotide" refer broadly to any composition containing the given polynucleotide or amino acid sequence. The composition may comprise a dry formulation or an aqueous solution. The compositions may be stored in any suitable form including, but not limited to, freeze-dried form and may be associated with a stabilizing agent such as a carbohydrate. The compositions may be aqueous solution containing salts (e.g., NaCl), detergents (e.g., sodium dodecyl sulfate; SDS), and other components (e.g., Denhardt's solution, dry milk, salmon sperm DNA, and the like).

The disclosed pharmaceutical composition may comprise the disclosed LIMP-2 peptides, polypeptides, variants at any suitable dose. Suitable doses may include, but are not limited to, about 0.01 μg/dose, about 0.05 μg/dose, about 0.1 μg/dose, about 0.5 μg/dose, about 1 μg/dose, about 2 μg/dose, about 3 μg/dose, about 4 μg/dose, about 5 μg/dose, about 10 μg/dose, about 15 μg/dose, about 20 μg/dose, about 25 μg/dose, about 30 μg/dose, about 35 μg/dose, about 40

µg/dose, about 45 µg/dose, about 50 µg/dose, about 100 µg/dose, about 200 µg/dose, about 500 µg/dose, or about 1000 µg/dose.

The disclosed LIMP-2 peptides, polypeptides, or variants thereof may be administered at any suitable dose level. In some embodiments, a subject in need thereof is administered a peptide, polypeptide, or variant thereof at a dose level of from about 1 ng/kg up to about 2000 ng/kg. In some embodiments, the peptide, polypeptide, or variant thereof is administered to the subject in need thereof at a dose level of at least about 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg or 2000 ng/kg. In other embodiments, the peptide, polypeptide, or variant thereof is administered to the subject in need thereof at a dose level of less than about 2000 ng/kg, 1000 ng/kg, 500 ng/kg, 200 ng/kg, 100 ng/kg, 50 ng/kg, 20 ng/kg, 10 ng/kg, 5 ng/kg, 2 ng/kg, or 1 ng/kg. In further embodiments, the peptide, polypeptide, or variant thereof is administered to a subject in need thereof within a dose level range bounded by any 1 ng/kg, 2 ng/kg, 5 ng/kg, 10 ng/kg, 20 ng/kg, 50 ng/kg, 100 ng/kg, 200 ng/kg, 500 ng/kg, 1000 ng/kg or 2000 ng/kg.

The disclosed LIMP-2 peptides, polypeptides, or variants thereof may be administered under any suitable dosing regimen. Suitable dosing regimens may include, but are not limited to, daily regimens (e.g., 1 dose/day for 1, 2, 3, 4, 5, 6, 7 or more days), twice daily regimens (e.g., 2 doses/day for 1, 2, 3, 4, 5, 6, 7 or more days), and thrice daily regiments (e.g., 3 doses/day for 1, 2, 3, 4, 5, 6, 7 or more days). Suitable regiments also may include dosing every other day, 3 times/week, once a week, for 1, 2, 3, 4, or more weeks.

The disclosed LIMP-2 peptides, polypeptides, or variants thereof (or pharmaceutical compositions comprising the disclosed peptides, polypeptides, or variants thereof) may be administered to a subject in need thereof by any suitable route. In some embodiments, the disclosed peptides, polypeptides, or variants thereof are administered to a subject in need thereof via an injectable delivery route selected from the group consisting of intravenous, intradermal, intramuscular, intraperitoneal, subcutaneous, or epidural routes.

ILLUSTRATIVE EMBODIMENTS

The following embodiments are illustrative and are not intended to limit the scope of the claims subject matter.

Embodiment 1

An isolated peptide comprising, consisting essentially of, or consisting of the amino acid sequence of any of SEQ ID NOs: 1-3 or an amino acid sequence having a least about 80% sequence identity to any of SEQ ID NOs: 1-3.

Embodiment 2

The isolated peptide of embodiment 1, wherein the isolated peptide does not comprise, consist essentially of, or consist of the amino acid sequence of SEQ ID NO:4.

Embodiment 3

The isolated peptide of embodiment 1 or 2, wherein the isolated peptide does not comprise amino acids 150 and 151 of SEQ ID NO: 1.

Embodiment 4

The isolated peptide of any of the foregoing embodiments, wherein the isolated peptide comprises amino acid 168 of SEQ ID NO: 1.

Embodiment 5

The isolated peptide of any of the foregoing embodiments, wherein the isolated peptide comprises an amino acid sequence comprising two or more contiguous amino acids of SEQ ID NO:5.

Embodiment 6

The isolated peptide of any of the foregoing embodiments, wherein the isolated peptide comprises an N-terminal methionine residue.

Embodiment 7

The isolated peptide of any of embodiments 1-5, wherein the peptide has one or more amino acid modifications selected from the group consisting of acylation (e.g., N-terminal acylation), acetylation (e.g., N-terminal acetylation), formylation, lipolylation, myristoylation, palmitoylation, alkylation, isoprenylation, prenylation, and amidation (e.g., C-terminal amidation).

Embodiment 8

An isolated polypeptide comprising: (i) the isolated peptide of any of embodiments 1-7; and optionally fused to the isolated peptide at its N-terminus, C-terminus, or both termini, one or more of (ii) cell-penetrating protein motif and (iii) a chaperone-mediated autophagy (CMA) targeting motif.

Embodiment 9

The isolated peptide or isolated polypeptide of any of the foregoing embodiments, wherein the isolated peptide or isolated polypeptide do not comprise N-linked glycosylation and/or O-linked glycosylation.

Embodiment 10

The isolated peptide or isolated polypeptide of any of the foregoing embodiments, wherein the isolated peptide or isolated polypeptide exhibits one or more biological activities associated with LIMP-2.

Embodiment 11

The isolated peptide or isolated polypeptide of embodiment 10, wherein the biological activity comprises binding to β-glucocerebrosidase, and preferably, increasing biological activity of β-glucocerebrosidase including hydrolysis of glycosylceramide by at least about 10%, 20%, 30%, 40%, 50%, 60%, 70%, 80%, 90%, 100%, or higher.

Embodiment 12

The isolated peptide or isolated polypeptide of embodiment 10, wherein the biological activity comprises binding to a virus, including, but not limited to, enteroviruses such as E71.

Embodiment 13

A pharmaceutical composition comprising the isolated peptide or the isolated polypeptides of any of embodiments 1-12 and a pharmaceutically acceptable carrier, excipient, or diluent.

Embodiment 14

The pharmaceutical composition of embodiment 13, wherein the composition comprises an effective amount of the isolated peptide or isolated polypeptide for binding to β-glucocerebrosidase, and preferably, increasing biological activity of β-glucocerebrosidase including hydrolysis of glycosylceramide by at least about 10%, 20%, 30%, 40%, 50%, 60%, 70%, 80%, 90%, 100%, or higher.

Embodiment 15

The pharmaceutical composition of embodiment 13, wherein the composition comprises an effective amount of the isolated peptide or isolated polypeptide for binding to a virus, including, but not limited to, enteroviruses such as E71.

Embodiment 16

A method for treating a disease or disorder associated with the biological activity of β-glucocerebrosidase in a subject in need thereof, the method comprising administering the composition of embodiment 13 or 14 to the subject.

Embodiment 17

The method of embodiment 16, wherein the disease or disorder is Gaucher disease.

Embodiment 18

The method of embodiment 16, wherein the disease or disorder is a synucleinopathy, including but not limited to Parkinson's disease and dementia with Lewy bodies.

Embodiment 19

The method of any of embodiments 16-18, wherein the subject has a mutation in SCARB2 and/or GBA1.

Embodiment 20

A method for treating or preventing infection by a virus in a subject in need thereof, the method comprising administering the composition of embodiment 13 or 14 to the subject, wherein optionally the virus is an enterovirus such as E71.

Embodiment 21

A method for activating β-glucocerebrosidase, the method comprising contacting the β-glucocerebrosidase with the isolated peptide or the isolated polypeptide of any of embodiments 1-12.

Embodiment 22

A method for preparing a pharmaceutical composition, the method comprising (i) performing the method of embodiment 21 to obtain activated β-glucocerebrosidase, and (ii) combining the activated β-glucocerebrosidase with a pharmaceutically acceptable carrier, excipient, or diluent.

Embodiment 23

A pharmaceutical composition prepared by the method of embodiment 22.

Embodiment 24

The pharmaceutical composition of embodiment 23, wherein the composition comprises an effective amount of the isolated peptide or isolated polypeptide for binding to β-glucocerebrosidase, and preferably, increasing biological activity of β-glucocerebrosidase including hydrolysis of glycosylceramide by at least about 10%, 20%, 30%, 40%, 50%, 60%, 70%, 80%, 90%, 100%, or higher.

Embodiment 25

The pharmaceutical composition of embodiment 23, wherein the composition comprises an effective amount of the isolated peptide or isolated polypeptide for binding to a virus, including, but not limited to, enteroviruses such as E71.

Embodiment 26

A method of isolating β-glucocerebrosidase from a solution comprising β-glucocerebrosidase, the method comprising: (i) contacting the solution with a solid or semi-solid substrate comprising the isolated peptide or isolated polypeptide of any of embodiments 1-12 immobilized on the solid or semi-solid substrate (e.g., via the isolated peptide or isolated polypeptide being covalently bonded to the solid or semi-solid substrate either directly or indirectly via a chemical linker, or via the isolated peptide or isolated polypeptide being non-covalently bonded to the solid or semi-solid substrate), wherein the solid or semi-solid substrate binds the J3-glucocerebrosidase to form a complex; and (ii) washing the complex with a washing solution to remove components other than β-glucocerebrosidase from the complex.

Embodiment 27

The method of embodiment 26, further comprising (iii) washing the complex with an elution buffer to remove the bound β-glucocerebrosidase.

Embodiment 28

A method, which optionally is a method for identifying a compound that binds to β-glucocerebrosidase and optionally modulates the activity of β-glucocerebrosidase, the method comprising (i) combining: (a) β-glucocerebrosidase, (b) the isolated peptide or isolated polypeptide of any of embodiments 1-12, and (c) the compound in a solution; and (ii) determining whether the compound prevents binding between (a) the β-glucocerebrosidase and (b) the isolated peptide or isolated polypeptide.

Embodiment 29

The method of embodiment 28, wherein the β-glucocerebrosidase comprises a label and/or the isolated peptide or isolated polypeptide comprises a label (e.g., a label that emits a detectable signal, and the detectable signal of the label that is emitted when β-glucocerebrosidase and the peptide are bound is different than the detectable signal of the label that is emitted when 1-glucocerebrosidase and the peptide are not bound).

Embodiment 30

The method of embodiment 29, wherein the label is a fluorescent label.

Embodiment 31

The method of embodiment 30, wherein determining whether the compound prevents binding between β-glucocerebrosidase comprises performing a fluorescence polarization assay.

Embodiment 32

The method of embodiment 31, wherein performing a fluorescence polarization assay comprises exciting the fluorescent label with a polarized excitation light and detecting a fluorescent signal through a polarization emission filter.

Embodiment 33

The method of any of embodiments 29-32, further comprising determining whether the compound binds to β-glucocerebrosidase and/or further comprising determining whether the compound modulates a biological activity of β-glucocerebrosidase (e.g., determining whether the compound binds to β-glucocerebrosidase and/or determining whether the compound increases a biological activity of β-glucocerebrosidase including hydrolysis of glycosylceramide by at least about 10%, 20%, 30%, 40%, 50%, 60%, 70%, 80%, 90%, 100%, or higher).

Embodiment 34

The isolated peptide or the isolated polypeptide of any of embodiments 1-12 further comprising a detectable label, including but not limited to a fluorescent label or a radio label.

Embodiment 35

An isolated polynucleotide encoding the isolated polypeptide or the isolated polypeptide of any of embodiments 1-12.

Embodiment 36

An expression vector comprising the isolated polynucleotide of embodiment 35 operably linked to a promoter.

Embodiment 36

An isolated cell comprising the expression vector of embodiment 32.

Examples

The following Examples are illustrative and are not intended to limit the scope of the claimed subject matter.

Reference is made to the manuscript: Zunke et al., "Characterization of the complex formed by β-glucocerebrosidase and the lysosomal integral membrane protein type-2," Proc. Nat'l Acad. Sci. USA, 2016 Apr. 5; 113(14):3791-6, which content is incorporated herein by reference in its entirety.

Abstract

The lysosomal integral membrane protein type-2 (LIMP-2) plays a pivotal role in the delivery of β-glucocerebrosidase (GC) to lysosomes. Mutations in GC result in Gaucher's disease (GD) and are the major genetic risk factor for the development of Parkinson's disease (PD). Variants in the LIMP-2 gene cause Action Myoclonus Renal Failure syndrome and have also been linked to PD. Given the importance of GC and LIMP-2 in disease pathogenesis, we studied their interaction sites in more detail. Our previous data demonstrated that the crystal structure of LIMP-2 displayed a hydrophobic three helix bundle, composed of helix 4, 5 and 7 of which helix 5 and 7 are important for ligand binding. Here, we identified a similar helical motif in GC through surface potential analysis. Co-immunoprecipitation and immunofluorescence studies revealed a triple-helical interface region within GC as critical for LIMP-2 binding and lysosomal transport. Based on these findings, we generated a LIMP-2 helix 5-derived peptide that precipitated and activated recombinant wild-type and GD-associated N370S mutant GC in vitro. The Helix 5 peptide fused to a cell-penetrating peptide also activated endogenous lysosomal GC and reduced α-synuclein levels suggesting that LIMP-2-derived peptides can be used to efficiently activate endogenous as well as recombinant wild-type or mutant GC. Our data also provide a structural model of the LIMP-2/GC complex that will facilitate the development of GC chaperones and activators as potential therapeutics for GD, PD and related synucleinopathies.

Significance Statement

Apart from the LIMP-2-dependent trafficking of β-glucocerebrosidase (GC) to lysosomes little is known about the interaction of LIMP-2 and GC on the molecular level. The structural as well as biochemical characterization of LIMP-2/GC interaction sites is of potential importance for the design of GC activating compounds. We also provide evidence that a LIMP-2-derived helical peptide can be used for efficient purification and activation of recombinant as well as endogenous GC. These results provide a molecular framework for the design of GC activators as potential treatments in Parkinson's disease and related synucleinopathies.

Introduction

The lysosomal glucosidase GC is required for hydrolysis of glucosylceramide and is targeted to lysosomes in a mannose-6 phosphate-independent manner by the lysosomal integral membrane protein type-2 (LIMP-2) (1, 2). Interaction of the two proteins occurs in the endoplasmic reticulum (ER) (1, 3), followed by trafficking of the LIMP-2/GC complex to lysosomes. Mutations in LIMP-2 cause Action Myoclonus Renal Failure (AMRF) (4). LIMP2 mutants linked to AMRF localize to the ER (3), causing missorting and lysosomal depletion of GC, highlighting the importance of functional LIMP-2 for correct targeting of GC. Reduced lysosomal activity of GC is also a hallmark of GD, which is caused by mutations in GC. Whereas only a few AMRF-causing mutations are known for LIMP-2, more than 300 mutations within GC are described (5), affecting either the activity, stability and/or the intracellular distribution of the enzyme. Patients carrying mutations in GC have an increased risk of developing synucleinopathies including Parkinson's disease (PD) and dementia with Lewy bodies (6, 7). Importantly, a reduction in GC activity is also found in patients with sporadic PD (8). We recently showed reduced neuronal GC activity and increased α-synuclein in LIMP-2-deficient mice that also exhibited severe neurological deficits (9). These findings are supported by a significant association of genetic variations in the LIMP-2 locus with dementia with Lewy bodies (10) and emphasize the involvement of the LIMP-2-mediated lysosomal transport of GC in the pathogenesis of synucleinopathies. Augmentation of GC activity in murine brain of GD and PD mouse models led to a reduction of α-synuclein accumulation and amelioration of neuronal pathology (11, 12). Several hypotheses suggest a link between mutated GC and dysregulated α-synuclein homeostasis (13). For example, the GC substrate glucosylceramide has been proposed to promote α-synuclein accumulation by exerting a stabilizing effect on toxic oligomeric forms of α-synuclein (14). A feedback loop, where accumulated α-synuclein partially blocks ER to Golgi transport of GC was suggested to further increase this pathological cascade (14).

The recently solved crystal structure of the LIMP-2 ectodomain revealed an exposed three helix bundle, which is formed by helices 4, 5 and 7, whereas helix 5 and 7 are likely to serve as a GC-binding domain (15). Since the secondary structure and hydrophobicity of this region is important for binding and intracellular transport of GC (1), we hypothesized that GC might harbor a similar motif necessary for LIMP-2 binding. Here, we describe the identification and characterization of a hydrophobic helical interface within GC, mediating binding to LIMP-2. We therefore suggest a novel LIMP-2/GC interaction model that may be important for the design of small molecule GC activators. Furthermore, we generated a LIMP-2-derived helical peptide that can be utilized to purify, activate and stabilize GC in vitro as well as in cell-based assays. Our data also suggest that this chaperone-like activity of LIMP-2 could increase lysosomal targeting of wild-type or mutant forms of GC, thereby decreasing intralysosomal accumulation of glucosylceramide in synucleinopathies.

Results

LIMP-2 and GC Interaction is Mediated by Hydrophobic Helical Interfaces on Both Proteins.

Figure 4:
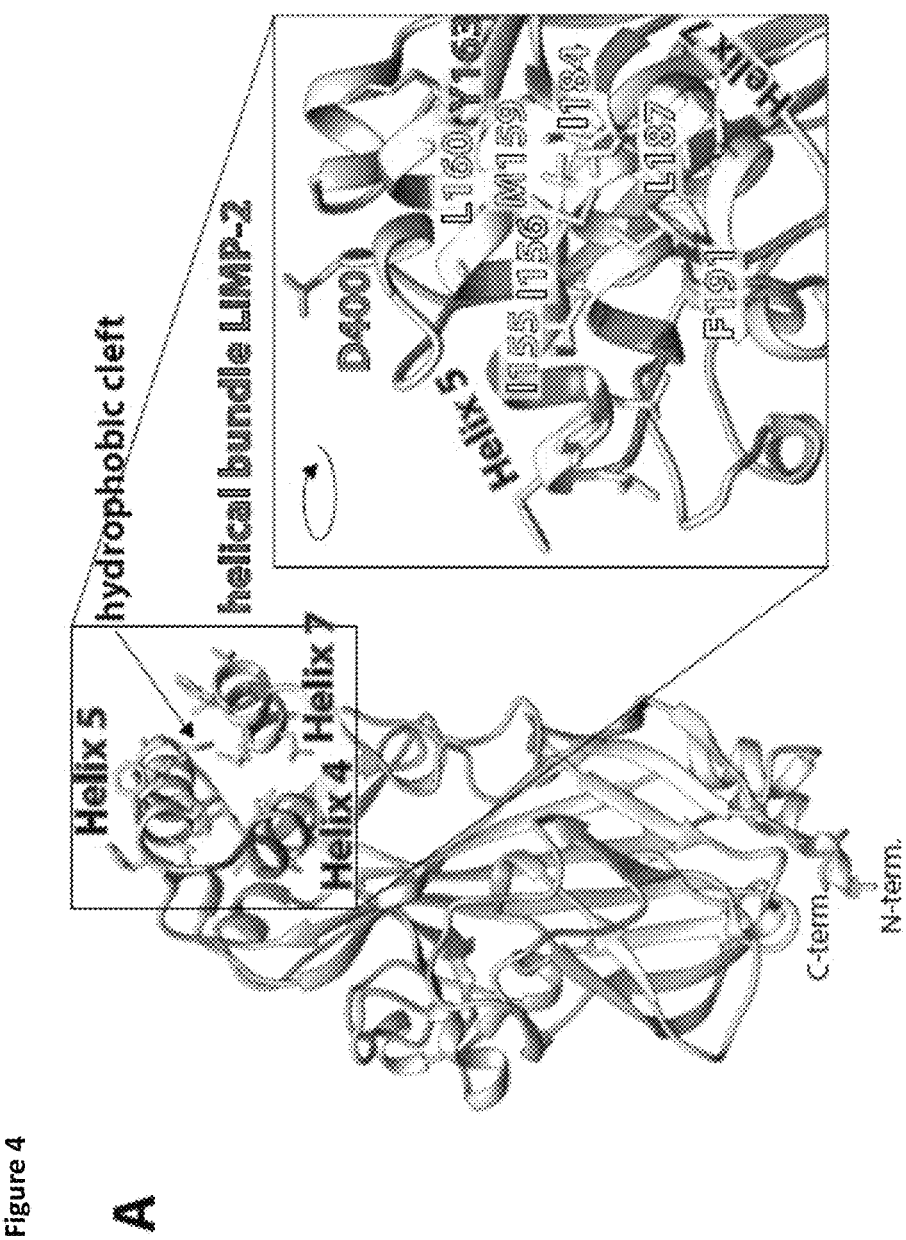
FIG. 4: Structural and molecular studies of LIMP-2 and GC interaction. A) Crystal structure of LIMP-2 (PDB: 4F7B) with highlighted helical bundle (red): helix 5, helix 7 and helix 4. Hydrophobic amino acids are indicated in yellow. The box shows a magnification of the helical bundle with mutated amino acids visualized. The D400K control mutant located outside the helical bundle is shown in green. B) Human and murine amino acid sequences of the LIMP-2 binding region with introduced point mutations. Hydrophobic amino acids within the helical region (red) of helix 5 and helix 7 are highlighted in yellow. C) GC activity after transfection of LIMP-2 point mutants into LIMP-2-deficient MEFs. Only mutants capable of binding and transporting GC to the lysosome can rescue GC activity like wild-type (WT) LIMP-2. Enzymatic activity is normalized to LIMP-2 WT and subtracted from background values (n=4-7). D) Triple-immunofluorescence staining of GC-deficient MEF cells transfected with GC mutants (α-hGC) and stained for endogenous lysosomal markers LAMP-2 (red) and LIMP-2 (blue). Purple color indicates a co-localization of the two lysosomal markers and a white signal (upper panel) points to an additional overlay of GC highlighting lysosomal localization of the respective GC construct. E) Analysis of signal overlay of stained GC mutants with the lysosomal marker LAMP-2 shown as Pearson's Index (n=2-3). F) Immunofluorescence of binding-deficient GC mutants in GC-deficient cells stained for GC (α-hGC) and the endoplasmatic reticulum (ER) marker protein-disulfid-isomerase (PDI). A yellow signal indicates ER localization of GC mutants. G) Pearson's index of co-localization of GC and PDI (n=β-6). H) Immunoblot of EndoH and PNGaseF digests of GC mutants (α-hGC) with and without co-expression of LIMP-2 (anti-myc) in GC-deficient cells with actin as loading control. Protein fractions resistant to EndoH digestion indicate post ER localization. Dotted lines separate individual blots. I) Densitometry of EndoH digests, showing post ER/ER ratio normalized to GC WT (n=β-6). J) Immunofluorescence staining of GC WT and mutants L91E, L94E and L156E (α-hGC; red) co-expressed with LIMP-2 (t-myc; green) in GC-deficient cells. Area of magnification is highlighted by a white box. K) Pearson's index as a measure of the degree of LIMP-2-GC co-localization (n=β-9). L) Enzyme activity (normalized to mock control) of GC mutants overexpressed in N2a cells with or without LIMP-2 co-expression (dotted line indicates background activity; n=4). A One-Way ANOVA together with a subsequent Tukey-Kramer post-hoc test was used for subpanel C, E and G. A two-sided Student's t-test was used for analysis shown in I. *; ; * denote p<0.05; 0.01; 0.001 when comparing all mutants to cells transfected with GC WT.
Figure 4:
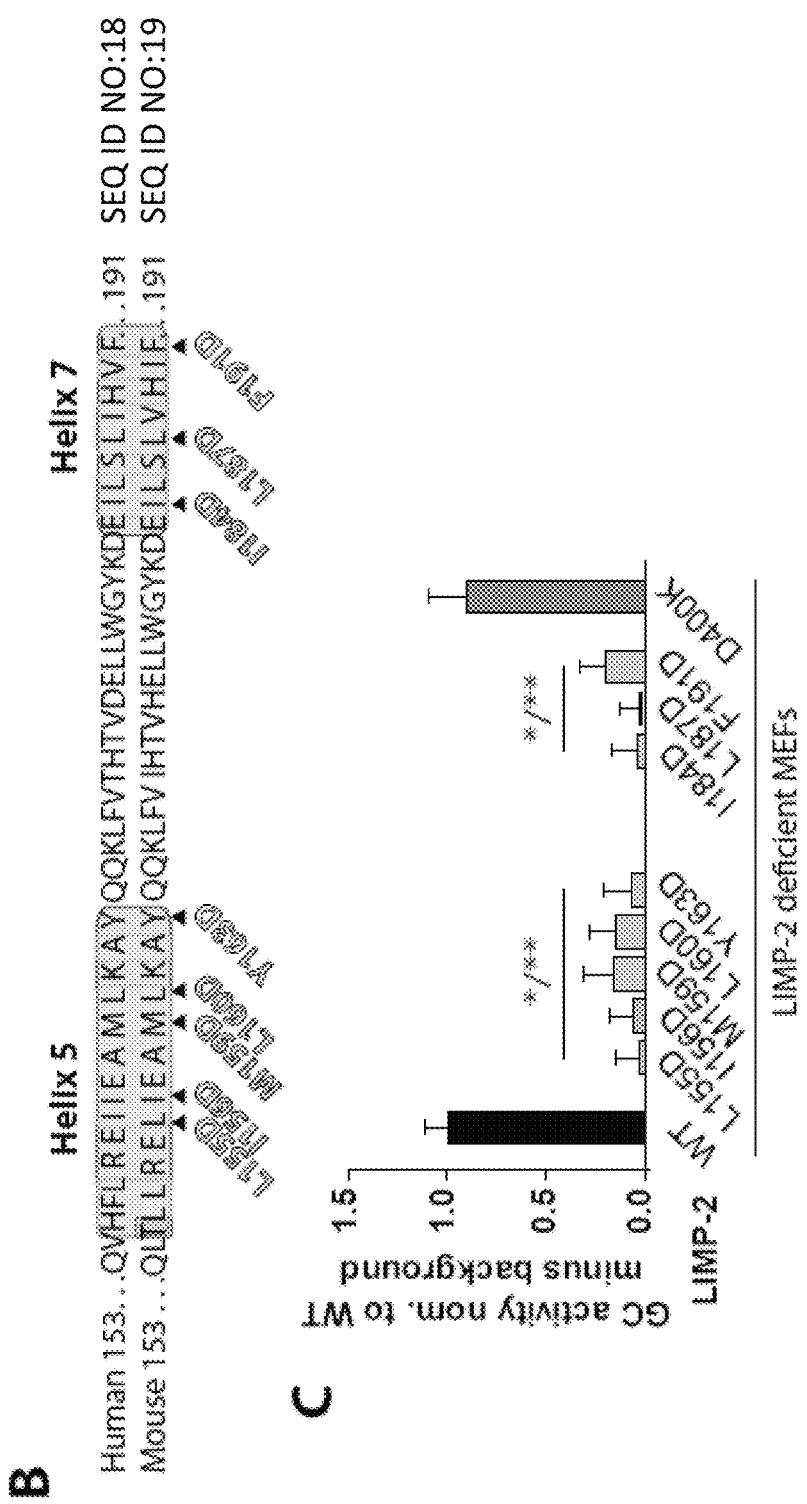
Figure 4:
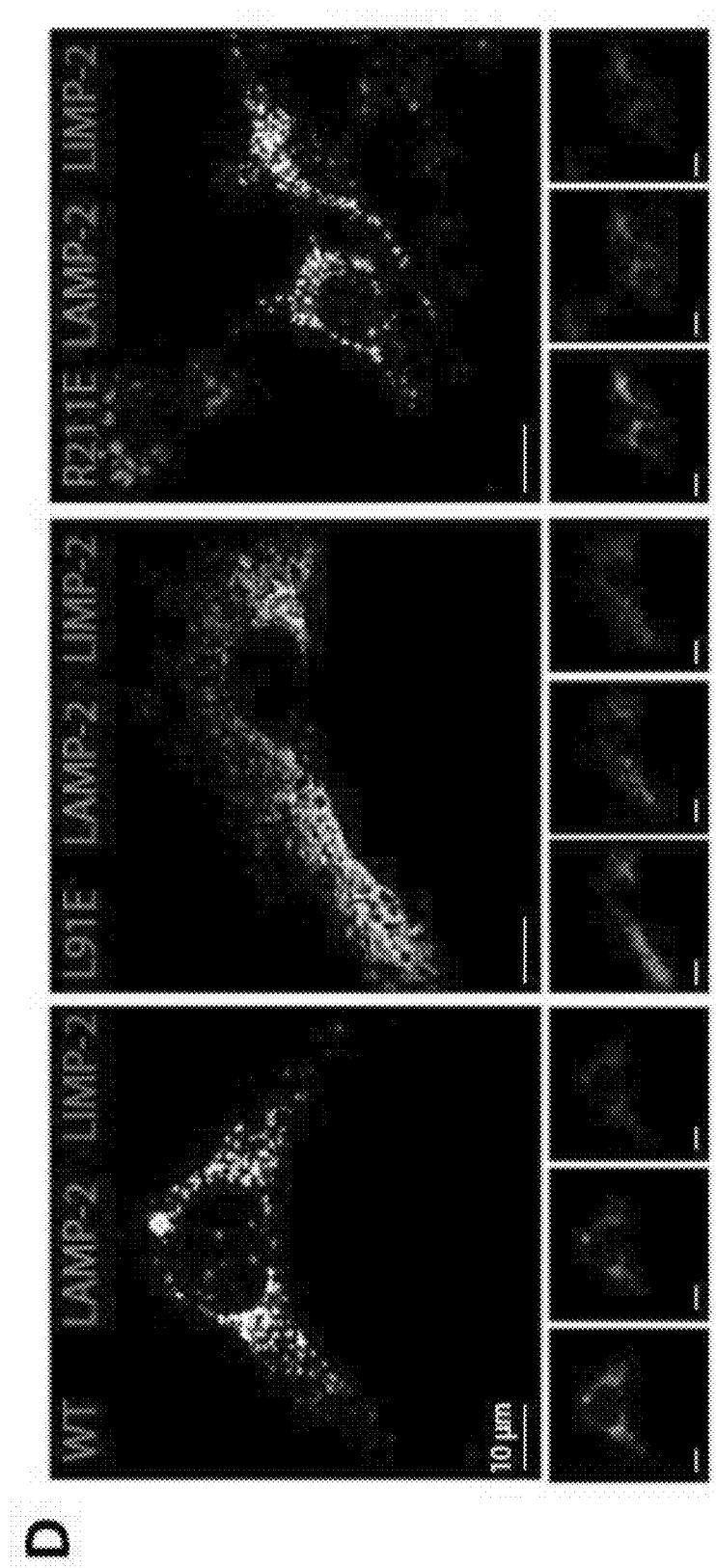
Figure 4:
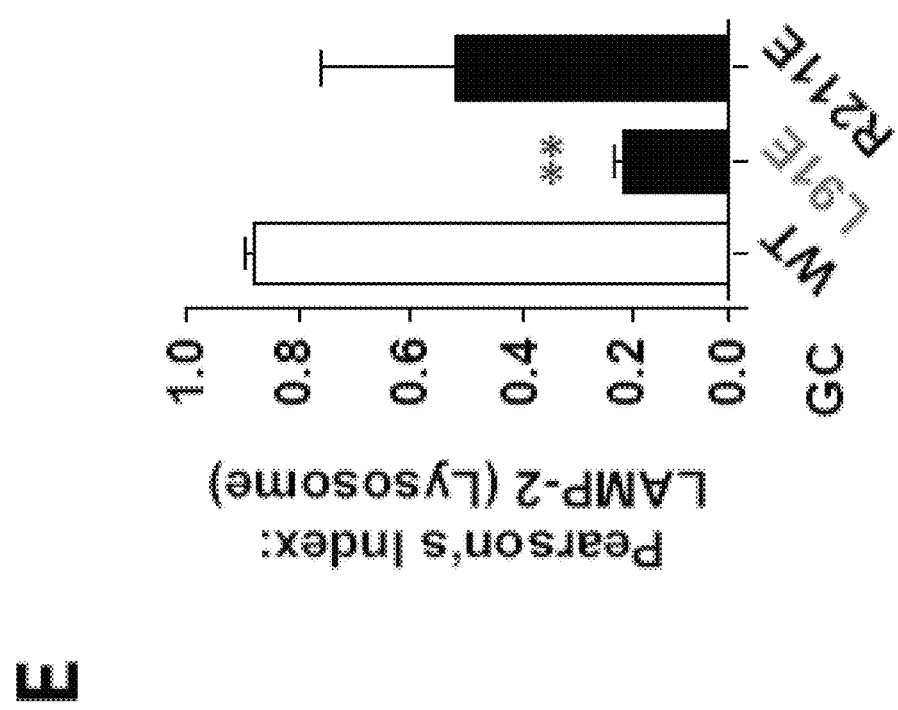
Figure 4:
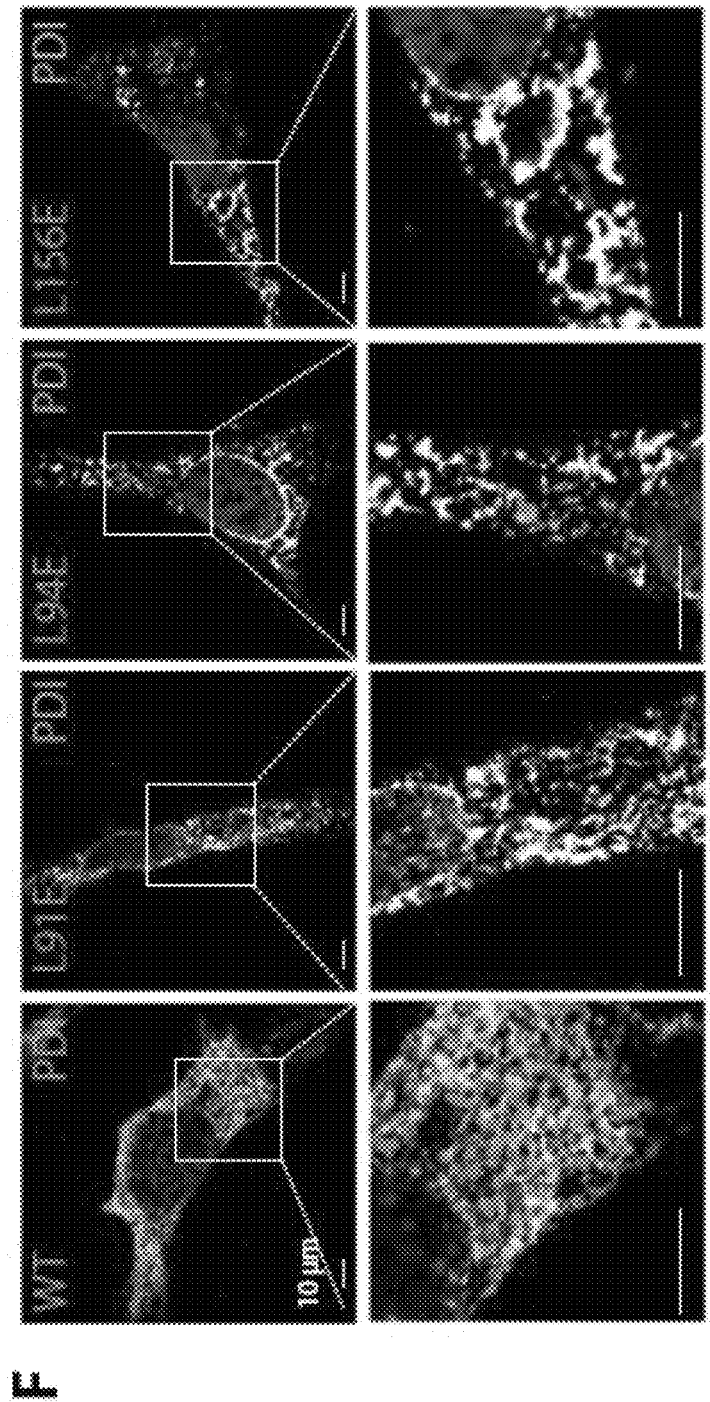
Figure 4:
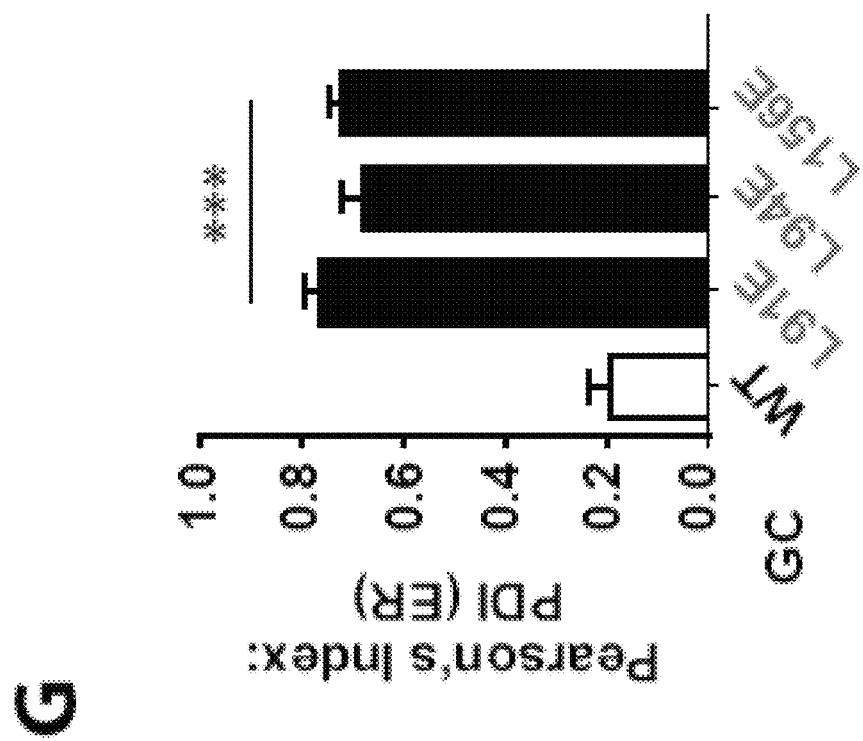
Figure 4:
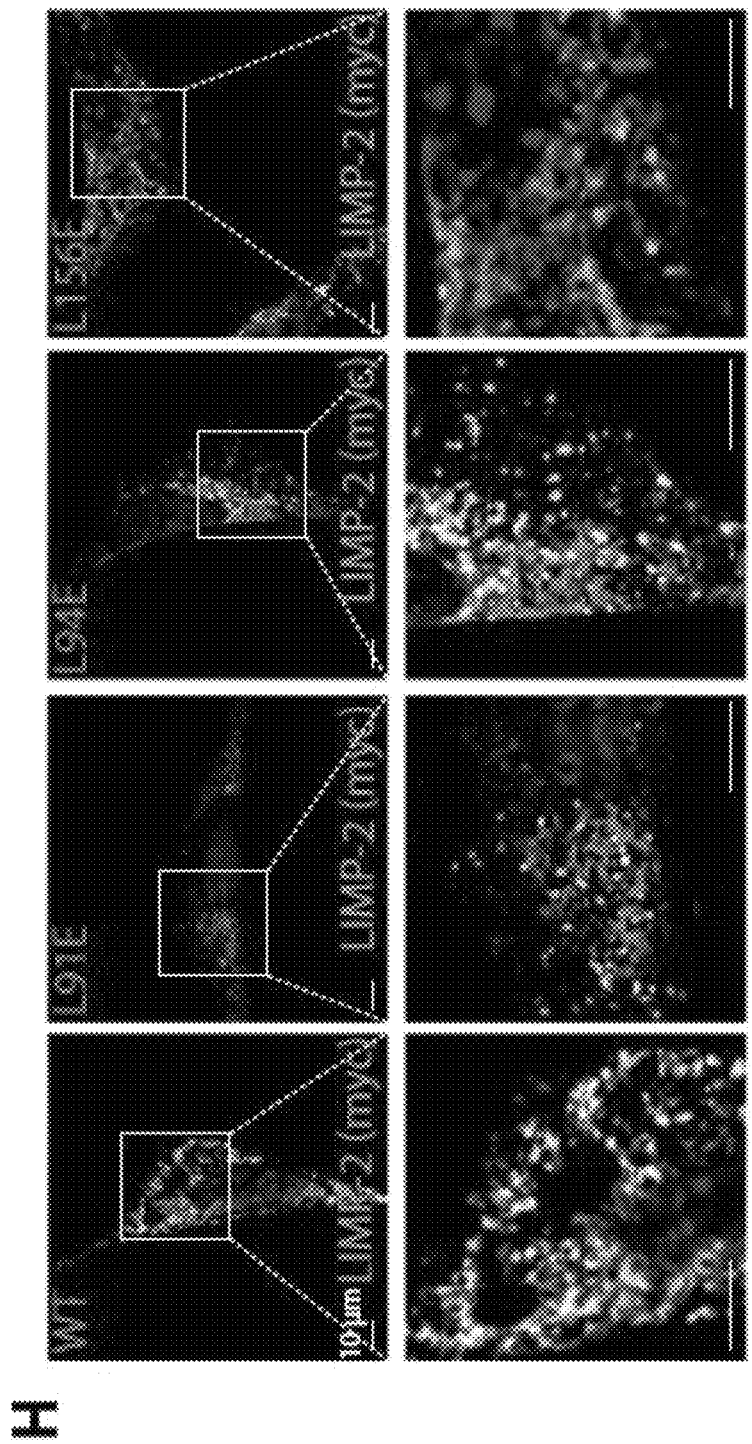
Figure 4:
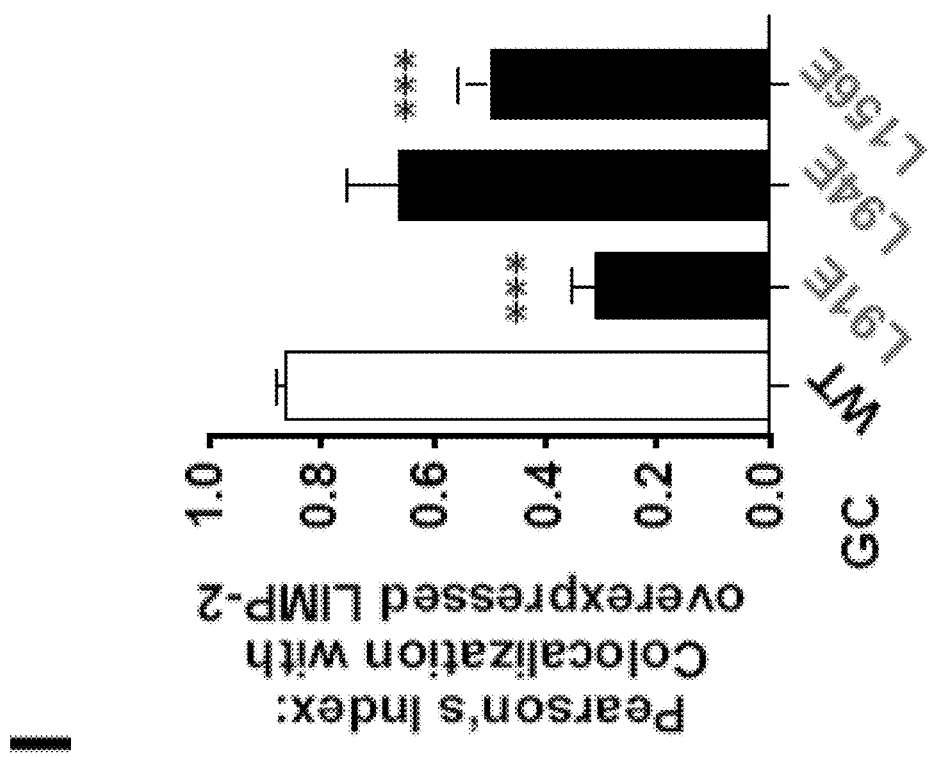
Figure 4:
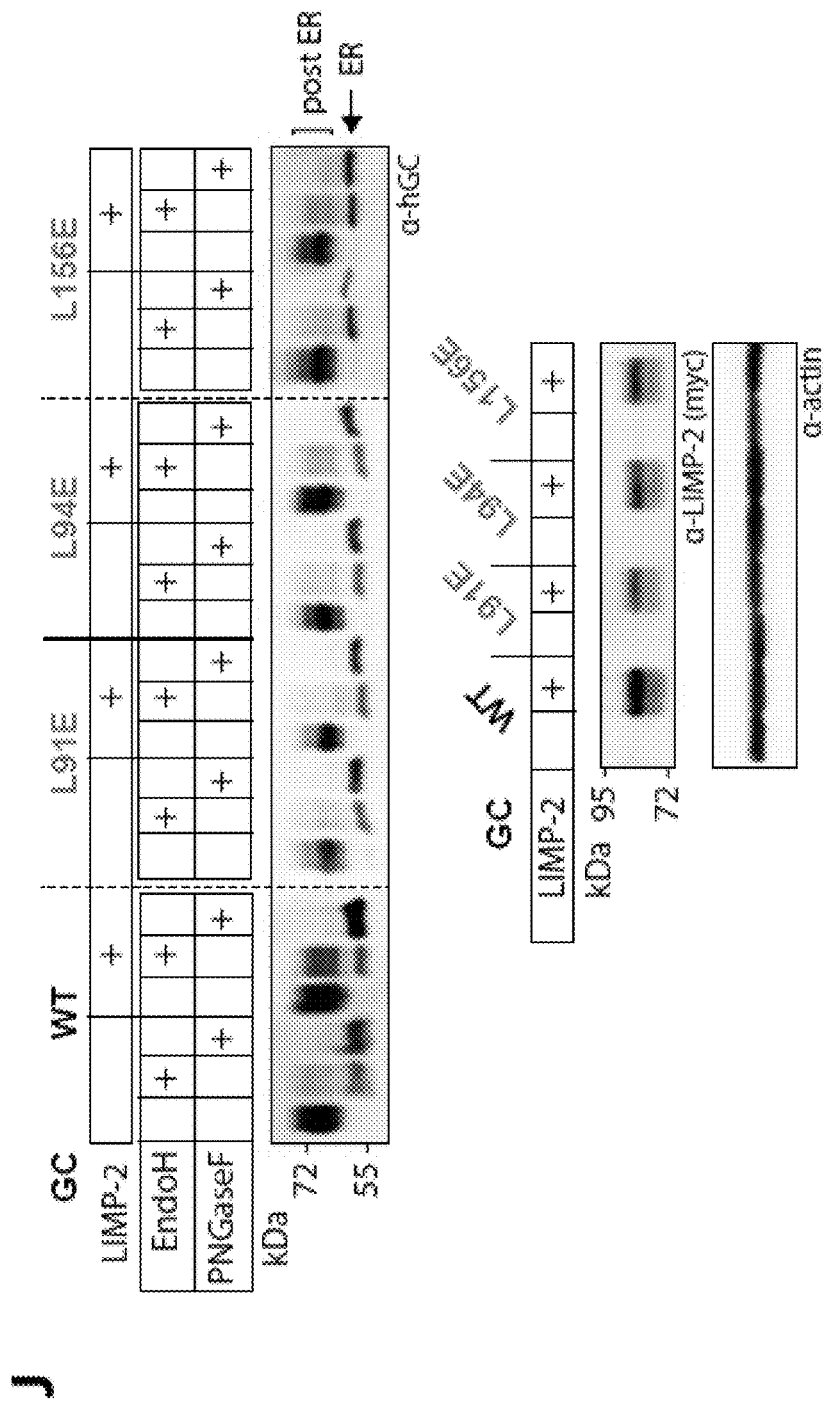
Figure 4:
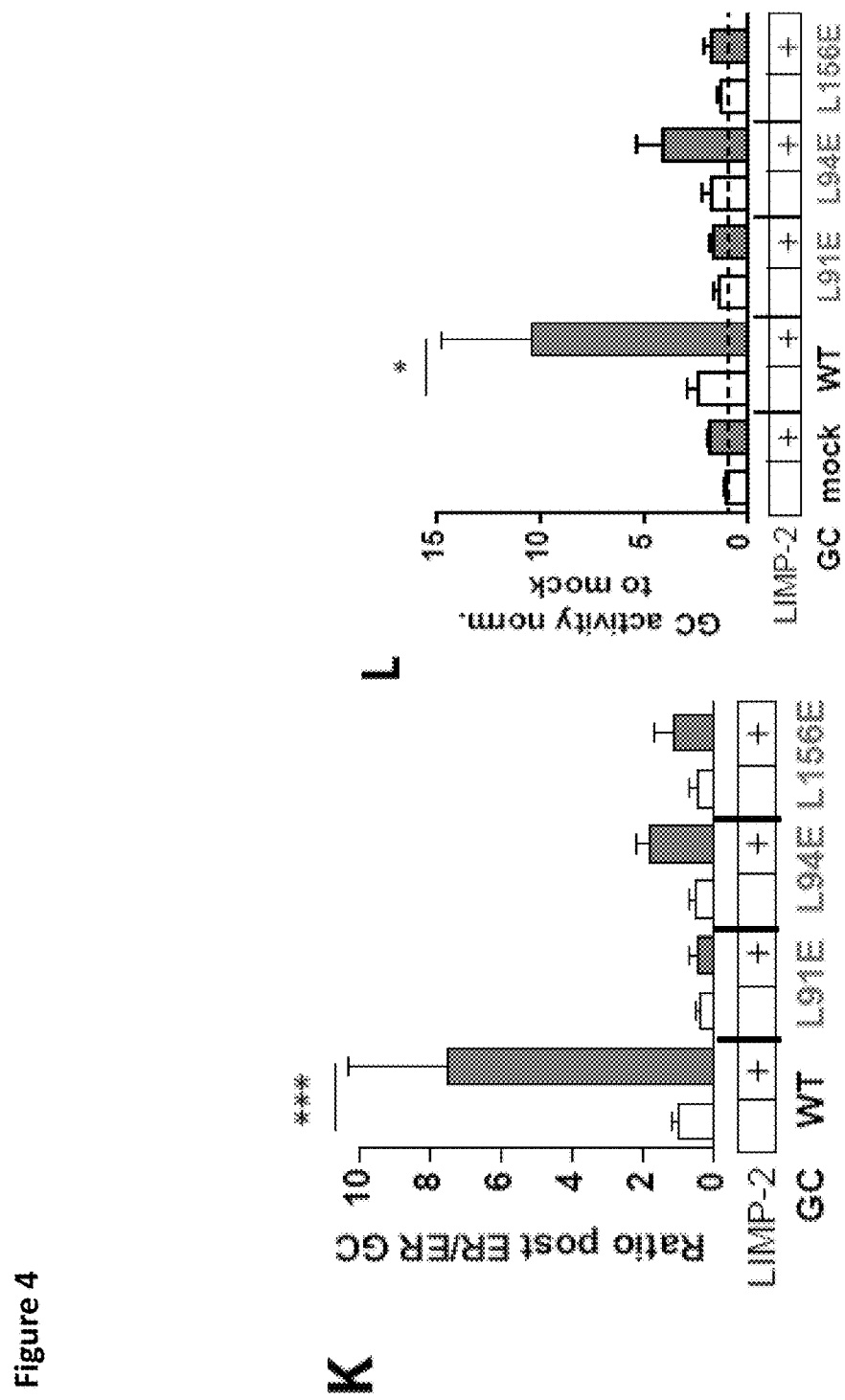

Previous mutagenesis studies, guided by the crystal structure of the LIMP-2 ectodomain indicated that the hydrophobic helices 5 and 7 are critical for an interaction with GC (15). Consistent with this, we show here that mutations within helix 5 and 7 of LIMP-2 that reduce the hydrophobicity of this region (FIG. 4A, B) impaired the ability to rescue reduced GC activity in a LIMP-2-deficient cell system (FIG. 4C). This confirms in a cellular model that the hydrophobicity of the helical bundle in LIMP-2 is critical for binding and intracellular transport of GC. Since the interaction domain within the GC protein is unknown, we utilized the available crystal structure of GC (16, 17) and surface potential analysis to identify potential GC/LIMP-2 interaction sites in silico (FIG. 1A). A potential interaction region in GC was identified by its similarity to helix 5 and 7 of LIMP-2, which consisted of a hydrophobic helical interface (FIG. 1A) and is composed of three helices (1a, 1b and 2) (FIG. 1B).

To determine if these helices are important for binding to LIMP-2, we substituted single amino acids within this helical motif by replacing conserved hydrophobic leucines with negatively charged glutamic acids (FIG. 1B, C). This resulted in the three GC mutants: L91E (helix 1a), L94E (helix 1a) and L156E (helix 2). A R211E GC mutant served as a control since this mutation is located outside the identified hydrophobic helical motif (FIG. 1B). Different GC mutants were expressed in cells and assayed for their ability to bind LIMP-2 by co-immunoprecipitations (co-IP). In contrast to wild-type GC and the control mutant R211E, the three point mutations within the helical motif of GC impaired co-IP with LIMP-2 (FIG. 1D, E). Immunofluorescence studies demonstrated co-localization of wild-type GC and the R211E mutant with endogenous LIMP-2 (FIG. 1F, G) and the lysosome-associated membrane glycoprotein 2 (LAMP-2) (FIG. 4D, E) in lysosomes, whereas the GC helical motif mutants L91E, L94E and L156E remained in the ER (FIG. 4F, G). Furthermore a co-localization of wild-type GC with overexpressed LIMP-2 was also found in lysosomes, which was significantly reduced upon expression of the GC mutants L91E and L156E (FIG. 4H, I). To further evaluate the cellular fate of the GC helical motif mutants, we used GC-deficient mouse embryonic fibroblasts (MEFs) (FIG. 1H, I) and murine neuroblastoma cells (N2a) (FIG. 4J, K) for Endoglycosidase H (EndoH) and Peptide-N-Glycosidase F (PNGaseF) treatment of cellular extracts. Whereas PNGaseF removes all asparagine (N) linked glycans from GC and served as a control to detect unglycosylated GC, EndoH discriminates between mature (EndoH insensitive) and immature N-glycans (EndoH sensitive). Thus, complete EndoH sensitive bands indicate ER localization of GC. Overexpression of wild-type GC in GC-deficient MEFs and N2a cells resulted in a small fraction of post-ER forms of GC (FIG. 1H, 4J, see EndoH treated sample in second lane). Co-expression of LIMP-2 caused a tenfold increase in the post-ER form of wild-type GC (FIG. 1H (lane 5), 1I and FIG. 4J (lane 5), 4K). In contrast, LIMP-2 overexpression did not alter the post-ER levels of the GC helical motif mutants L91E and L156E and only to a minor degree the L94E GC mutant (FIG. 1H, I and FIG. 4J, K). This indicates some residual interaction of LIMP-2 with the L94E mutant under more native cellular conditions. The residual interaction found here was not detected by the previous co-IP experiments (FIG. 1D, E), possibly due to the stringency of the applied co-IP buffer. We then evaluated if the observed increase in GC maturation also leads to changes in its enzymatic activity. Upon co-expression of wild-type GC and LIMP-2 we observed a significant increase in GC activity, which was not evident for the three GC helical motif mutants L91E, L94E and L156E (FIG. 4L). Overall our data suggest that the hydrophobicity of a three helix motif within GC is critical for proper LIMP-2 binding. Furthermore, LIMP-2 expression appears to be a limiting factor for ER exit and post-ER trafficking of GC.

Identification of GD-Causing Mutations within the Three Helix Motif of GC and their Interference with LIMP-2 Binding.

Figure 2:
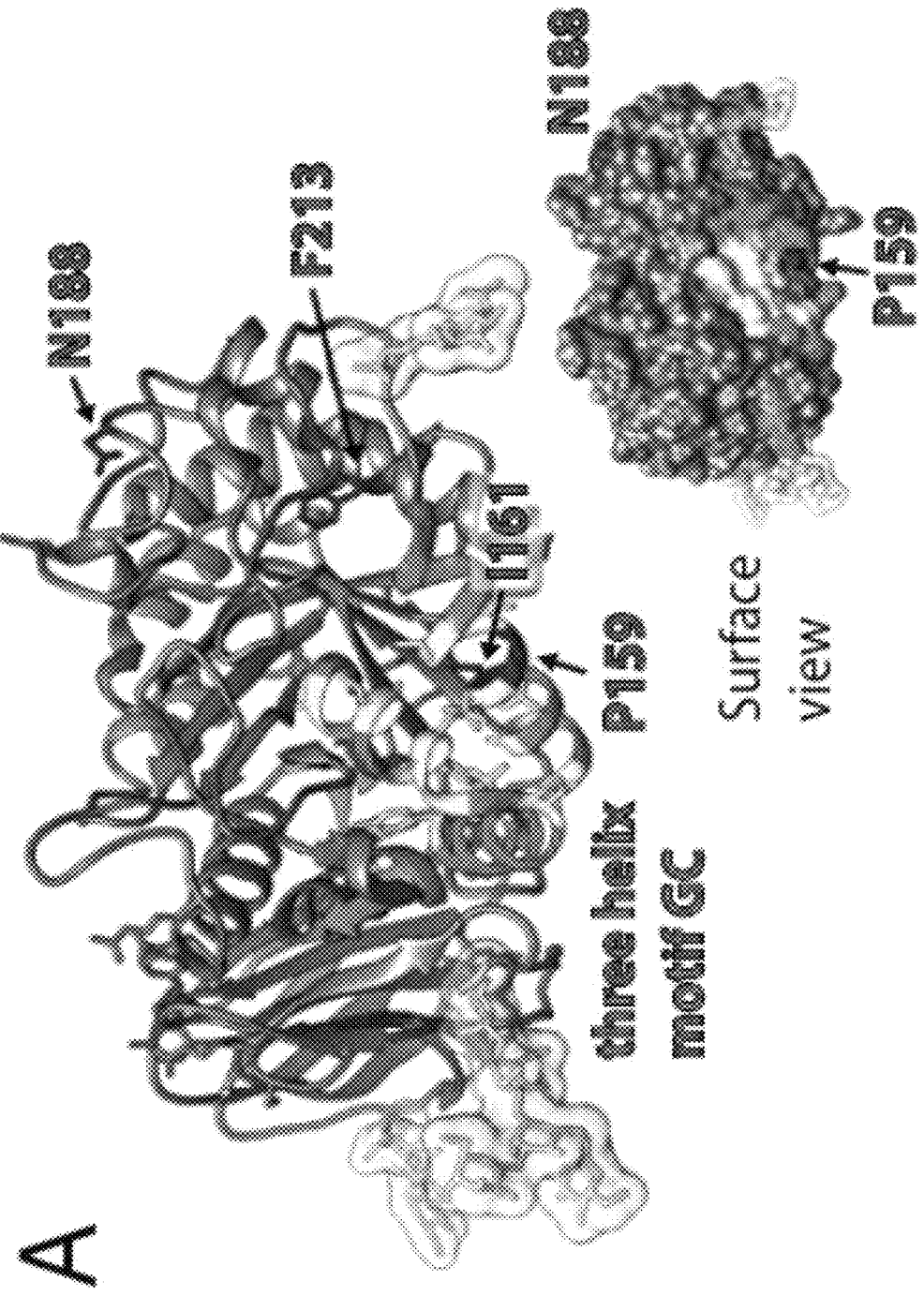
FIG. 2: Analysis of the LIMP-2 interaction site in GD patient mutants. A) Structure of GC (PDB: 2J25); helical motif and hydrophobic amino acids are highlighted in red and yellow, respectively. The clinically relevant GD mutants P159L and I161S (located in helix 2) and F213I and N188S (outside the helical motif) are depicted in blue. A surface view shows surface exposure of indicated amino acids. B) Co-IP of GD patient mutants P159L, I161S, F213I and N188S (α-hGC) expressed in N2a cells. A LIMP-2 antibody was used for IP (# identifies antibody band; AB ctrl=antibody control). Dotted line indicates different exposure times of the same immunoblot. C) Densitometry of co-IP studies (normalized to LIMP-2 (n=4-11)). D) Immunofluorescence co-staining of GD patient mutants (α-hGC; red) expressed in GC-deficient cells with endogenous LIMP-2 (green). Area of magnification is indicated by a white box. E) Pearson's index give the degree of GC-LIMP-2 co-localization (n=β-10). F) Immunoblot and G) densitometric quantification of GD patient mutants (α-hGC) with and without co-expression of LIMP-2 in GC-deficient cells treated with EndoH or PNGaseF (postER/ER ratio normalized to WT GC (n=3)). The upper, EndoH resistant band of GC indicates post-ER location of the protein, whereas the lower band corresponds to ER residence. H) Co-IP of L91A and GD patient mutant P159T overexpressed in N2a cells (α-hGC). Dotted line indicates different exposure time of same immunoblot. I) Quantification of bound GC protein normalized to precipitated LIMP-2 (n=4-5). J) Binding model of LIMP-2 and GC with potential stabilizing interaction of carbohydrate chains of both proteins (dotted lines). See also FIG. 5.
Figure 2:
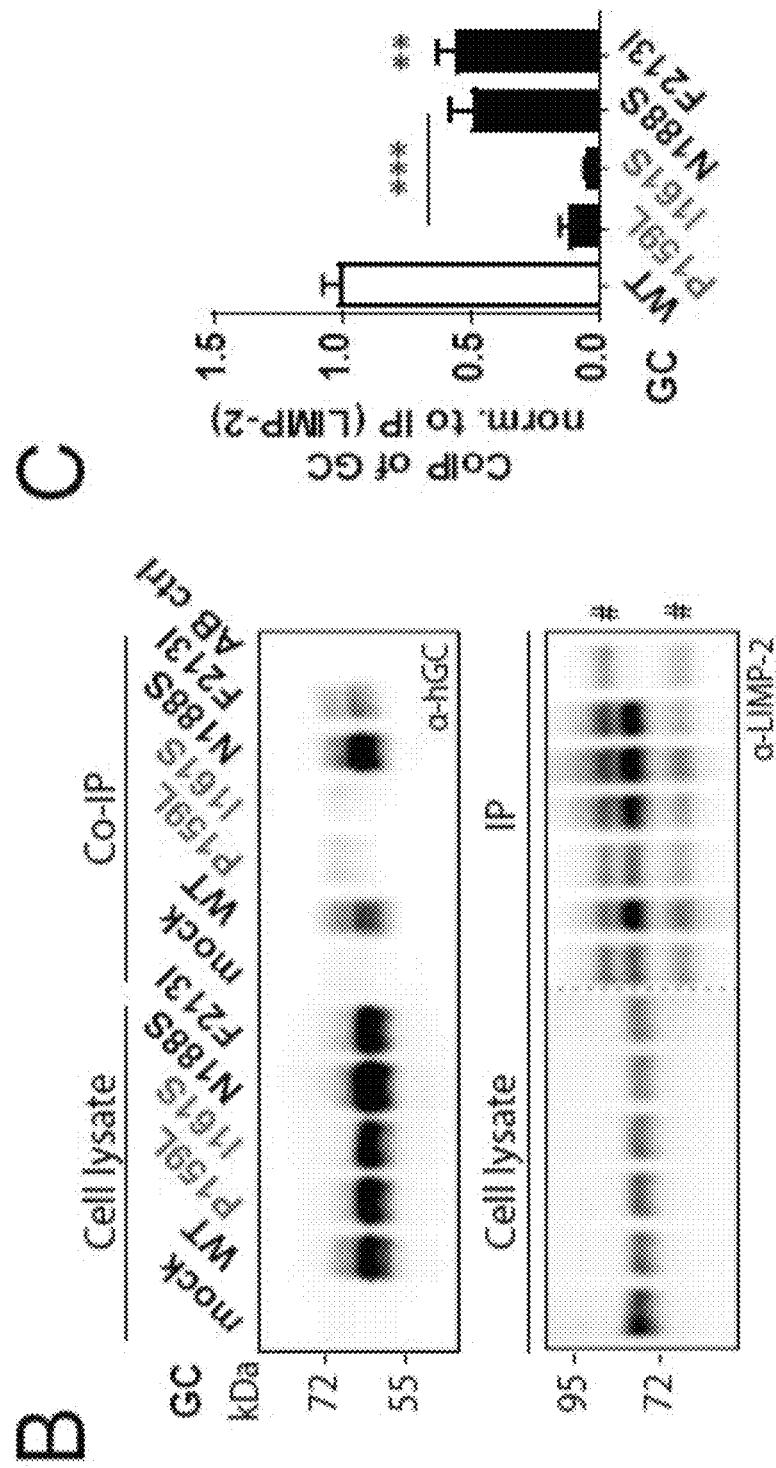
Figure 2:
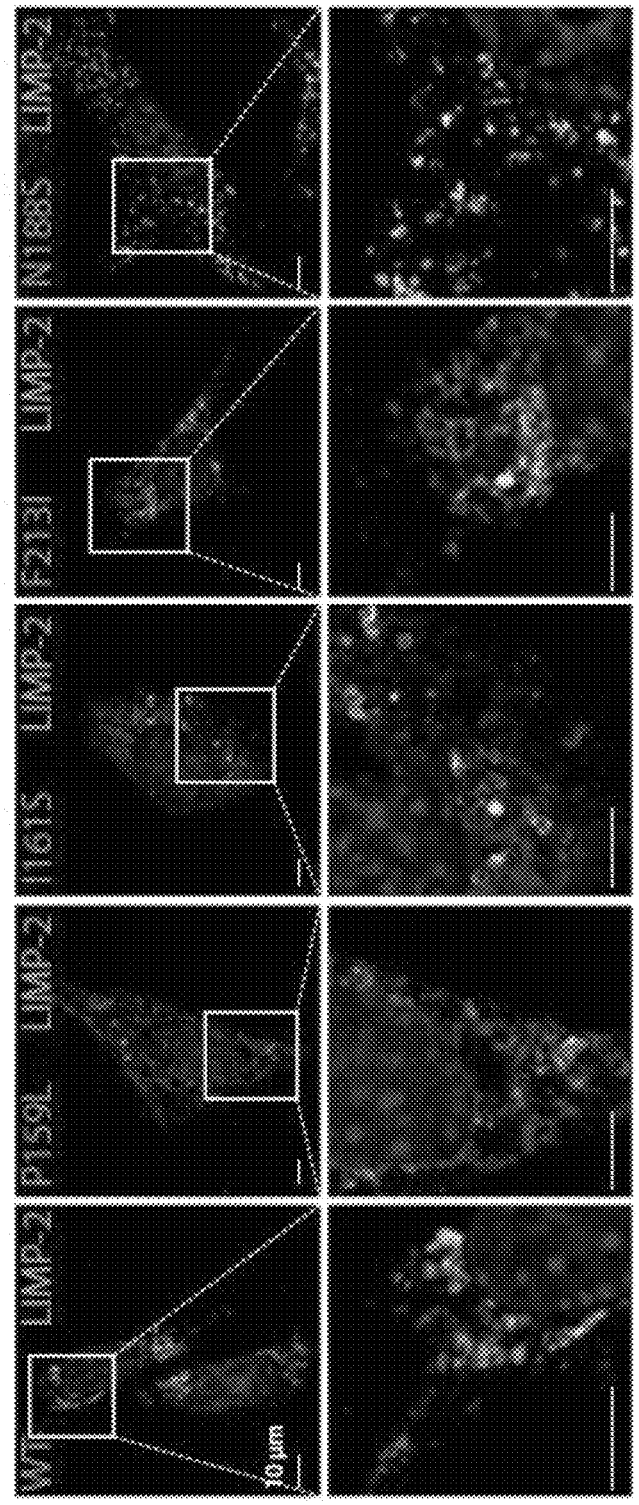
Figure 2:
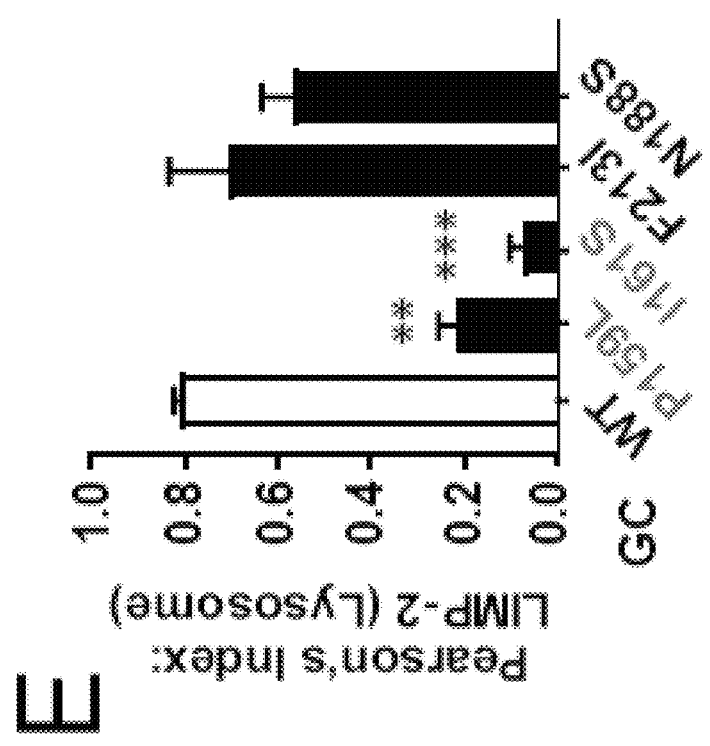
Figure 2:
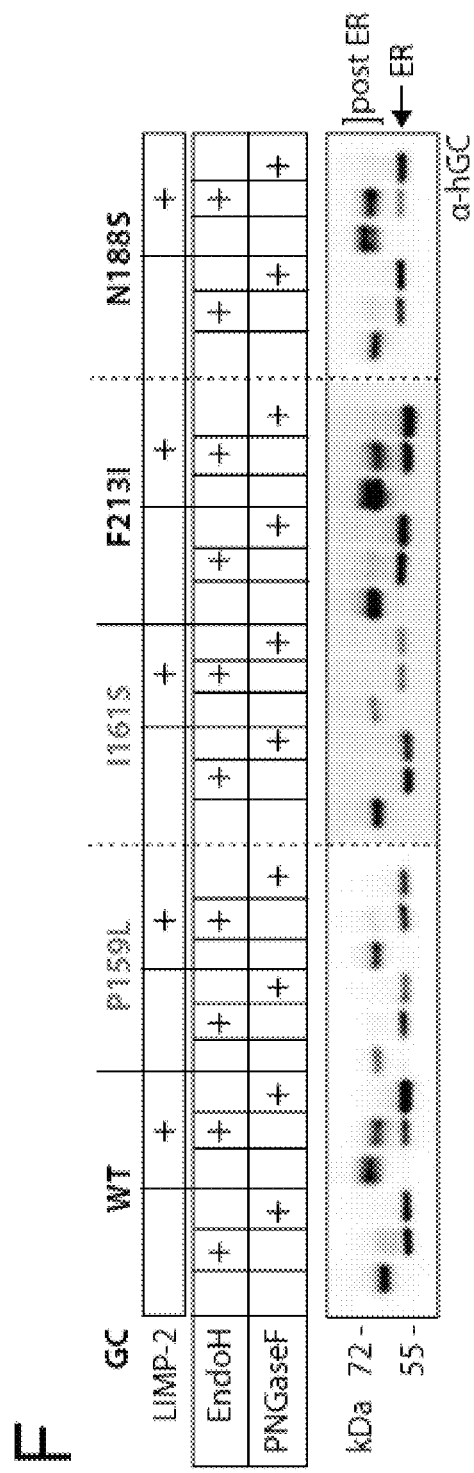
Figure 2:
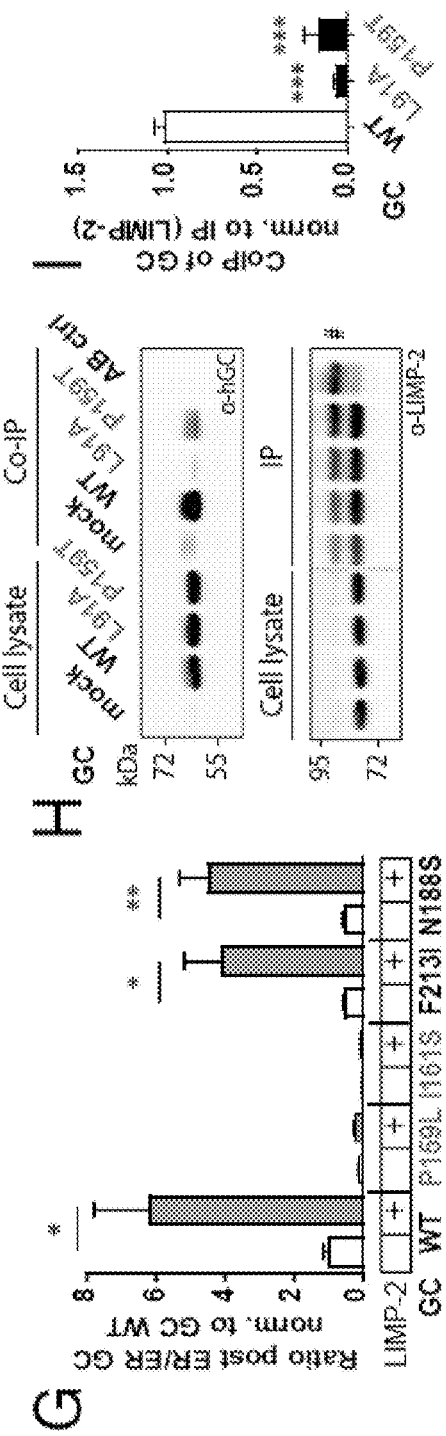
Figure 2:
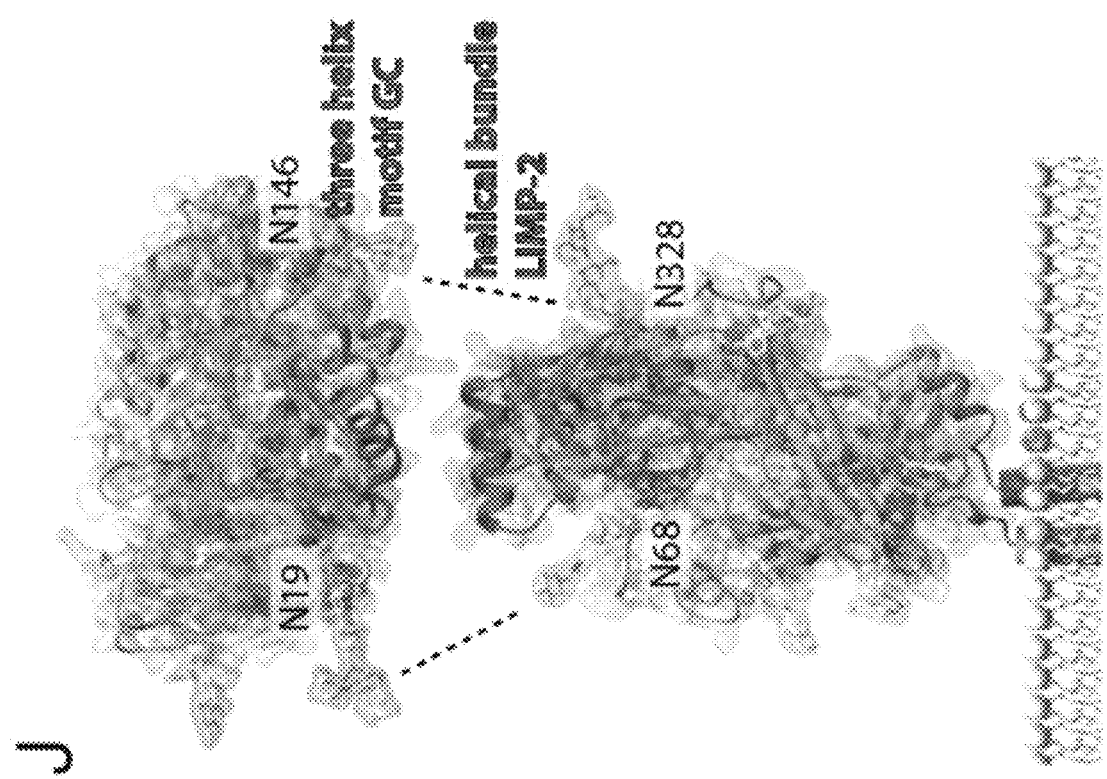
Figure 5:
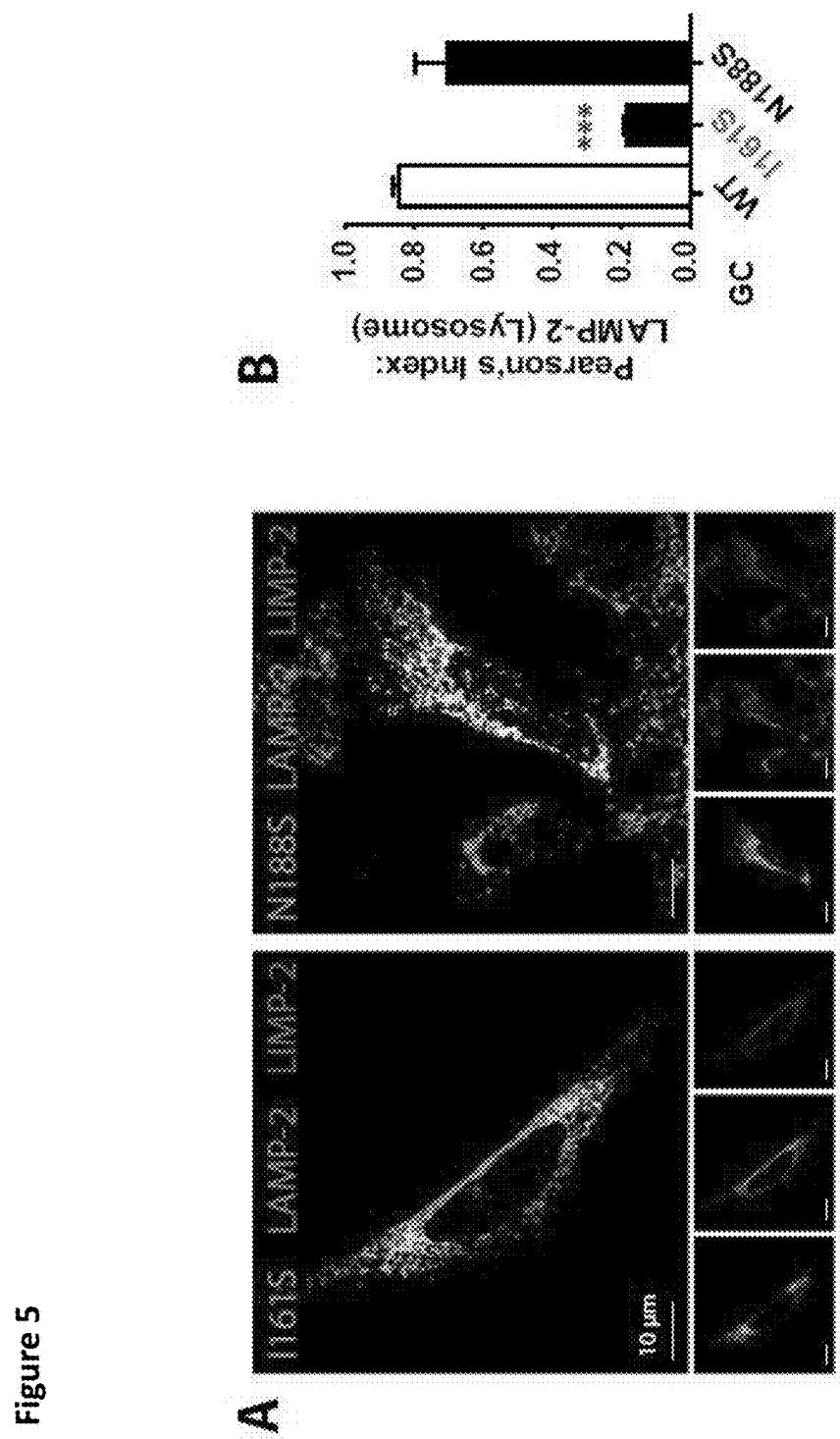
FIG. 5: Analysis of GD patient mutants and their LIMP-2 binding behavior. A) Immunofluorescence staining of GC mutants (α-hGC, red) co-expressed with LIMP-2 (α-myc; green) in GC-deficient cells. Area of magnification is indicated by a white box. B) Co-localization of GC and LIMP-2 was analyzed by Pearson's index (n=β-7). C) Triple-immunofluorescence staining of GC-deficient cells transfected with patient GC mutants (α-hGC, green) and endogenous lysosomal markers LAMP-2 (red) and LIMP-2 (blue). A purple color indicates a co-localization of LAMP-2 with LIMP-2 and a white signal (upper panel) points to an additional overlay with GC indicating lysosomal localization of the respective GC construct. D) Pearson's Index of co-localization of GC-patient mutants (I161S and N188S) with LAMP-2 (n=2-3). The respective GC wild-type control can be found in FIG. 4D. E) Immunofluorescence of GC-deficient cells transfected with GC mutants (α-hGC; red) and co-stained for the endogenous ER marker PDI (green). Area of magnification is indicated by a white box. F) Analysis of co-localization of GC mutant with PDI shown as Pearson's Index (n=2-6). G) Immunoblot of expression level of all analyzed GC mutants (α-hGC) in N2a cells normalized to GC WT. H) Interaction model of LIMP-2 (PDB: 4F7B, 4Q4F) and GC (PDB: 2J25) showing pH-dependent structural differences between pH 7.5 and pH 5.5. A One-Way ANOVA together with a subsequent Tukey-Kramer post-hoc test was used for statistical analyses. \*\*; \*\*\* denote p<0.01; 0.001 showing comparison to GC WT.
Figure 5:
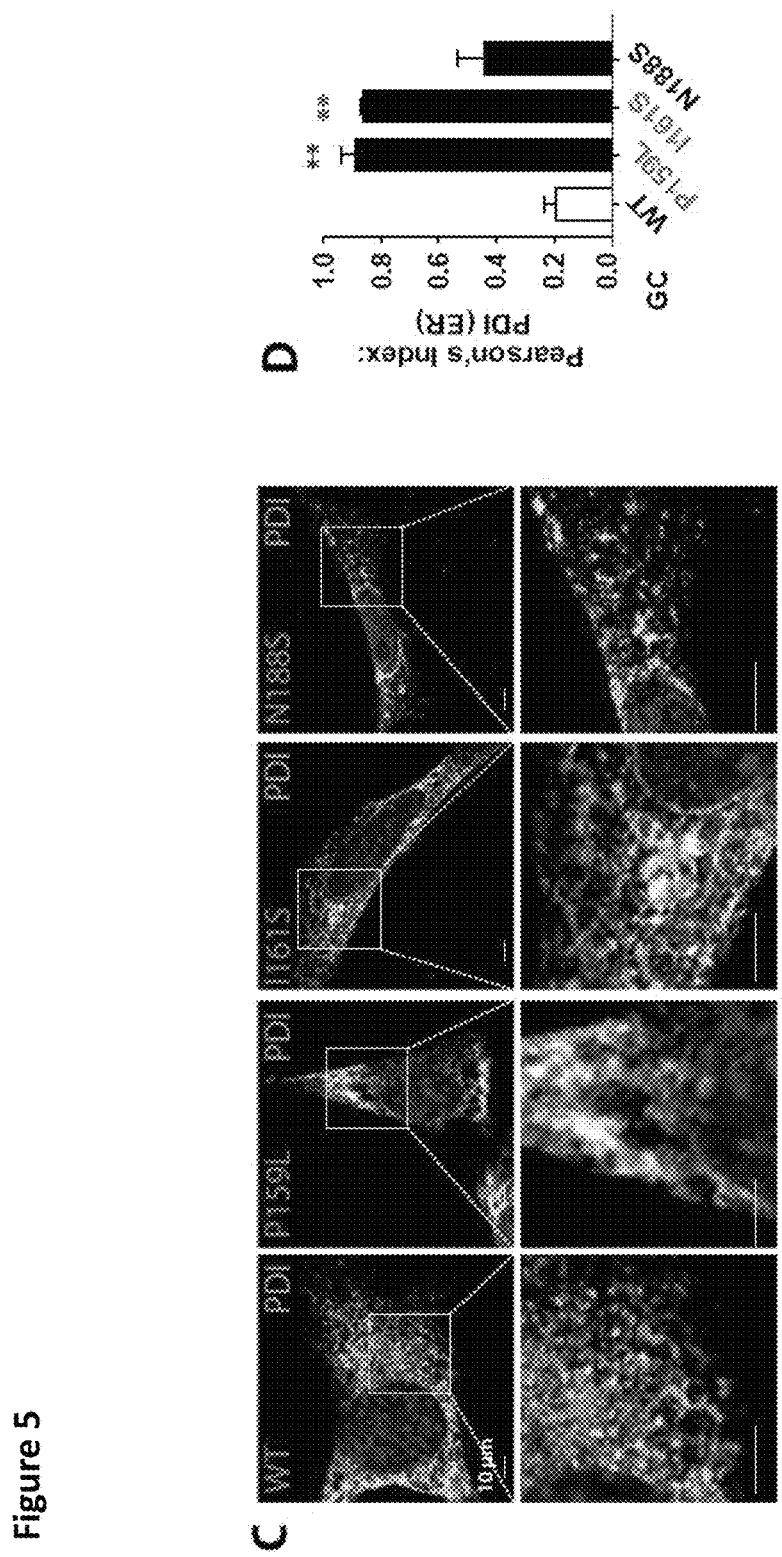
Figure 5:
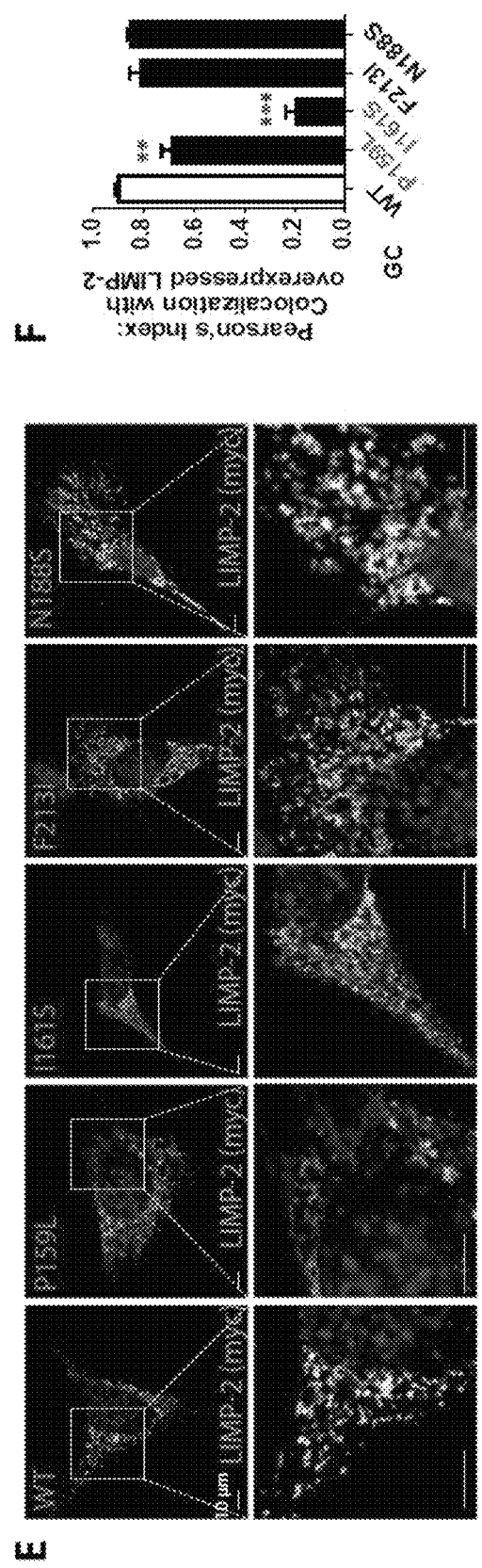
Figure 5:
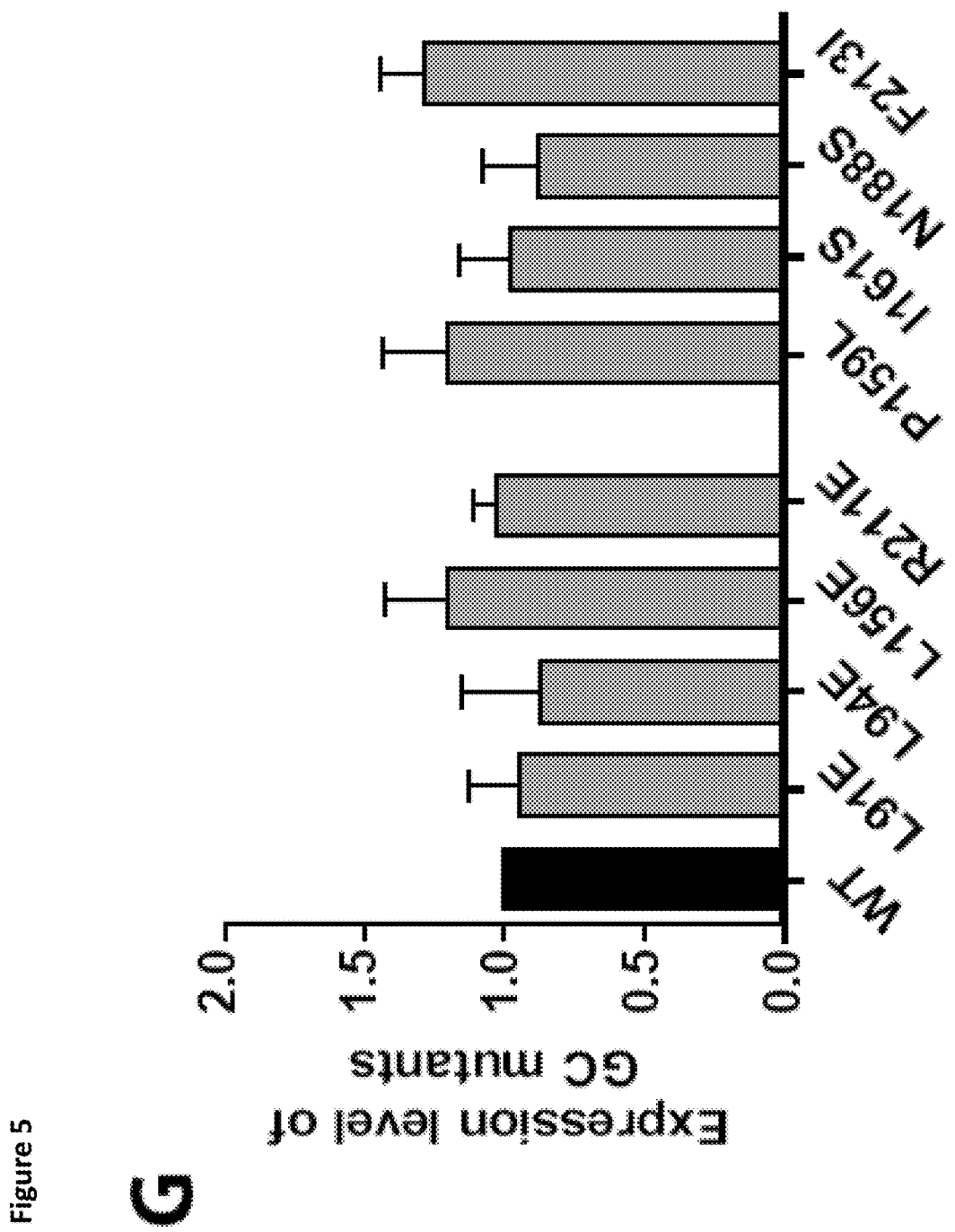
Figure 5:
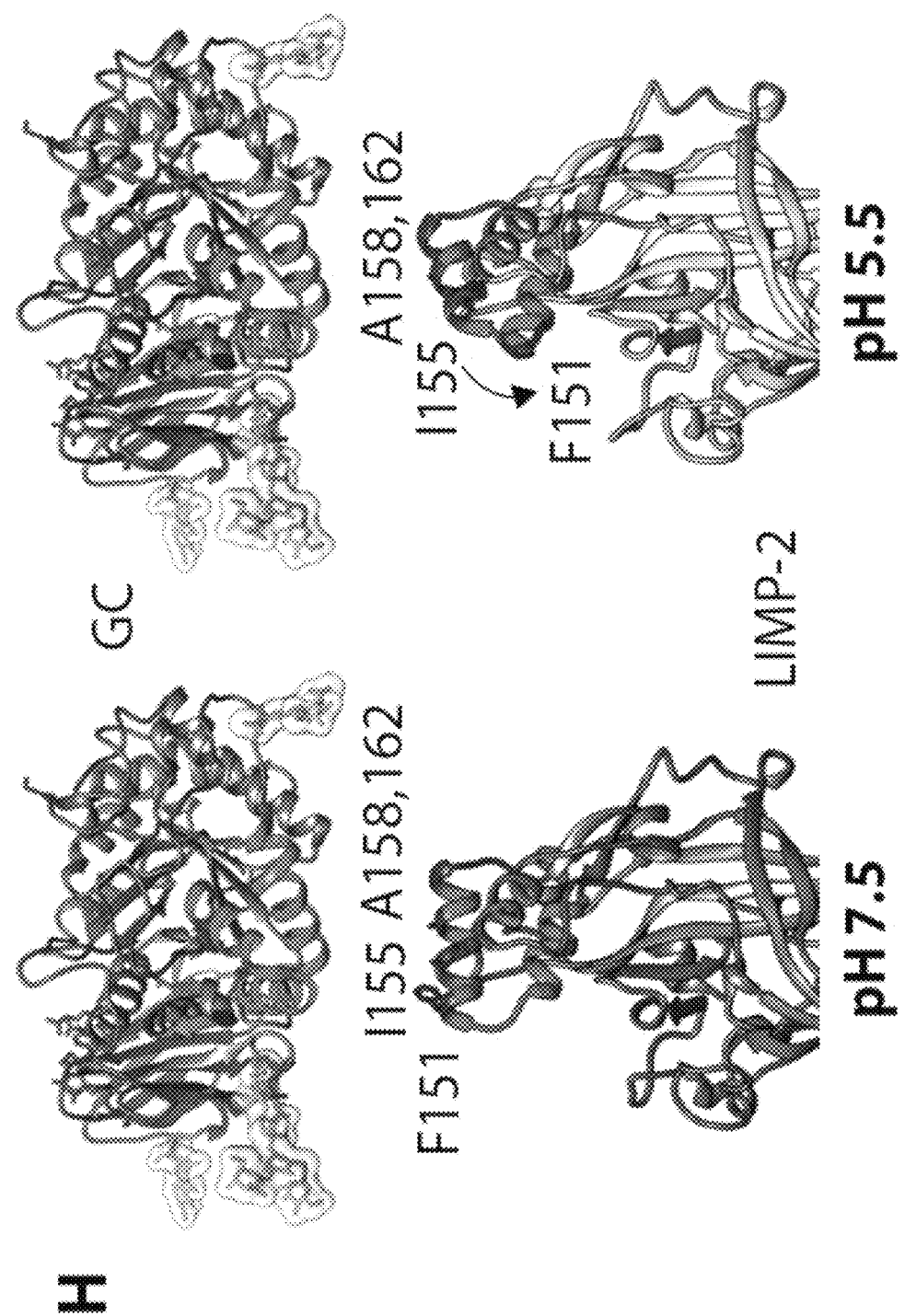

To evaluate if GD-associated mutations within the potential binding motif of GC might interfere with LIMP-2 interaction, we analyzed two GD mutants: P159L and I161S. Both mutations are located within helix 2 of the hydrophobic helical interface (FIGS. 1C and 2A) (5, 18). As a control, we used two additional GD patient mutants (F213I and N188S) (5, 19), which reside outside of the hydrophobic helical motif of GC and thus should not interfere with LIMP-2 interaction (FIG. 2A). First, we analyzed LIMP-2 binding of these mutants and second the LIMP-2-dependent intracellular transport of GC. Co-IP experiments revealed impaired binding of the GC mutants P159L and I161S to LIMP-2 when compared to wild-type GC (FIG. 2B, C). The two control mutants F213I and N188S still bound to LIMP-2 albeit to a reduced extent compared to wild-type GC (FIG. 2B, C). Immunofluorescence microscopy in GC-deficient cells demonstrated decreased lysosomal transport of the hydrophobic helix mutants P159L and I1161S (FIG. 2D, E; 5A, B). In contrast the two control mutants F213I and N188S still co-localized with LIMP-2 (FIG. 2D, E) and LAMP-2 (FIG. 5A, B) indicating their lysosomal localization. Furthermore, co-localization with PDI revealed increased ER localization of the two GD mutants P159L and I161S when compared to wild-type GC or the control mutant N188S (FIG. 5C, D). In addition the two GD-associated helix mutants (P159L, I161S) showed significantly reduced co-localization with overexpressed LIMP-2, whereas the control mutants (F213I, N188S) did not (FIG. 5E, F). An EndoH digest confirmed the retention of the clinical mutants P159L and I161S within the ER, whereas the GC mutants F213I and N188S were found in post-ER fractions (FIG. 2F, G). In addition, overexpression of LIMP-2 did not increase post-ER transport of the P159L and I161S mutants as observed for the F123 and N188S mutants (FIG. 2F, G) strengthening our hypothesis that both mutants are incapable of binding to LIMP-2 via their hydrophobic helical motif resulting in decreased ER exit and lysosomal transport.

To further characterize the LIMP-2-binding domain, we analyzed two additional GC mutants. The GD-associated point mutation P159T, which carries a polar threonine at position 159 and the L91A mutant, carrying an alanine at position 91, which represents an hydrophobic amino acid but with a less bulky side chain as the original leucine. Both mutations resulted in impaired binding of mutated GC to LIMP-2 as revealed by co-IP studies (FIG. 2H, I), further indicating the importance of single amino acids for LIMP-2 binding in this highly conserved region. Importantly, all GC mutants analyzed so far in this study exhibited comparable expression levels with the wild-type enzyme (FIGS. 1D and 2B (upper blots), 5G).

In summary, our findings suggest that the LIMP-2-binding region in GC is located in a helical interface formed by helix 1a (residues T86-L96), helix 1b (residues P99-S110) and helix 2 (P150-A168), displaying a similar hydrophobic patch as found in LIMP-2. Therefore we propose a model in which GC and LIMP-2 interact via two hydrophobic helical interfaces (FIG. 2J, 5H). Consistent with this model, a crystal structure of LIMP-2 solved at pH 5.5 (20) shows a large conformational change in the identified binding site of helix 5, that is likely responsible for the dissociation of GC at low lysosomal pH (FIG. 5H).

A Synthetic LIMP-2-Derived Peptide is Sufficient to Interact with GC and Increases the Enzymatic Activity.

Figure 3:
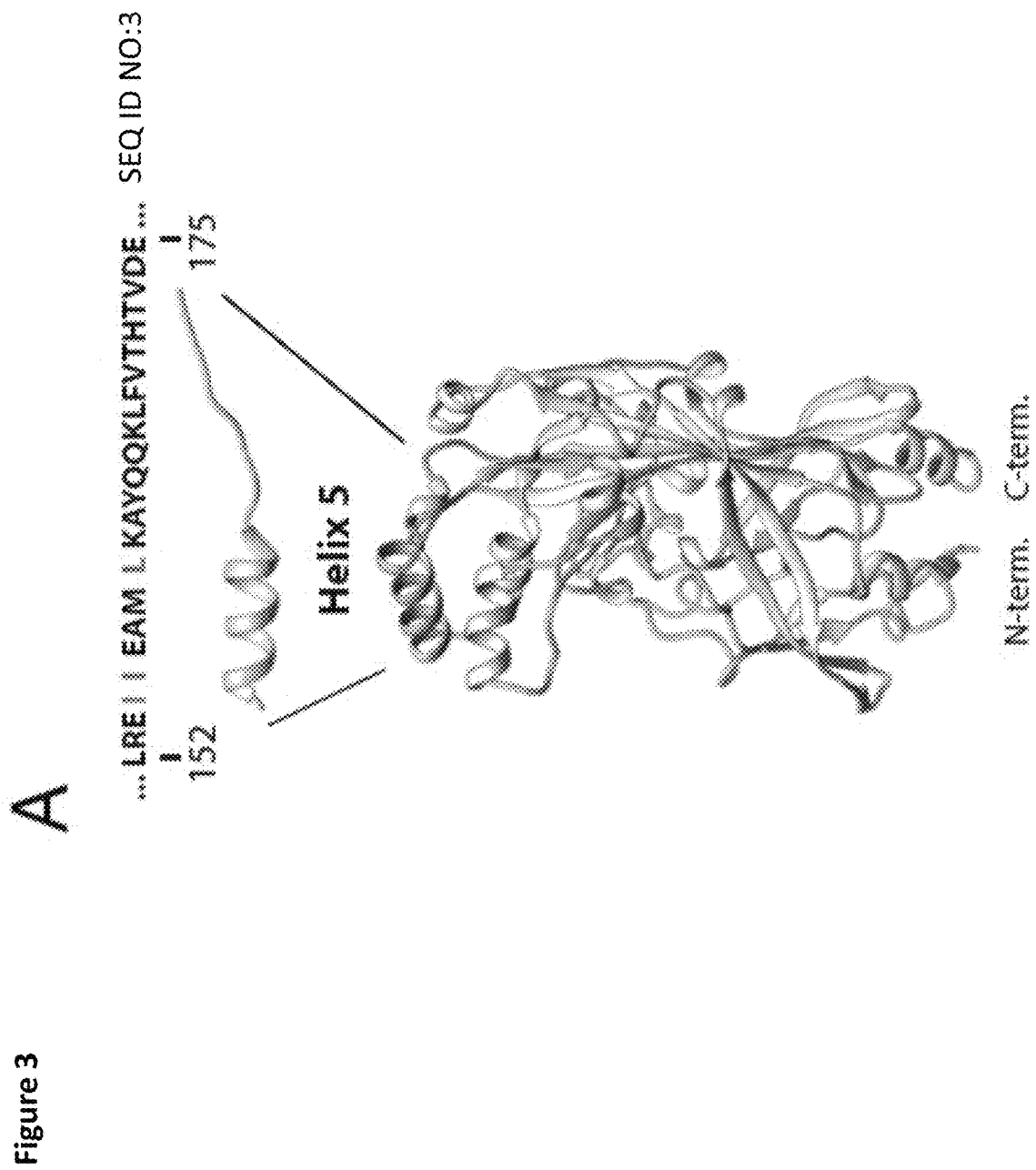
FIG. 3: Structural characteristics of LIMP-2-derived peptide comprised of helix 5 and its effect on GC function. A) Protein structure of LIMP-2 (PDB: 4F7B) with helix 5 peptide sequence (L152-E175) highlighted. Amino acids in red were substituted with aspartic acid (3×D). B) Pulldown and C) densitometry of recombinant GC bound to peptides (helix 5 or 3×D) relative to bound protein fraction of buffer control (n=4-5). Proteins were visualized by coomassie staining (CBB). D) Immunoblot of endogenous GC in Cos 7 cells (α-hGC) after pulldown with helix 5 peptide. E) GC activity assay of recombinant GC incubated with helix 5 or 3×D peptide (n=4). F) Stabilization assay of GC mixed with buffer, helix 5 or 3×D peptide incubated at 37° C. for 270 hours (n=3). G) Lysosomal GC activity of living H4 cells measured in vivo after incubation with uptake-optimized TAT-peptides (helix 5 and 3×D). GC activity was normalized to cell volume and is shown relative to buffer control (n=4). H, I) TAT-peptide uptake (helix 5 and 3×D) in H4 cells, stably overexpressing α-synuclein (α-syn) under a tetracycline inducible promoter in conjunction with doxycycline to stop α-synuclein de novo synthesis. (H) Immunoblot and (I) densitometry analysis of α-synuclein level (normalized to loading control) after 74 hrs of incubation with helix 5 TAT-peptide. The value at incubation time $t_0$ was set as 1 (n=6). J) Pulldown of recombinant wild-type (WT) GC and GC N370S mutant with TAT-peptides (helix 5 and 3×D). K) Activity assay of recombinant mutant N370S GC after incubation with TAT-peptides (helix 5 and 3×D). As a reference value GC WT activity is shown on the right. GC activity was normalized to buffer control (n=β-5). See also FIG. 6.
Figure 3:
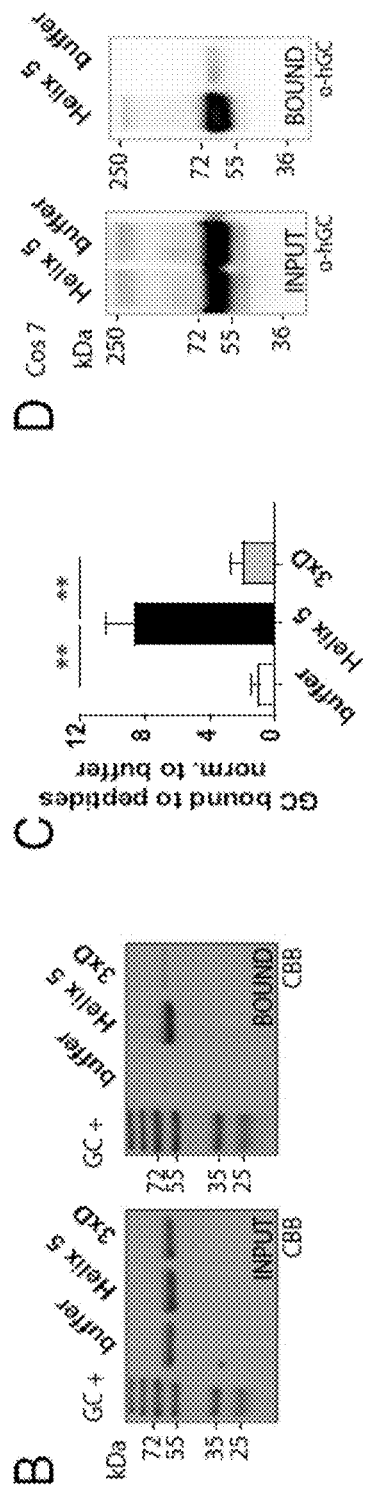
Figure 3:
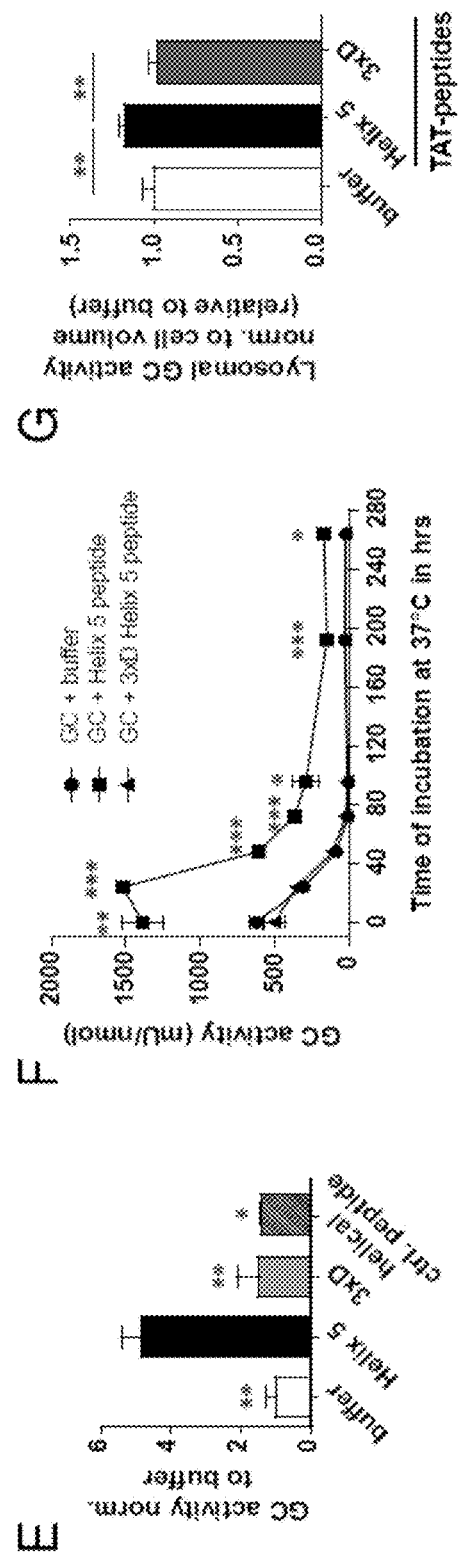
Figure 3:
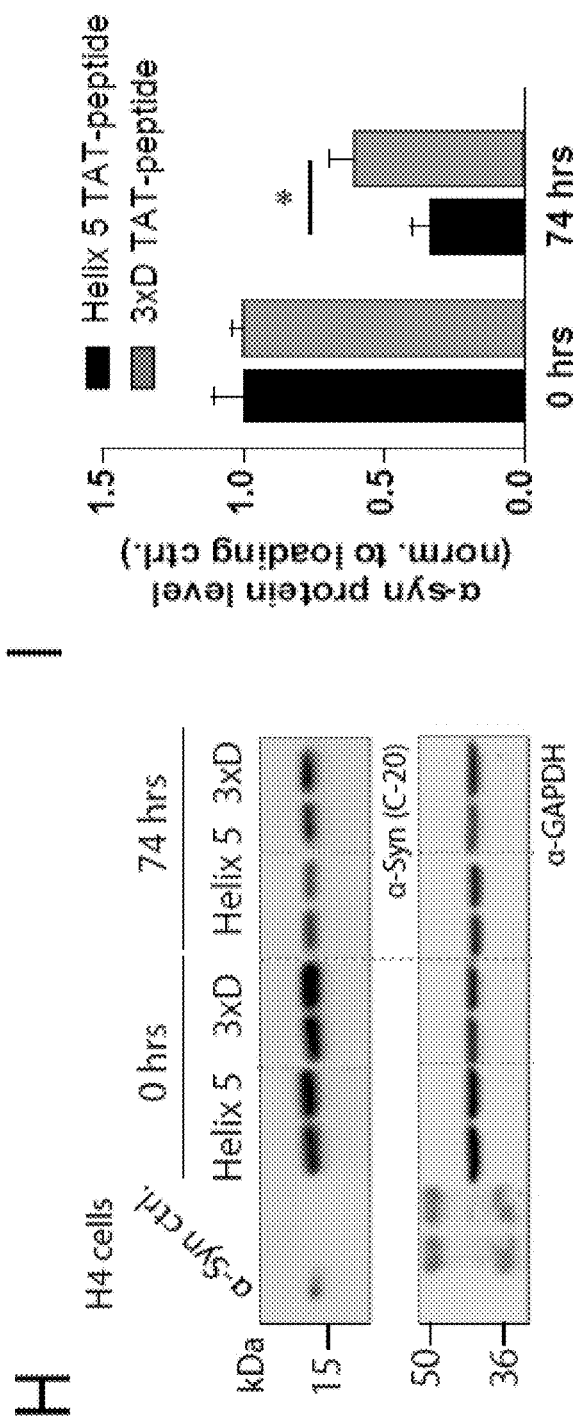
Figure 3:
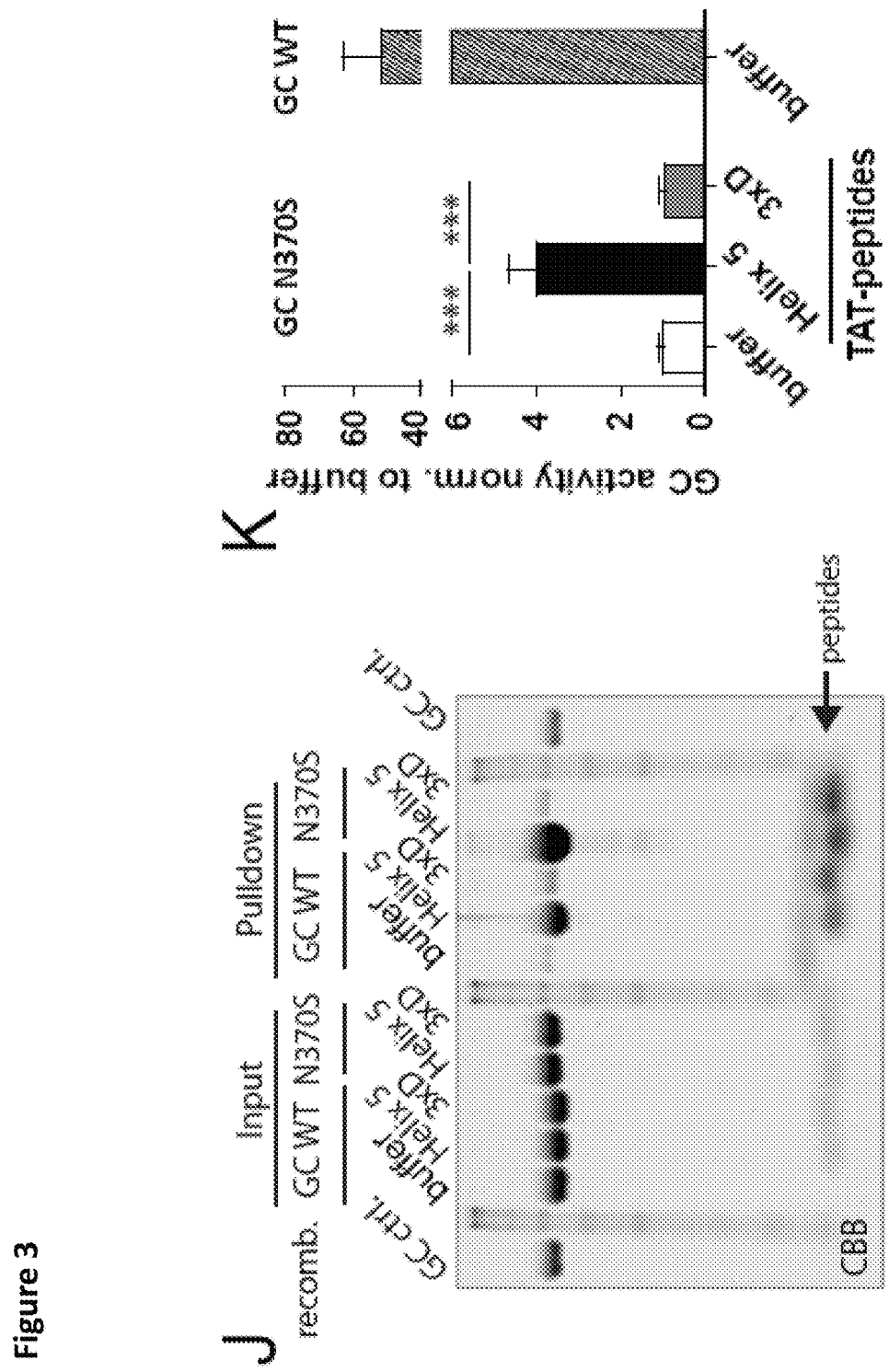
Figure 6:
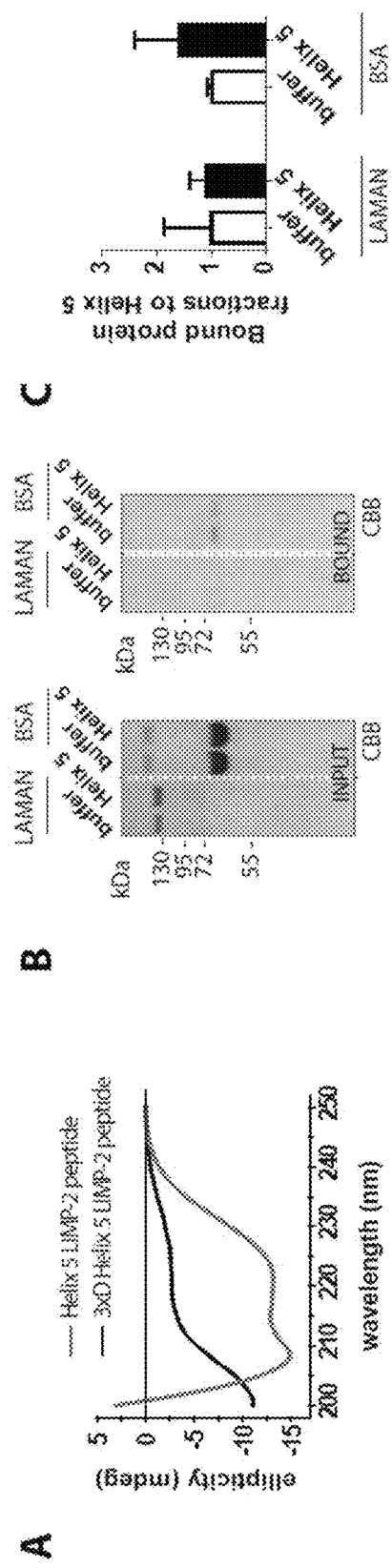
FIG. 6: Characterization of a helical LIMP-2-derived peptide. A) CD-spectra (250-200 nm) exhibiting a helical fold for the helix 5 peptide that is absent in the control 3×D helix peptide. B) In vitro peptide pulldown assay: helix 5 peptides were incubated with recombinant LAMAN and bovine serum albumin (BSA). INPUT and BOUND fractions were loaded onto SDS-PAGE and proteins visualized by coomassie staining (CBB). C) Densitometry of LAMAN and BSA protein bound to peptide, normalized to protein fraction bound to beads only (buffer; n=2-3). D) and E) Activity assay of recombinant (D) GC and (E) LAMAN incubated with different excess molarities (1×-10×) of helix 5 peptide (n=β-5) and LIMP-2 ectodomain (n=4). GC activities were normalized and statistical analyses compared to 0 input of BSA/helix 5 peptide. F) Peptide-pulldown of GC constructs overexpressed in N2a cells with subsequent Western blot analysis (α-hGC) utilizing helix 5 and the 3×D control peptide as a negative binding control. G) Densitometry of GC protein bound to peptides; each construct is normalized to buffer only. H) Live-cell lysosomal GC activity of H4 cells after uptake of helix 5 and 3×D TAT peptides. GC activity was measures every 30 minutes up to 3.5 hours. Cells were treated with DMSO or the "lysosomal inhibitor" bafilomycinA1. The area under the DMSO curve (AUC) shows whole cell activity. Lysosomal activity is calculated by subtracting the AUC of DMSO with the AUC of bafilomycinA1 treated samples (n=4). I) Whole cell GC activity of H4 cell lysate after uptake of helix 5 peptide and the control 3×D TAT peptide as shown in the assay of FIG. 4K. GC activity was measured from 16-74 hours and is shown in mU/mg (n=3). A One-Way ANOVA with a subsequent Tukey-Kramer post-hoc test was applied in subpanel H and a two-sided Student's t-test was used for analysis in D and G. \*, \*\*and \*\*\* denote p<0.05, 0.01 and 0.001, respectively. J) Enhancement of GC activity persists for a 74 hrs time course with the helix 5 TAT-peptide but not with the control 3×D TAT-peplide. K) Localization of the N370S mutation outside of the three helical LIMP-2 binding molif.
Figure 6:
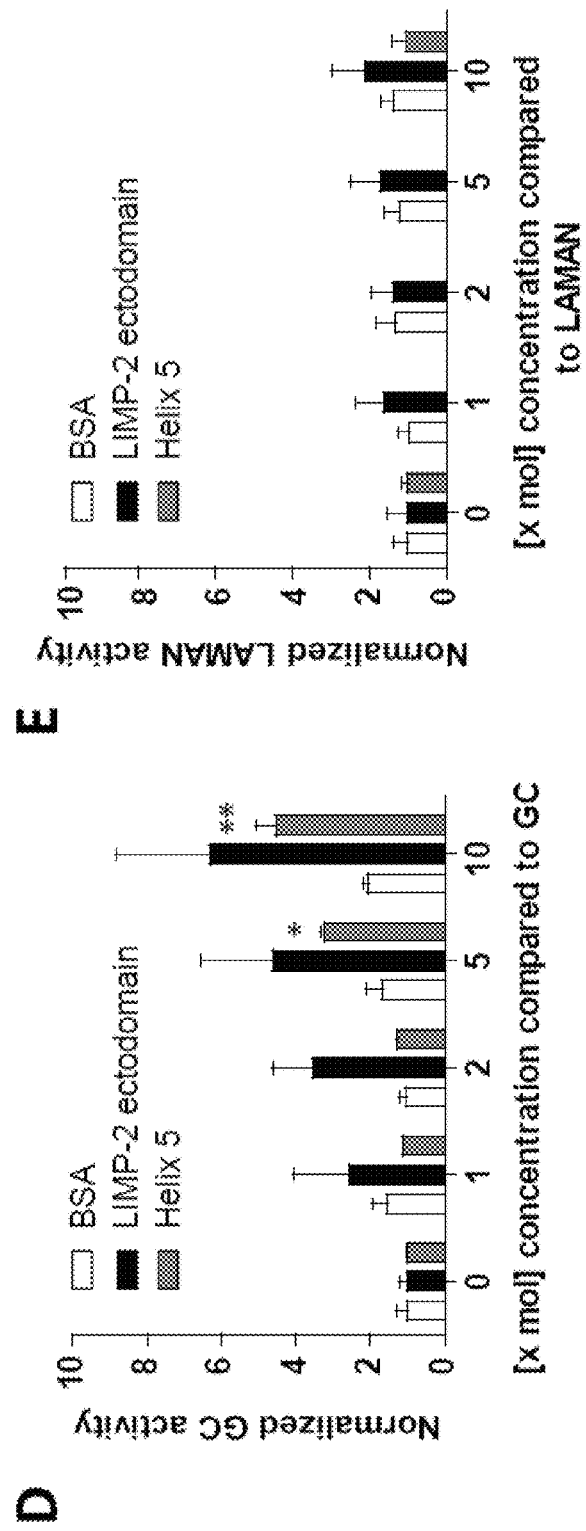
Figure 6:
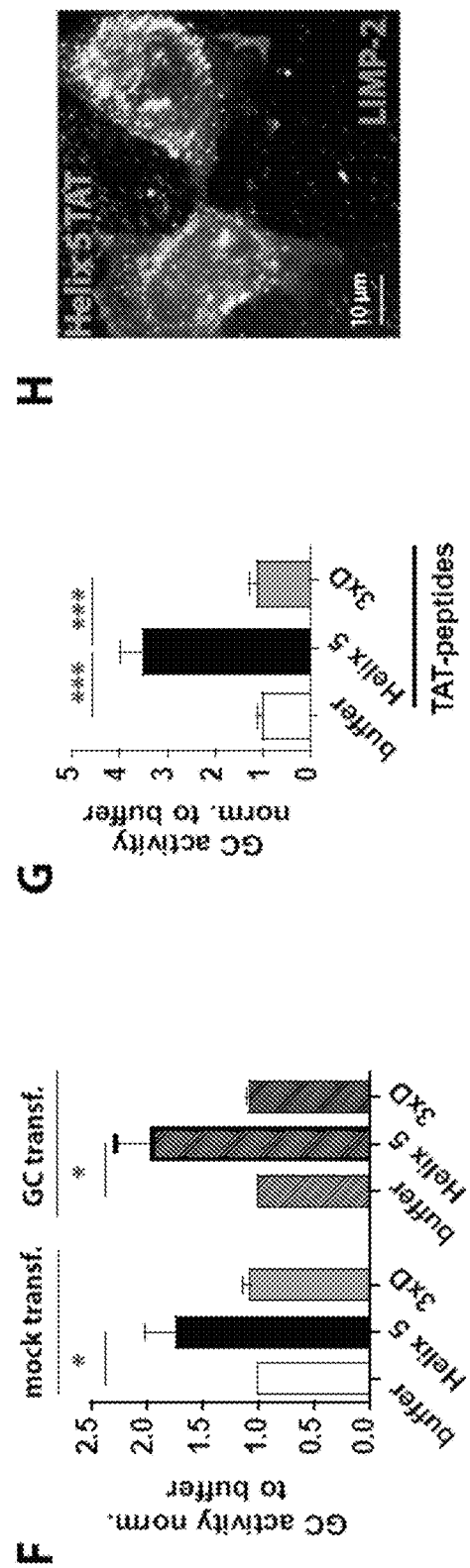
Figure 6:
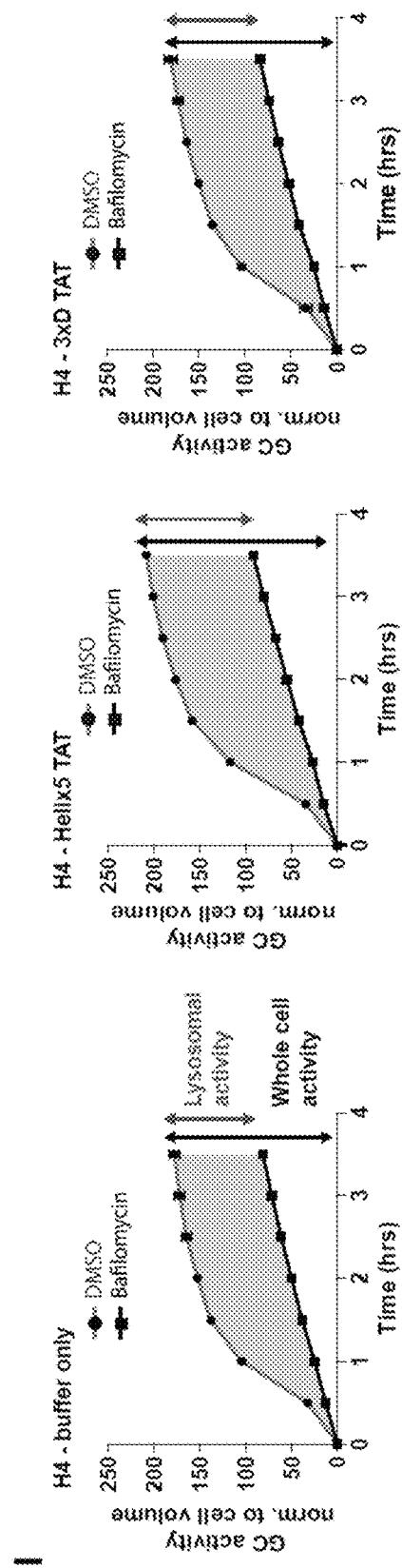
Figure 6:
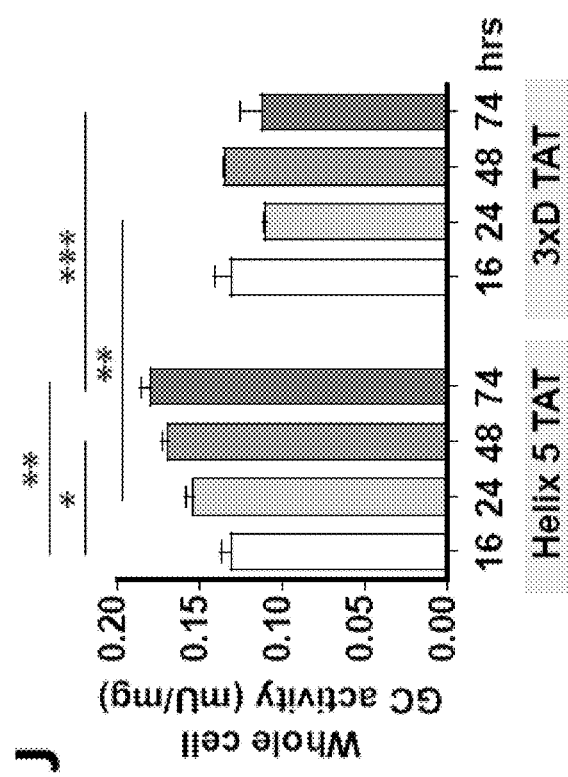
Figure 6:
Figure 7:
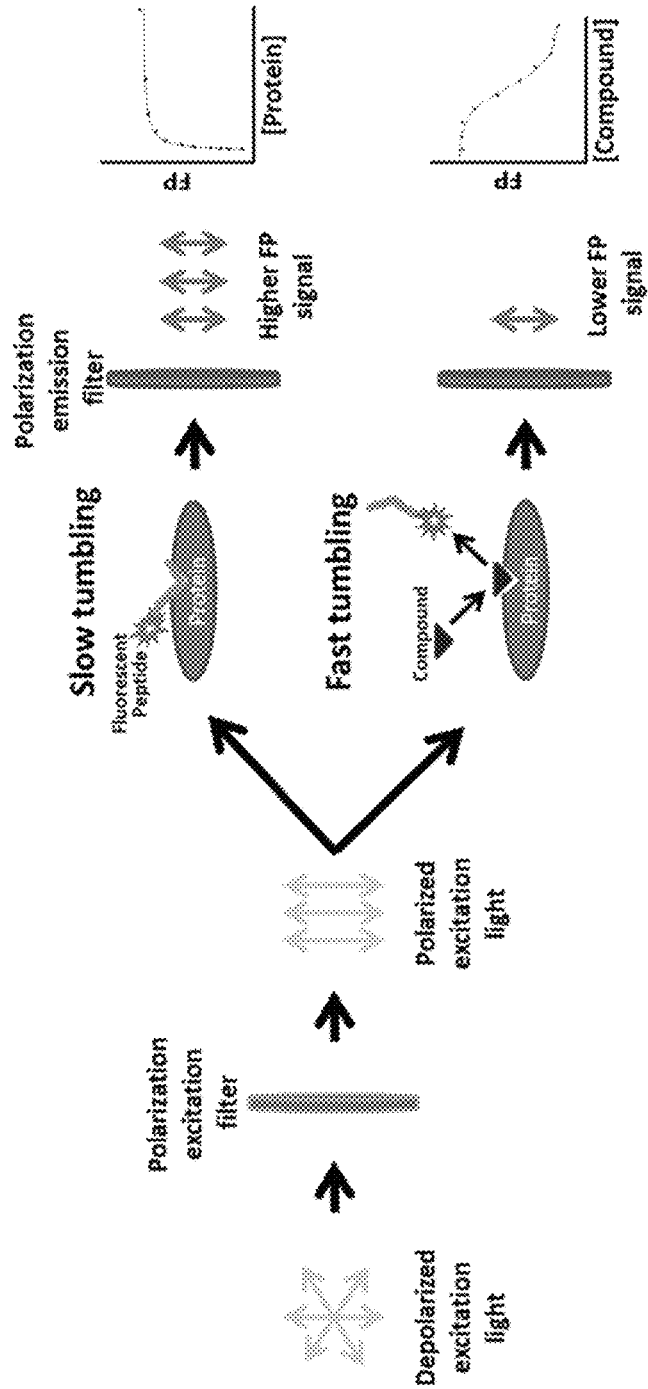
FIG. 7: Illustration of one embodiment of a fluorescence polarization (FP) assay for detecting binding of the helix 5 peptide and β-glucocerebrosidase and for identifying compounds that inhibit binding of the helix 5 peptide and β-glucocerebrosidase. FP-binding assays can, in principle, be used quantitatively to analyze binding of any small soluble fluorescent molecule (and any soluble ligand that competes with it) to a larger soluble protein. The identified compounds in the FP assay further may be tested to determine whether the identified compounds modulate the biological activity of β-glucocerebrosidase (e.g., via increasing the biological activity of β-glucocerebrosidase in regard to hydrolysis of glycosylceramide).
Figure 8:
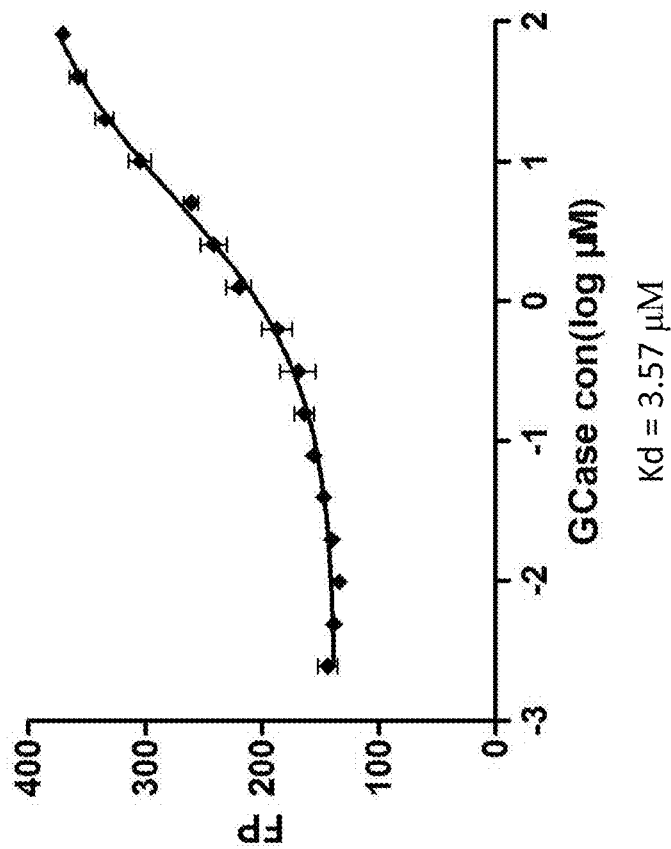
FIG. 8: Detection of binding between fluorescently labelled LIMP-2 peptide and β-glucocerebrosidase. The measured $K_d$ was 3.57 µM.

We then asked if the most apically exposed helix 5 of LIMP-2 is sufficient for binding to GC. To this end, we generated a LIMP-2-derived helix 5 peptide together with a control peptide with two isoleucine and one leucine residues substituted by three aspartates (3×D; FIG. 3A). We have previously shown that a LIMP-2 mutant containing these three aspartates failed to bind GC (3). Circular dichroism spectroscopy confirmed the helical structure of the helix 5 peptide, whereas the control peptide was non-helical (FIG. 6A). Both peptides were N-terminally tagged with biotin and used for GC pulldown experiments at neutral pH. After incubation of the peptides with either recombinant GC (FIG. 3B, C) or cellular lysates (FIG. 3D) only the wild-type helix 5 peptide specifically co-precipitated recombinant as well as endogenous GC. In addition, no interaction of the helix 5 peptide with recombinant α-mannosidase (LAMAN), a lysosomal hydrolase or albumin (BSA) could be detected (FIG. 6B, C) demonstrating the specific interaction of this helix 5 peptide with GC.

To address the functional impact of the observed interaction between the helix 5 peptide and recombinant GC, we measured GC activity in the presence of a one- to tenfold molar excess of the helix 5 peptide. Enzyme activity was increased five times in the presence of a tenfold molar excess of the helix 5 peptide, whereas the 3×D control peptide did not increase the GC activity (FIG. 3E). A random helical control peptide consisting of 24 amino acids (21) was also not able to increase GC activity, further supporting the specificity of the helix 5 peptide (FIG. 3E). The purified luminal domain of LIMP-2 had a similar effect on GC activity (FIG. 6D), suggesting that the activating effect of LIMP-2 on GC is mainly mediated by helix 5. No effect on enzymatic activity after incubation with the helix 5 peptide or the LIMP-2 ectodomain could be found for recombinant α-mannosidase (LAMAN) further emphasizing the specificity of the helix 5 peptide on GC activity (FIG. 6E). The enzymatic activity of endogenous and overexpressed GC in cell lysates could also be increased after incubation with the helix 5 peptide (FIG. 6F). To analyze if the increase in GC activity is due to stabilization of the enzyme, recombinant GC was incubated with the helix 5 and the control peptide at 37° C. and the activity of GC was measured at regular intervals (FIG. 3F). Incubation of GC with buffer alone or the control 3×D peptide led to a complete loss of enzymatic activity within 72 hours (hrs), whereas GC still displayed significant enzymatic activity in presence of the helix 5 peptide (helix 5: $t_{1/2}$=48 hrs; 3×D: $t_{1/2}$=24 hrs) (FIG. 3F).

We also analyzed if the helix 5 peptide-mediated increase in GC activity measured in vitro could be detected in lysosomes of living cells. To facilitate cellular uptake of the peptide, we used a cell-penetrating helix 5 and a control peptide (3×D), that were C-terminally linked with a human immunodeficiency virus-derived TAT-motif (22). Furthermore, we added the chaperone-mediated autophagy (CMA) targeting motif KFERQ to support lysosomal import of these peptides (23). This helix 5—as well as the control (3×D) TAT-peptide showed a comparable effect on recombinant GC activity as observed for the unmodified peptides (FIG. 6G). Using immunofluorescence, we detected the helix 5 TAT-peptide in vesicular structures that partly co-localized with LIMP-2 in H4 human neuroglioma cells indicating lysosomal localization (FIG. 6H). Next, we confirmed that the helix 5 TAT-peptide could elevate GC activity directly within lysosomes of living cells by 18% using a compartment-specific activity assay (24) (FIG. 3G, 6I). As it has been previously demonstrated that elevated GC activity reduces α-synuclein levels (2, 11, 12), we investigated the effect of the helix 5 TAT-peptide on the clearance of α-synuclein in H4 cells, stably overexpressing wild-type α-synuclein under a tetracycline-inducible promoter. These cells were incubated with the helix 5 or the control (3×D) TAT-peptide and treated with doxycycline (dox) to suppress de novo α-synuclein synthesis. Cells were harvested at 0 and 74 hrs after dox addition and the remaining α-synuclein levels were analyzed by Western blot. Enhancement of GC activity persisted for the 74 hrs time course of the assay with the helix 5 TAT-peptide but not with the control 3×D TAT-peptide (FIG. 6J). A significant reduction in α-synuclein levels was observed 74 hrs post incubation with the helix 5 TAT-peptide, compared to 3×D control peptide (FIG. 3H, I). To further evaluate the therapeutic potential of the LIMP-2-derived helix 5 peptide, we assessed its effect on the recombinant GC mutant N370S, which represents one of the most prevalent GD-causing mutations with low catalytic activity (25, 26). Using a cell-free system, we found that recombinant N370S mutant GC could be precipitated by the helix 5 TAT-peptide as efficiently as recombinant wild-type GC (FIG. 3J), which is in good agreement with the localization of the N370S mutation outside of the three helical LIMP-2 binding motif (FIG. 6K). Furthermore, similar to the effect on wild-type GC (FIG. 3E) the helix 5 TAT-peptide led to a four-fold increase in the activity of the N370S mutant (FIG. 3K).

Our data provide evidence that the interaction site of LIMP-2 and GC consist of two hydrophobic helical interfaces. The integrity of these helical motifs on both proteins is critical for LIMP-2 mediated lysosomal transport of GC. Additionally, a LIMP-2-derived helix 5 peptide is sufficient for binding and activating wild-type but also mutant GC in vitro and in cell-based assays. We propose binding of the LIMP-2-derived helix 5 peptide to the hydrophobic three helix motif found on GC as described for LIMP-2 (FIG. 6K). The characterization of this interaction site on GC might have important implications for future drug design of GC activators.

Discussion

The determination of the crystal structures of LIMP-2 (15) and GC (16) and their respective binding sites revealed here, provides a deeper understanding of how this receptor/ligand protein complex triggers transport of GC to the lysosomal compartment. Our data suggest that LIMP-2 and GC interact via two helical interfaces in a 1:1 stoichiometry, which is consistent with our previous crosslinking experiments (1). The described helical interfaces on LIMP-2 and GC expose mainly hydrophobic side chains indicating a hydrophobic interaction. This notion is supported by our findings that introduction of negatively charged amino acids in either helical interface impaired the LIMP-2 binding to GC. The two clinically relevant GC mutations in helix 2 support this mode of interaction, since the I161S mutation decreases the hydrophobicity, whereas the P159L mutant interferes with the secondary structure of the helical motif of GC or neighboring protein structures. Interestingly, the hydrophobic helical motif is found opposite to the catalytic cavity and also to the proposed saposin C binding site (27, 28), suggesting that LIMP-2/GC interaction does not interfere with the binding of saposin C or with the enzyme activity. Furthermore, the LIMP-2/GC interaction site does not harbor glycosylation sites, which is in agreement with our previous findings of glycosylation-independent LIMP-2/GC interaction (1, 3). Our data propose a model in which sugar chains of both proteins come in close contact upon complex formation (FIG. 2J) potentially exerting a stabilizing effect on the LIMP-2/GC protein complex thereby assisting lysosomal transport of the enzyme. Interestingly, very few GD-causing mutations in GC have been reported within this interface region so far (5). It could be that such mutations do not affect the catalytic activity of GC but rather diminish its binding to LIMP-2, which could lead to secretion and recapture of a still functional enzyme via endocytosis. The amount of GC reaching lysosomes through this indirect pathway could be sufficient for several cell types to degrade sphingolipids (e.g. macrophages), as demonstrated by successful application of exogenous recombinant GC in enzyme replacement therapy (29-3_1).

Recently, Liou and coworkers proposed that the LIMP-2 binding motive consists of an 11 amino acid stretch in GC (32), which forms a surface accessible loop in close vicinity to the helical interface reported here. However, most of the residues within this loop mutated in this study, point toward the core of GC, suggesting a secondary effect on the helical motif rather than directly affecting binding.

We found that a LIMP-2-derived helix 5 peptide sufficiently binds to the helical motif of GC leading to a five-fold increase of recombinant GC activity. The use of this helix 5-derived peptide could offer a new strategy to efficiently purify GC from cell culture media or cell lysates. Moreover, this helix 5-derived LIMP-2 peptide could be exploited as an activator of wild-type and even mutant GC. The underlying mechanism of the helix 5 peptide-mediated GC activation remains to be established, but our in vitro assays already indicate a stabilizing effect of the peptide on the enzyme. We propose binding of the helix 5 peptide to the same hydrophobic interface of GC as described in this study for LIMP-2. Most of the recently described chaperones of GC are inhibitors of the enzyme (33, 34). In contrast, we propose here that the binding site of the helix 5 peptide resides outside the catalytic cavity of GC. Thus, we assume an allosteric, non-inhibitory effect of the bound helix 5 peptide on GC activity.

In summary, our study describes a helix motif in GC responsible for the interaction with LIMP-2 and presents a model of the receptor/ligand complex. It also reveals an activating effect of a small LIMP-2-derived peptide on GC. Identification of the peptide binding at this particular region on GC further opens the possibility to design small molecules to target this domain. Understanding the LIMP-2 interaction site in GC may further elucidate the molecular aspects of GD and AMRF and help optimize therapeutic strategies for patients. Preserving or enhancing LIMP2/GC interaction will be important in therapeutic efforts geared towards development of activators and chaperones of LIMP-2 or GC.

Experimental Procedures and Materials and Methods

Expression Plasmids.

Expression plasmids of LIMP-2 and human GC constructs were generated as described previously (1). For Western blotting nitrocellulose or PVDF membranes were used. EndoH/PNGaseF digests were performed according to manufacturer's instructions (New England Biolabs, Ipswich, USA). For co-immunoprecipitation experiments magnetic agarose G beads (Thermo Fisher Scientific, Waltham, USA) were utilized. Immunofluorescence studies were performed in cells as previously described (1, 3). Cellular co-localization of two proteins was determined by the Pearson's Index (35). Enzyme activity assays of cell lysates or recombinant protein were measured at acid pH using absorbent and fluorescent artificial substrates. For peptide studies, peptides were N-terminally tagged with biotin. If not stated otherwise, recombinant enzyme was incubated with a tenfold higher molarity of peptides. Conditions for pulldown experiments were kept at neutral pH. Protein modelling, molecular analyses, graphics and animations were performed with the UCSF Chimera package.

Statistical Analysis.

For statistical analyses, all values are expressed as the mean±SEM and analyzed via a two-sided, unpaired Student's t-test or One-Way ANOVA followed by a Tukey-Kramer multiple comparison test using GraphPad Instat 3 software when multiple samples were analyzed. In all analyses the null hypothesis was rejected at $p<0.05$ (*$p<0.05$, $p<0.01$, *$p<0.001$). If not indicated differently, significant differences in the graphs show GC/LIMP-2 mutants compared to each respective WT or buffer/control peptides compared to helix 5 peptide.

Expression Vectors and Transfection of Cells.

Murine and human wild-type/mutant LIMP-2 and wild-type/mutant GC cDNAs were cloned into the pFrog vector (a derivative of pcDNA3.1) using the HindIII and EcoRI restriction sites, according to refs. 1, 3, and 15 and were verified by sequencing (GATC Biotech AG). LIMP-2 and GC mutants were generated by site-directed mutagenesis. To insert a point mutation within a DNA sequence, the PCR protocol shown below was performed using a pfu DNA polymerase (Thermo Fisher Scientific). Oligonucleotides carrying the desired point mutations were purchased from Sigma Aldrich. All LIMP-2 constructs were C-terminally tagged with a myc sequence (EQKLISEEDL (SEQ ID NO:20)). Cells were transiently transfected with TurboFect (Thermo Fisher Scientific) according to the manufacturer's instructions. In brief, plasmid DNA (3 µg for a 10-cm dish and 1 µg for a 6-cm dish) was incubated with twice the amount of transfection reagent for 20 min in 100-500 µL DMEM high-glucose medium without the addition of FCS (PAA Laboratories) or penicillin/streptomycin (PAA Laboratories; GE Healthcare Life Sciences) before the transfection sample was added to the cells. The transfection reagent was removed ~6 h after transfection, and the cells were harvested 1-3 d after transfection.

SDS/PAGE and Western Blotting.

Cells were harvested by scraping them off the cell-culture dishes, pelleted (1,500×g; 4° C.), and lysed by sonification. As a standard lysis buffer, PBS (pH 7.4) including protease inhibitors (Complete; Roche) and 1% of the detergent Triton X-100 was used. For co-IP experiments the cells were lysed in EBC buffer (Table 3). Depending on the size of the cell pellets, 20-150 µL lysis buffer was applied, and the samples were sonicated 2×10 s, incubated on ice for 30 min, and sonicated again for 2×20s. Lysates then were centrifuged at 17,000×g for 10 min at 4° C. The lysed cell sample (supernatant) was transferred to a clean tube and used for protein concentration by using a BCA kit (Pierce, Thermo Fisher Scientific) according to the manufacturer's manual.

For Western blotting 20-40 µg of protein was loaded on a 10% Tris-SDS (made in house) or 4-12% Bis-Tris/NuPAGE Novex gel system (Thermo Fisher Scientific), subjected to electrophoresis, and blotted on nitrocellulose or PVDF membranes [2 h at 4° C. and 0.85 ampere (A) constant]. Membranes were blocked in 5% (wt/vol) milk Tris-buffered saline (TBS-T, pH 7.4, 0.1% Tween-20), and primary antibodies were incubated overnight (for more details on antibody dilutions see Table 4). PVDF membranes for α-synuclein detection were postfixed in 0.4% paraformaldehyde (PFA) (Polysciences Inc.) for 20 min after blotting. Signals were normalized to the respective loading controls [actin, neuronal-specific enolase (NSE), or GAPDH] (Table 4). Primary antibodies were incubated overnight at 4° C. After three washing steps in TBS-T the membranes were incubated for 1 h with the respective secondary antibody at room temperature. After the membrane was washed again three times with TBS-T, the signal of the antibody was detected using a chemiluminescence detection system (LAS4000; GE Healthcare Life Sciences) or by scanning on an infrared imager (Odyssey; LI-COR Biosciences).

Antibodies.

Table 4 gives detailed information about the primary antibodies used. Secondary antibodies used included Alexa Fluor 488 nm and 594 nm, biotinylated and peroxidase conjugates (Molecular Probes, Eugene, USA; Dianova, Hamburg, GER). For visualization peroxidase-conjugated secondary antibodies, signals were detected by chemiluminescence (SuperSignalWest, Pierce, Pittsburgh, USA) with densitometric analyses performed using Image J (Wayne Rasband, NIH).

Immunoblot for α-synuclein (C-20) were developed using the LI-COR imaging system. Accordingly, Alexa fluor labeled secondary antibodies were used and signal intensities were analyzed with Image Studio software (LI-COR Biosciences, Nebraska, USA).

Deglycosylation of Proteins/Molecular Shift Assay.

To study the subcellular localization and transport of the various GC mutants (ER, post-ER localization) endoglycosidase-H (EndoH) as well as Peptide-N-Glycosidase F (PNGaseF) digestions were performed. For both reactions 20 µg of protein was used and the experimental procedure was performed according to the manufacturer's handbook (New England Biolabs, Ipswich, USA). A positive digestion resulted in a molecular size shift of the protein. The ratio of post ER (70-74 kDa)/ER form (55 kDa) of GC was determined and used as a measurement of GC protein transport.

Co-Immunoprecipitation.

For co-immunoprecipitation (co-IP) studies cells were lysed in EBC-buffer (Table 3) and 500-1000 µg protein lysate was incubated with LIMP-2 antibody (Table 4) overnight at 4° C. Blocked (1% BSA) magnetic agarose G beads (Thermo Fisher Scientific, Life Technologies) were added to the lysates. Antibody precipitation was performed for 30 min. at room temperature. The beads were washed 4 times with EBC buffer. After the last wash, the supernatant was discarded carefully and the beads were incubated with Laemmli buffer (Table 3) at 60° C. for 15 min. and subsequently analyzed by SDS-PAGE and immunoblotting. Co-precipitated GC was visualised using an anti-human GC antibody (Table 4).

Peptides and Recombinant Proteins.

All peptides were purchased from jpt Peptide Technologies (Berlin, GER). Peptides and recombinant proteins (GC: Cerezyme, Genzyme Therapeutics, Boston, USA; LAMAN: human α-mannosidase, Zymenex, Hillerod, DK and LIMP-2 ectodomain R&D Systems Minneapolis, USA) were dissolved in sodium phosphate (NaPhosphate) buffer (50 mM, 150 mM NaCl, pH7). For peptide studies including pulldown, activity and uptake assays, recombinant GC was incubated with ten-fold higher molarity of the peptides unless otherwise stated. The concentration of the peptides as well as the recombinant proteins was determined spectroscopically (Nanodrop 2000c; Thermo Fisher Scientific, Waltham, USA).

Peptide-Pulldowns.

For the pulldown of recombinant protein utilizing LIMP-2-derived peptides, 2 nmol of protein (GC, LAMAN and BSA) was incubated overnight at 4° C. with the ten-fold molecular amount (20 nmol) of biotinylated LIMP-2-derived peptides (helix 5, 3×D as well as TAT-peptides (see Table 1)) at neutral pH. The total incubation volume was 250 µl (50 mM NaPhosphate buffer, 150 mM NaCl, pH7). 'High Capacity Streptavidin Beads' (Thermo Fisher Scientific, Waltham, USA) were blocked with 1% BSA solution and equilibrated with the NaPhosphate buffer. For each pulldown 50 µl of beads were utilized and incubated with 200 µl enzyme/peptide mixture for 30 min. at room temperature. The remaining 50 µl of the enzyme/peptide samples were prepared for SDS-PAGE (INPUT fraction). After incubation of the beads with the enzyme/peptide mixture the samples were centrifuged for 1 min. at 1,500×g at 4° C. The supernatant was removed and stored at 4° C. (UNBOUND fraction). Subsequently, the beads were washed three times with NaPhosphate buffer followed by centrifugation at 4,000 rpm at room temperature. The washing buffer was removed and the beads were incubated with 30 µl 1×Laemmli loading buffer (Table 3) at 60° C. for 20 minutes, which resulted in the release of the precipitated enzymes and peptides (BOUND fraction). The INPUT and BOUND fractions of the pulldown experiments were loaded on a NuPAGE® Novex® 4-12% Bis-Tris gels (Thermo Fisher Scientific, Waltham, USA), subjected to electrophoresis and stained with coomassie (Brilliant Blue, R-250; BioRad). After destaining the gels were scanned.

For pulldown of endogenous and overexpressed GC from N2a cell lysates 20 nmol of LIMP-2-derived peptide (Helix 5 and 3×D) was incubated with 50 µl cell lysate at 4° C. overnight. The cells were harvested in EBC-buffer (Table 3). After blocking and equilibration of the streptavidin beads (see above) the cell lysate/peptide mixtures were added to the beads for 30 min. at room temperature. The supernatant was removed. After extensive washing of the beads with NaPhosphate buffer, the bound peptides and proteins were released from the beads by incubation with Laemmli buffer (see above). After centrifugation for 2 min. at 17,000×g the supernatant was removed (BOUND fraction) and subjected to SDS-Page and Western-blotting. An antibody against human GC ($\alpha$-hGC, for details see Table 4) was used for detection.

Uptake Assay of LIMP-2-Derived TAT-Peptides in H4 Cells.

The $\alpha$-synuclein turn-over rate in the presence of the LIMP-2-derived peptides was assessed in human neuroglioma cells (H4), stably overexpressing $\alpha$-synuclein. To stop de-novo synthesis of $\alpha$-synuclein cells were treated with 2 µg/ml doxycycline at the start of the assay and incubated with 2 nmol of uptake-optimized TAT-peptides (helix 5 and 3×D helix 5; see Table 1) in 2 ml cell medium used for a 6 cm culture dish. For prolonged treatment of cells, new TAT peptides were applied to the cell media every 24 hours if a longer incubation time was needed.

Whole-Cell/Recombinant Protein Activity Assay.

To determine the enzymatic activity of the recombinant enzymes, lyophilized enzymes were reconstituted in the NaPi buffer described above. The lyophilized samples of wild-type GC (Cerezyme®) and the custom-made recombinant N307S mutant enzyme contain 0.01% polysorbate 80 (Tween 80) (see prescription information for Cerezyme® at the website for Cerezyme®). As indicated in our experiments, the concentration of the detergent is sufficient to support active GC enzyme and to perform the in vitro GC activity assays without adding further detergents to the reaction mix. For enzyme activity assays of recombinant proteins, 0.1-0.2 nmol of GC (Cerezyme®; N370S) and LAMAN were used in the absence or presence of 10× the molar amount of LIMP-2-derived peptides (Table 1) or LIMP-2 ectodomain (1-2 nmol) (Table 3).

Whole-cell or recombinant enzyme activity of GC and LAMAN was measured using 4-nitrophenyl $\beta$-D-glucopyranoside (FIGS. 3E and FIGS. 6D, F, and G) or 4-Methylumbelliferyl $\beta$-D-glucopyranoside (4 MU) (FIG. 3K) and 10 mM 4-nitrophenyl-N-acetyl-$\beta$-Dglucosaminide (FIG. 6E) (all substrates were purchased from Sigma-Aldrich). The artificial substrates were dissolved in sodium citrate buffer (0.2 M Na-citrate, 0.4% BSA, pH 4.6). All activity assays were performed at acid pH.

Cell lysate protein (20-200 µg) or recombinant protein (0.2 nmol GC/N370S or LAMAN) was incubated with 100 µL of 10 mM artificial absorbent substrate (4-nitrophenyl $\beta$-D-glucopyranoside or 4-nitrophenyl-N-acetyl-$\beta$-D-glucosaminide). The samples were incubated at 37° C. for 2 h to measure GC activity or for 5 h to assess LAMAN activity. The reaction was stopped by applying 500-1,000 µL of stop solution (0.4 M glycine, pH 10.4), and the absorbance was measured in a clear 96-well plate at 405 nm in a plate reader (Synergy HT; BioTek). Enzyme activities of cellular lysates were normalized to protein concentration (expressed in milliunits per milligram) and are shown relative to buffer control. Enzyme activities of recombinant proteins are shown as milliunits per milligram or are stated relative to buffer control.

Using the fluorescent substrate 4-MU (FIG. 3K), 10 µL of the recombinant enzyme/peptide mixture (0.1 nmol GC/N370S previously incubated with 1 nmol helix 5 TAT peptide in 50 mM NaPi buffer; total incubation volume 40 µL) were incubated directly with 60 µL of 0.2 M sodium citrate buffer and 10 µL of the substrate (5 mM dissolved in 0.2 M sodium citrate buffer) in a black-bottomed 96-well dish (Nunc no. 446473; Thermo Fisher Scientific). After the mixture was incubated at 37° C. for 30 min, 90 µL of stop solution (see above) was added. The fluorescence was assessed at an excitation wavelength of 365 nm and an emission wavelength of 445 nm in a SpectraMax i3 plate reader (Molecular Devices). GC activity is presented relative to buffer control.

Live-Cell Lysosomal Activity Assay.

Lysosomal GC activity in living cells was assessed by applying a drug-response assay in the presence and absence of a lysosomal inhibitor (bafilomycin A1; Invivogen) dissolved in DMSO (24). TAT peptides (10 µM) were added to the cell medium for 1 h; then H4 cells (see Table 5) were incubated with 100 µg/mL cell-permeable artificial substrate 5-(pentafluorobenzoylamino) fluorescein di-$\beta$-D-glucopyranoside (PFB-FDGlu) (Life Technologies, Thermo Fisher Scientific) for another hour. Cells were washed with warm medium; then the medium was replaced with phenol red-free neurobasal medium (Life Technologies, Thermo Fisher Scientific). The fluorescence intensity was recorded every 30 min for $\beta$-4 h in a SpectraMax i3 plate reader (Molecular Devices) (PFB-FDGlu: excitation=485 nm, emission=530 nm). After the final reading, cells were fixed in 4% formaldehyde/PBS and were stained with CellTag 700 (LICOR Biosciences) according to the manufacturer's instructions to measure cell volume. The plate was scanned on an Odyssey infrared imager (LI-COR Biosciences). Fluorescence intensities were normalized to cell volume and graphed versus time. Whole-cell activity was obtained by calculating the area below the DMSO curve. Nonlysosomal activity corresponds to the area under the bafilomycin A1 curve. Lysosomal activity was obtained by subtracting both areas (FIG. 6H).

Immunofluorescence and Pearson's Index.

IF studies were performed as previously described (1, 15). Cells were grown in six-well dishes on glass coverslips. If necessary, the cells were treated or transfected according to established protocols. When cells reached a confluency of 80%, they were fixed with 4% PFA (Polysciences, Inc.) in PBS for 20 min at room temperature. Then they were washed three times with PBS and were permeabilized for 5 min in 0.2% saponin (Sigma Aldrich) in PBS and for 10 min in 0.2% saponin (Sigma Aldrich)/0.12% glycine (Sigma Aldrich) in PBS at room temperature. To reduce unspecific binding of the antibodies, the cells were incubated for 20 min in 0.2% saponin/10% (wt/vol) FCS (PAA Laboratories) in PBS. The primary as well as the secondary antibody was diluted in this blocking solution [0.2% saponin/10% (wt/vol) FCS/PBS; see Table 4 for antibody dilutions]. The primary antibody was incubated for 1 h at room temperature or overnight at 4° C. in a wet chamber. Before incubation in secondary antibody, the coverslips were washed four times in 0.2% Saponin/PBS. The secondary antibody exhibits a fluorophore-labeling (Alexa Fluor 488 nm, 594 nm or 647 nm; Invitrogen, Thermo Fisher Scientific) and was applied in a concentration of 1:500 for 1 h at room temperature. After the coverslips were washed three times in 0.2% saponin/PBS and once in ddH2O, they were embedded on microscope slides with a mixture of DAPI/DABCO (both from Sigma Aldrich)/Mowiol (Calbiochem) (Table 3). The next day the samples were analyzed by confocal laser microscopy (FluoView 1000R; Olympus). The pictures were taken in the sequential mode to prevent an overlay of the different color channels. Cells were visualized at a magnification of 60-100× using oil objectives. The Pearson's correlation coefficient (PCC) was used to determine the colocalization of two proteins using the FV1000-ASW 3.0 Viewer-Software (Olympus). The PCC is a mathematical description of the degree of colocalization between two fluorophores (35).

For studies visualizing cellular peptide uptake, H4 cells (Table 5) were incubated for 8 h with 10 µM of helix 5 TAT peptide. The presence of the peptide was demonstrated after Alexa Fluor 488 streptavidin (1:300; Thermo Fisher Scientific) binding to the biotin tag of the peptide; then cells were co-stained for LIMP-2 (for antibody details, see Table 4).

Cd-Spectroscopy.

The CD-measurements were carried out with a Jasco-J-720-CD spectropolarimeter (Japan Spectroscopic Company, Oklahoma City, USA) at 20° C. The LIMP-2-derived peptides (helix 5, 3×D helix 5) were dissolved in 50 mM NaPhosphate buffer (+10 mM NaCl, pH 7) in a concentration of 0.2 µg/µl in a total volume of 300 µl and measured with settings as shown in Table 2.

TABLE 1

Peptide Sequences

| Peptide name | Sequence (N-terminus-----C-terminus) |
|---|---|
| Helix 5 | Biotin-Ttds-LREIIEAMLKAYQQKLFVTHTVDE (SEQ ID NO: 3) (acid) M = 3404 g/mol |
| 3×D Helix 5 | Biotin-Ttds-LREDDEAMDKAYQQKLFVTHTVDE (SEQ ID NO: 9) (acid) M = 3409 g/mol |
| Helix 5 TAT | Biotin-Ttds-*KFERQL*REIIEAMLKAYQQKLFVTHTVDE*YGRKKRRQRRR* (SEQ ID NO: 10) (amide) M = 5107 g/mol |
| 3×D Helix 5 TAT | Biotin-Ttds-*KFERQL*REDDEAMDKAYQQKLFVTHTVDE*YGRKKRRQRRR* (SEQ ID NO: 11) (amide) M = 5113 g/mol |
| Helical ctrl peptide: ADAM 17 "Conserved ADAM-seventeen Dynamic Interaction Sequence" (CANDIS) domain | N---KRVQDVIERFWDFIDQLSINTFGK (SEQ ID NO: 12)---C M = 2955 g/mol |

TABLE 2

Setting of CD-spectrum Measurements

| Settings: | |
|---|---|
| Data pitch | 1 nm |
| Scanning mode | continuous |
| Speed | 5 nm/min |
| Response | 8 sec. |
| Band width | 2.0 nm |
| Accumulation | 3 measurements |
| Wavelength | 250-200 nm |
| Width of cuvette | 0.05 cm |

TABLE 3

Buffer, Solutions, Recombinant Proteins

| Name | |
|---|---|
| Laemmli loading buffer | 500 mM Tris/HCl pH6.8<br>4% SDS<br>40% Glycerol<br>0.02% Bromophenol blue<br>400 mM Dithiothreitol (DTT) |
| EBC-buffer (cell lysis buffer for Co-IP experiments) | 50 mM Tris<br>120 mM NaCl<br>0.5% NP40<br>pH 7.4 (HCl)<br>1 tablet Complete ® (Roche, Basel, CH) |
| LIMP-2 ectodomain | Luminal domain of LIMP-2 with c-terminal human IgG-tag (R&D Systems, Minneapolis, USA), |
| LAMAN (recombinant human α-mannosidase) | Zymenex, Hillerod, DK |
| GC (Cerezym) | Genzyme Therapeutics, Boston, USA |
| GC-N370S | Custom-made |
| Mounting solution for IF experiments | 1 mL Mowiol solution [17% Mowiol/33% (vol/vol) glycerol in PBS; pH 6-7] 100 µL DABCO (200 mg/mL diazobicyclooctane; end concentration 50 mg/mL) 1 µL DAPI solution (end concentration 1 µg/mL) |

TABLE 4

Utilized Antibodies

| Name | Host | WB (dilution) | IF (dilution) | Source |
|---|---|---|---|---|
| anti-actin | rabbit | 1:1000 | — | Sigma Aldrich, St Louis, USA |
| anti-GAPDH | mouse | 1:2000 | — | EMD Millipore, Darmstadt, GER |
| anti-hGC (human β-glucocerebrosidase) | mouse | 1:500 | 1:250 | kindly provided by Johannes Aerts, Leiden University, NL |
| anti-LAMP-2 (Abl 93) | rat | 1:2000 | 1:200 | DSHB, Iowa City, USA |
| anti-LIMP-2 (L2T2) | rabbit | 1:1000 | 1:250 | Custom-made |
| anti-myc-GTX | goat | 1:1000 | 1:250 | Gentex, Cambridge, UK |
| anti-NSE, (neuronal specific enolase) | rabbit | 1:2000 | — | Polyscience, Warrington, USA |
| anti-PDI (A6, protein S-S isomerase) | rabbit | — | 1:750 | Abcam, Cambridge, UK |
| anti-α-Synuclein (C-20) | rabbit | 1:1000 | — | Santa Cruz Biotechnology, Dallas, USA |

TABLE 5

Cell Culture

| Name | Growth Medium |
|---|---|
| GC-deficient MEFs | High-glucose DMEM (4.5 g/mL) (GE Healthcare); additives: 10% FCS (PAA Laboratories), 1% penicillin/streptomycin (PAA Laboratories) |
| LIMP-2-deficient MEF cells | DMEM |
| H4 (human neuoglioma cells) overexpressing α-synuciein under the control of a tetracycline-inducible promoter ("tet-off") | Opti-MEM medium (Thermo Fisher Scientific); additives: 5% FCS, 1% penicillin/streptomycin, 200 µg/mL G418, 200 µg/mL hygromycin (both from Thermo Fisher Scientific) |
| N2a (murine neuroblastoma cells) | DMEM |
| Cos 7 | DMEM |

REFERENCES

1. Reczek D, et al. (2007) LIMP-2 is a receptor for lysosomal mannose-6-phosphate-independent targeting of beta-glucocerebrosidase. Cell 131(4):770-783.
2. Blanz J, et al. (2015) Mannose 6-phosphate-independent Lysosomal Sorting of LIMP-2. Traffic 16(10): 1127-1136.
3. Blanz J, et al. (2010) Disease-causing mutations within the lysosomal integral membrane protein type 2 (LIMP-2) reveal the nature of binding to its ligand beta-glucocerebrosidase. Hum. Mol. Genet. 19(4):563-572.
4. Berkovic S F, et al. (2008) Array-based gene discovery with three unrelated subjects shows SCARB2/LIMP-2 deficiency causes myoclonus epilepsy and glomerulosclerosis. American journal of human genetics 82(3):673-684.
5. Hruska K S, LaMarca M E, Scott C R, & Sidransky E (2008) Gaucher disease: mutation and polymorphism spectrum in the glucocerebrosidase gene (GBA). Human mutation 29(5):567-583.
6. Nails M A, et al. (2013) A multicenter study of glucocerebrosidase mutations in dementia with Lewy bodies. JAMA neurology 70(6):727-735.
7. Westbroek W, Gustafson A M, & Sidransky E (2011) Exploring the link between glucocerebrosidase mutations and parkinsonism. Trends in molecular medicine 17(9): 485-493.
8. Gegg M E, et al. (2012) Glucocerebrosidase deficiency in substantia nigra of parkinson disease brains. Annals of neurology 72(3):455-463.
9. Rothaug M, et al. (2014) LIMP-2 expression is critical for beta-glucocerebrosidase activity and alpha-synuclein clearance. Proceedings of the National Academy of Sciences of the United States of America 111(43): 15573-15578.
10. Bras J, et al. (2014) Genetic analysis implicates APOE, SNCA and suggests lysosomal dysfunction in the etiology of dementia with Lewy bodies. Human molecular genetics 23(23):6139-6146.
11. Sardi S P, et al. (2011) CNS expression of glucocerebrosidase corrects alpha-synuclein pathology and memory in a mouse model of Gaucher-related synucleinopathy. Proceedings of the National Academy of Sciences of the United States of America 108(29):12101-12106.
12. Sardi S P, et al. (2013) Augmenting CNS glucocerebrosidase activity as a therapeutic strategy for parkinsonism and other Gaucher-related synucleinopathies. Proceedings of the National Academy of Sciences of the United States of America 110(9):3537-3542.
13. Siebert M, Sidransky E, & Westbroek W (2014) Glucocerebrosidase is shaking up the synucleinopathies. Brain: a journal of neurology 137(Pt 5):1304-1322.
14. Mazzulli J R, et al. (2011) Gaucher disease glucocerebrosidase and alpha-synuclein form a bidirectional pathogenic loop in synucleinopathies. Cell 146(1):37-52.
15. Neculai D, et al. (2013) Structure of LIMP-2 provides functional insights with implications for SR-BI and CD36. Nature 504(7478):172-176.
16. Brumshtein B, Wormald M R, Silman I, Futerman A H, & Sussman J L (2006) Structural comparison of differently glycosylated forms of acid-beta-glucosidase, the defective enzyme in Gaucher disease. Acta Crystallogr. D. Biol. Crystallogr. 62(Pt 12):1458-1465.
17. Dvir H, et al. (2003) X-ray structure of human acid-beta-glucosidase, the defective enzyme in Gaucher disease. EMBO Rep. 4(7):704-709.
18. Cormand B, et al. (1998) Mutation analysis of Gaucher disease patients from Argentina: high prevalence of the RecNcil mutation. American journal of medical genetics 80(4):343-351.
19. Kawame H & Eto Y (1991) A new glucocerebrosidase-gene missense mutation responsible for neuronopathic Gaucher disease in Japanese patients. American journal of human genetics 49(6): 1378-1380.
20. Zhao Y, Ren J, Padilla-Parra S, Fry E E, & Stuart D I (2014) Lysosome sorting of beta-glucocerebrosidase by LIMP-2 is targeted by the mannose 6-phosphate receptor. Nature communications 5:4321.
21. Dusterhoft S, et al. (2015) Extracellular Juxtamembrane Segment of ADAM17 Interacts with Membranes and Is Essential for Its Shedding Activity. Biochemistry 54(38): 5791-5801.
22. Frankel A D & Pabo C O (1988) Cellular uptake of the tat protein from human immunodeficiency virus. Cell 55(6): 1189-1193.
23. Horst M, Knecht E C, & Schu P V (1999) Import into and degradation of cytosolic proteins by isolated yeast vacuoles. Molecular biology of the cell 10(9):2879-2889.
24. Mazzulli J R, Zunke F, Isacson O, Studer L, & Krainc D (2016) alpha-Synuclein-induced lysosomal dysfunction occurs through disruptions in protein trafficking in human midbrain synucleinopathy models. Proceedings of the National Academy of Sciences of the United States of America. 2016 Fe3b 16; 113(7):1931-6.
25. Liou B, et al. (2006) Analyses of variant acid beta-glucosidases: effects of Gaucher disease mutations. The Journal of biological chemistry 281(7):4242-4253.
26. Grace M E, Graves P N, Smith F I, & Grabowski G A (1990) Analyses of catalytic activity and inhibitor binding of human acid beta-glucosidase by site-directed mutagenesis. Identification of residues critical to catalysis and evidence for causality of two Ashkenazi Jewish Gaucher disease type 1 mutations. The Journal of biological chemistry 265(12):6827-6835.
27. Atrian S, et al. (2008) An evolutionary and structure-based docking model for glucocerebrosidase-saposin C and glucocerebrosidase-substrate interactions—relevance for Gaucher disease. Proteins 70(3):882-891.
28. Lieberman R L (2011) A Guided Tour of the Structural Biology of Gaucher Disease: Acid-beta-Glucosidase and Saposin C. Enzyme research 2011:973231.
29. Sly W S, Kaplan A, Achord D T, Brot F E, & Bell C E (1978) Receptor-mediated uptake of lysosomal enzymes. Progress in clinical and biological research 23:547-551.
30. Stahl P D, Rodman J S, Miller M J, & Schlesinger P H (1978) Evidence for receptor-mediated binding of glycoproteins, glycoconjugates, and lysosomal glycosidases by alveolar macrophages. Proceedings of the National Academy of Sciences of the United States of America 75(3): 1399-1403.
31. Pastores G M, et al. (2004) Therapeutic goals in the treatment of Gaucher disease. Seminars in hematology 41(4 Suppl 5):4-14.
32. Liou B, Haffey W D, Greis K D, & Grabowski G A (2014) The LIMP-2/SCARB2 binding motif on acid beta-glucosidase: basic and applied implications for Gaucher disease and associated neurodegenerative diseases. The Journal of biological chemistry 289(43):30063-30074.
33. Benito J M, Garcia Fernandez J M, & Ortiz Mellet C (2011) Pharmacological chaperone therapy for Gaucher disease: a patent review. Expert opinion on therapeutic patents 21(6):885-903.

34. Patnaik S, et al. (2012) Discovery, structure-activity relationship, and biological evaluation of noninhibitory small molecule chaperones of glucocerebrosidase. Journal of medicinal chemistry 55(12):5734-5748.
35. Pearson K (1909) Determination of the Coefficient of Correlation. Science 30(757):23-25.
36. Steet R A, et al. (2006) The iminosugar isofagomine increases the activity of N370S mutant acid beta-glucosidase in Gaucher fibroblasts by several mechanisms. Proceedings of the National Academy of Sciences of the United States of America 103(37):13813-13818.
37. Adler J & Parmryd I (2010) Quantifying Colocalization by Correlation: The Pearson Correlation Coefficient is Superior to the Mander's Overlap Coefficient. Cytom Part A 77A(8):733-742.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of references are made herein. All of the cited references are incorporated by reference herein in their entireties. In the event that there is an inconsistency between a definition of a term in the specification as compared to a definition of the term in a cited reference, the term should be interpreted based on the definition in the specification.

We claim:

1. A pharmaceutical composition comprising:
   (a) a peptide having a length of less than 30 amino acids and comprising the amino acid sequence of SEQ ID NO:3 or comprising an amino acid sequence having at least 70% sequence identity to the amino acid sequence of SEQ ID NO:3, wherein the peptide does not comprise the amino acid sequence of SEQ ID NO:4 or any portion thereof comprising at least 10 contiguous amino acids of SEQ ID NO:4, and the peptide is blocked at the N-terminus and/or C-terminus with a non-naturally occurring modification that increases stability of the peptide in plasma; and
   (b) a pharmaceutically acceptable carrier, excipient, or diluent.

2. The composition of claim 1, wherein one or more amide bonds of the peptide have been replaced with a non-amide bond.

3. The composition of claim 1, wherein the peptide comprises one or more non-natural amino acids.

4. The composition of claim 1, wherein the isolated peptide or isolated polypeptide exhibits one or more biological activities associated with lysosome membrane protein 2 (LIMP-2).

5. The composition of claim 1, wherein the isolated peptide or isolated polypeptide exhibits one or more biological activities associated with lysosome membrane protein 2 (LIMP-2) comprising binding to β-glucocerebrosidase, and increasing biological activity of β-glucocerebrosidase including hydrolysis of glycosylceramide by at least 50%.

6. A pharmaceutical composition comprising:
   (a) a peptide having a length of less than 30 amino acids and comprising the amino acid sequence of SEQ ID NO:3 or comprising an amino acid sequence having at least 70% sequence identity to the amino acid sequence of SEQ ID NO:3, wherein the peptide does not comprise the amino acid sequence of SEQ ID NO:4 or any portion thereof comprising at least 10 contiguous amino acids of SEQ ID NO:4, and the peptide has one or more non-naturally occurring modifications selected from the group consisting of acylation, acetylation, formylation, lipolylation, myristoylation, palmitoylation, alkylation, isoprenylation, prenylation, pegylation, glycosylation, and amidation; and
   (b) a pharmaceutically acceptable carrier, excipient, or diluent.

7. A method for treating a disease or disorder associated with the biological activity of β-glucocerebrosidase in a subject in need thereof, the method comprising administering to the subject the pharmaceutical composition of claim 1, wherein the disease or disorder is Gaucher disease, Parkinson's disease, or dementia with Lewy bodies.

* * * * *